(12) United States Patent
Lan et al.

(10) Patent No.: US 11,246,896 B2
(45) Date of Patent: Feb. 15, 2022

(54) TUMOR-SPECIFIC ADENOVIRUS VECTORS AND THERAPEUTIC USES

(71) Applicant: Board of Supervisors of Louisiana State University and Agricultural and Mechanical College, Baton Rouge, LA (US)

(72) Inventors: Michael Lan, New Orleans, LA (US); Mary Breslin, Las Vegas, NV (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 476 days.

(21) Appl. No.: 15/771,110

(22) PCT Filed: Oct. 28, 2016

(86) PCT No.: PCT/US2016/059382
§ 371 (c)(1),
(2) Date: Apr. 26, 2018

(87) PCT Pub. No.: WO2017/075395
PCT Pub. Date: May 4, 2017

(65) Prior Publication Data
US 2019/0247452 A1 Aug. 15, 2019

Related U.S. Application Data

(60) Provisional application No. 62/247,229, filed on Oct. 28, 2015.

(51) Int. Cl.
| | |
|---|---|
| *C12N 15/86* | (2006.01) |
| *A61K 35/761* | (2015.01) |
| *A61K 49/00* | (2006.01) |
| *G01N 33/50* | (2006.01) |
| *A61P 35/00* | (2006.01) |
| *C12Q 1/6886* | (2018.01) |

(52) U.S. Cl.
CPC ........ *A61K 35/761* (2013.01); *A61K 49/0097* (2013.01); *A61P 35/00* (2018.01); *C12N 15/86* (2013.01); *C12Q 1/6886* (2013.01); *G01N 33/50* (2013.01); *C12N 2710/10332* (2013.01); *C12N 2710/10343* (2013.01); *C12N 2840/007* (2013.01); *C12Q 2600/158* (2013.01)

(58) Field of Classification Search
CPC ... C12N 15/86; C12N 2840/007; A61K 35/61
See application file for complete search history.

(56) References Cited

U.S. PATENT DOCUMENTS

| | | |
|---|---|---|
| 5,789,542 A | 8/1998 | McLaughlin et al. |
| 5,925,565 A | 7/1999 | Berlioz et al. |
| 5,935,819 A | 8/1999 | Eichner et al. |
| 6,566,334 B1 | 5/2003 | McLaughlin et al. |
| 2004/0191761 A1 | 9/2004 | Routes |
| 2005/0037445 A1 | 2/2005 | Poulsen et al. |
| 2007/0134761 A1 | 6/2007 | Chatellard et al. |
| 2008/0267874 A1 | 10/2008 | Zeng |
| 2009/0238795 A1 | 9/2009 | Sehgal et al. |
| 2009/0275042 A1 | 11/2009 | Emans et al. |
| 2012/0316225 A1 | 12/2012 | Breslin et al. |

OTHER PUBLICATIONS

International Search Report for PCT/US2016/059382 dated Mar. 2, 2017.
Written Opinion for PCT?US2016/059382 dated Mar. 2, 2017.
Genbank Accession No. U07172 "Human insulinoma-associated (IA-1) gene, partial cds" Aug. 20, 1994. [Found onlines Jun. 2, 2017 at https://www.ncbi.nim.nih.gov/nuccore/U07172].
Genbank Accession No. U78775 "Gallus gallus HS4 insulator, partial sequence" Oct. 19, 2004. [Found online Jun. 2, 2017 at https://www.ncbi.nim.nih.gov/nuccore/U78775].
Genbank Accession No. AJ277959 "Cloning vector pHS4, luciferase reporter vecotr contianing HSF insulator sequence" Apr. 12, 2002. [Found online Jun. 2, 2017 at https:www.ncbi.nim.nih.gov/nuccore/AJ277959].
Aker, Mari, et al. "Extended core sequences from the cHS4 insulator are necessary for protecting retroviral vectors from silencing position effects." Human gene therapy 18.4 (2007): 333-343.
Akerstrom, V., et al. "Modifications to the INSM1 promoter to preserve specificity and activity for use in adenoviral gene therapy of neuroendocrine carcinomas." Cancer gene therapy 19.12 (2012): 828-838.
Argiris, Athanassios, and John R. Murren "Staging and clinical prognostic factors for small-cell lung cancer." Cancer Journal 7.5 (2001): 437-447.
Breslin, Mary B., et al. "Neuroendocrine differentiation factor, IA-1, is a transcriptional repressor and contains a specific DNA-binding domain: identification of consensus IA-1 binding sequence." Nucleic Acids Research 30.4 (2002): 1038-1045.

(Continued)

*Primary Examiner* — Marcia S Noble
(74) *Attorney, Agent, or Firm* — Baker Donelson

(57) ABSTRACT

A conditionally replicating adenovirus were generated that can specifically replicate and express therapeutic genes in neuroendocrine tumors. The promoter-specific expression of the adenoviruses is regulated upstream by an INSM1 (insulinoma-associated-1) promoter that is silent in normal adult tissues but active in developing neuroendocrine cells and neuroendocrine tumors. By placing the I NSM 1-promoter with an insulator and two copies of neuronal restrictive silencer elements in an adenoviral vector, the construct can retain tumor specificity and drive expression of a mutated adenovirus E1A gene (Δ24E1A) and the herpes simplex virus thymidine kinase gene. The I NSM1-promoter-driven viruses could replicate specifically in the I NSM1-positive cells and I NSM1-specific HSV-tk expression in combination with ganciclovir treatment displayed dose-dependent tumor cell-specific killing in insulinomas. When the INSM1-promoter driven HSV-tk was combined with Δ24E1A and I NSM 1 p-HSV-tk viruses, the co-infected insulinoma expressed higher levels of HSV-tk and more efficient tumor suppression as compared to the I NSM1 p-HSV-tk virus alone.

13 Claims, 42 Drawing Sheets

Specification includes a Sequence Listing.

(56) References Cited

OTHER PUBLICATIONS

Breslin, Mary B., Min Zhu, and Michael S. Lan. "NeuroD1/E47 regulates the E-box element of a novel zinc finger transcription factor, IA-1, in developing nervous system." Journal of Biological Chemistry 278.40 (2003): 38991-38997.
Brodeur, Garrett M., et al. "Revisions of the international criteria for neuroblastoma diagnosis, staging, and response to treatment." Journal of clinical oncology 11.8 (1993): 1466-1477.
Duggan, Anne, et al. "Transient expression of the conserved zinc finger gene INSM1 in progenitors and nascent neurons throughout embryonic and adult neurogenesis." Journal of Comparative Neurology 507.4 (2008): 1497-1520.
El-Amouri, Salim S., et al. "Secreted luciferase for in vivo evaluation of systemic protein delivery in mice." Molecular biotechnology 53.1 (2013): 63-73.
Farkas, Lilia M., et al. "Insulinoma-associated 1 has a panneurogenic role and promotes the generation and expansion of basal progenitors in the developing mouse neocortex." Neuron 60.1 (2008): 40-55.
Gierl, Mathias S., et al. "The zinc-finger factor Insm1 (IA-1) is essential for the development of pancreatic ß cells and intestinal endocrine cells." Genes & development 20.17 (2006): 2465-2478.
Goto, Y., et al. "A novel human insulinoma-associated cDNA, IA-1, encodes a protein with "zinc-finger" DNA-binding motifs." Journal of Biological Chemistry 267.21 (1992): 15252-15257.
Hayes, F. Ann, et al. "Surgicopathologic staging of neuroblastoma: Prognostic significance of regional lymph node metastases." The Journal of Pediatrics 102.1 (1983): 59-62.
Jann, Henning, et al. "Neuroendocrine tumors of midgut and hindgut origin: tumor-node-metastasis classification determines clinical outcome." Cancer 117.15 (2011): 3332-3341.
Koutsoudakis, George, et al. "A Gaussia luciferase cell-based system to assess the infection of cell culture-and serum-derived hepatitis C virus." PloS one 7.12 (2012): e53254.
Lan, Michael S., and Mary B. Breslin. "Structure, expression, and biological function of INSM1 transcription factor in neuroendocrine differentiation." The FASEB Journal 23.7 (2009): 2024-2033.
Lan, Michael S., et al. "IA-1, a new marker for neuroendocrine differentiation in human lung cancer cell lines." Cancer research 53.18 (1993): 4169-4171.
Li, Qing, Abner L. Notkins, and Michael S. Lan. "Molecular characterization of the promoter region of a neuroendocrine tumor marker, IA-1." Biochemical and biophysical research communications 236.3 (1997): 776-781.
Macejak, Dennis G., and Peter Sarnow. "Internal initiation of translation mediated by the 5' leader of a cellular mRNA." Nature 353.6339 (1991): 90-94.
Mellitzer, Georg, et al. "IA1 is NGN3-dependent and essential for differentiation of the endocrine pancreas." The EMBO journal 25.6 (2006): 1344-1352.
Mizuguchi, Hiroyuki, et al. "IRES-dependent second gene expression is significantly lower than cap-dependent first gene expression in a bicistronic vector." Molecular Therapy 1.4 (2000): 376-382.
Moolten, Frederick L., et al. "Lymphoma regression induced by ganciclovir in mice bearing a herpes thymidine kinase transgene." Human gene therapy 1.2 (1990): 125-134.
Mountain, C. F. "Clinical biology of small cell carcinoma: relationship to surgical therapy." Seminars in oncology. vol. 5. No. 3. 1978.
North, William G. "Gene regulation of vasopressin and vasopressin receptors in cancer." Experimental physiology 85.s1 (2000): 27s-40s.
Oyharcabal-Bourden, V., et al. "Standard-risk medulloblastoma treated by adjuvant chemotherapy followed by reduced-dose craniospinal radiation therapy: a French Society of Pediatric Oncology Study." Journal of clinical oncology 23.21 (2005): 4726-4734.
Packer, Roger J., et al. "Treatment of children with medulloblastomas with reduced-dose craniospinal radiation therapy and adjuvant chemotherapy: A Children's Cancer Group Study." Journal of clinical oncology 17.7 (1999): 2127-2127.
Pedersen, Nina, et al. "The insulinoma-associated 1: a novel promoter for targeted cancer gene therapy for small-cell lung cancer." Cancer gene therapy 13.4 (2006): 375-384.
Pelletier, Jerry, and Nahum Sonenberg. "Internal initiation of translation of eukaryotic mRNA directed by a sequence derived from poliovirus RNA." Nature 334.6180 (1988): 320-325.
Proye, Charles AG. "Endocrine tumours of the pancreas: an update." Australian and New Zealand journal of surgery 68.2 (1998): 90-100.
Richardson, et al (1993) Semin. Oncol. 20:105-127.
Rindi, Guido, and Bertram Wiedenmann. "Neuroendocrine neoplasms of the gut and pancreas: new insights." Nature Reviews Endocrinology 8.1 (2012): 54.
Taniwaki, Masaya, et al. "Gene expression profiles of small-cell lung cancers: molecular signatures of lung cancer." International journal of oncology 29.3 (2006): 567-575.
Wang, Hong-Wei, et al. "INSM1 promoter-driven adenoviral herpes simplex virus thymidine kinase cancer gene therapy for the treatment of primitive neuroectodermal tumors." Human gene therapy 20.11 (2009): 1308-1318.
Whyte, Peter, et al. "Association between an oncogene and an anti-oncogene: the adenovirus E1A proteins bind to the retinoblastoma gene product." Nature 334.6178 (1988): 124-129.
Wildner, Hendrik, et al. "Insm1 (IA-1) is a crucial component of the transcriptional network that controls differentiation of the sympathoadrenal lineage." Development 135.3 (2008): 473-481.
Xie, Jingping, et al. "The zinc-finger transcription factor INSM1 is expressed during embryo development and interacts with the Cbl-associated protein." Genomics 80.1 (2002): 54-61.

Fig. 2

Nicotinic acetyl choline receptor neuronal restrictive elements (NRSE) (SEQ ID NO: 2)

cagatct (TTCAGCACCACGGACAGCGCTC) (TTCAGCACCACGGACAGCGCTC) aagcttggtac

Fig. 3

HS4 insulator sequence (SEQ ID NO: 3)

```
   1 agagctcagg ggacagcccc cccccaaagc cccagggat gtaattacgt ccctcccccg
  61 ctaggggca gcagcgagcc gccgggggct ccgtccggt ccgcgctcc cccgcatcc
 121 ccgagccggc agcgtgggg gacagcccgg gcagggaa ggtgcacgg gatcgctttc
 181 ctctgaacgc ttctcgotgc tctttgagcc tgcagacacc tgggggata cgggaaaaa
 241 gcttaggct gaaagagaga ttagaatga cagaatcata gaacggcctg ggttgcaaag
 301 gagcacagtg ctcatccaga tccaacccc tgctatgtgc aggtcatca accagcagcc
 361 caggtgcc agagccacat ccagcctgc ctgaatgcc tgcaggatg ggcatccac
 421 agcctcttg ggcaacctgt tcagtgcgtc accacctct ggggaaaaa ctgcctctc
 481 atatccaacc caaacctccc ctgtctcagt gtgacacatg tccccctgt cctatcaagg
 541 gggagtttgc tgtgacatta ttggtctggg gtgacacatg tttgcaatt cagtgcatcs
 601 cggagaggca gatcttggga ataaggaagt gcaggacagc atggacgtgg gacatgcagg
 661 tgttgaggc tcggacac tctccaagtc acagcgttca gaacagcctt aaggataaga
 721 agataggata gaaggacaag gagcaagta aaacccagca tggagggag cacaaaagg
 781 ccacagacac tgctggtccc tgtgtctgac cctgcatgtt tgatcgtgtgc tggatgcaag
 841 cagaagggt ggaagagctt gcctggaga atacagctgg gtcagtagga ctggacagg
 901 cagctggaga attgccatgt agatgttcat acaatgtca aatcatgaag gctggaaag
 961 ccctccaaga tccccaagac caacccccaac ccaccccacg tgccacctgg cctgtcccct
1021 cagtgcaca tccccacagt tcttcatcac ctccagggac ggtgaccccc ccacctcgt
1081 gggcagtgt gcactgcag cacgcttctt tggagaaggt aaatcttgct aaatccagcc
1141 cgaccctccc ctgcacaac gtaaggccat tatctctcat ccaactccag gacggagtca
1201 gtgagatat t
```

Fig. 4

HS4 core sequence (SEQ ID NO: 4)

GAGTCACGGGACAGGGCCCCTGCCCAAGCCCCAGGGATGTAATTACGTCCTCCCCGCTACGGGGA
GCAGCGAGCCGCCCGGCCTTCGCTGTCGGGATCCCTCGGCAGTTTCCGGACCGCCAGCGTGCGGG
GACAGCCAGGCACGGCGGAGGTGGCAGGTGCTTCGGTCTCGCAGGCGTTCTCGAAGGTTCTGGAGG

TGCAGACGCTCGGGGATACGGGAAAAGTT

Fig. 5

Gaussia Luciferase (SEQ ID NO: 5)

GGATCCGCCACCATGGGAGTCAAGGTTCTGTTTGCCCTGATCTGCATCGCTGTGGCCGAGGCCAAGCCCA
CCGAGAACAACGAGGACTTCAACATCGTGGCCGTGGCCAGCAACTTCGCGACAACGATCTCGATGTGA
CCGGGGAAGTTGCCCGGAAGAGTGCCGAGGAAGTGCTCAAAGAGTGCCAAGAATCAAGTCCGGAAA
GCTGCTGACCAGGGCTGTCTGGAATCTGAAGGCGGAACCAAGAAGTGCACCGGGCCATGAAGAAGTTCA
TCCCAGGAGCGCTGGCCACCTACGAGGGCGACAAGGAGTCCTGGTGGGCGGCATAGGCGTCGATGCGT
CGAACATTCCTGAGATTCCTGGGTTCAAGGACTTGGAGCCCATGGAGCAGTTCATCGCACAGTCGATCTG

TGCTGTGGACTGCACAACTGGTGCGACCTTCAAGGGCTTCAACGTGCTTCTGACCTTCTCAAGAAGT
GGCTGCCGAACGCTGTGCGGACCTTTGCCAGGAAGATCCGGTGCCAGGTGACAAGATCAAGGGGCCGG

TGGTGACTAATGACGC
IRES (SEQ ID NO: 6)

| | | | | | |
|---|---|---|---|---|---|
| | | | | GCCCC | TCTCCCTCCC | CCCCCCCTAA | CGTTACTGGC |
| 701 | CGAAGCCGCT | TGGAATAAGG | CCGGTGTGCG | CCGGTGTGCG | TTTGTCTATA | TGTTATTTTC |
| 751 | CACCATATTG | CCGTCTTTTG | CCAATGTGAG | GGCCCGGAAA | CCTGGCCCTG | |
| 801 | TCTTTTGAC | GAGCATTCCT | AGGGGTCTTT | CCCTCTCGC | CAAACGGAATG | |
| 851 | CAAGTCTGT | TGAATGTCGT | GAAGGAAGCA | GTTCCTCTGG | AAGCTTCTTG | |
| 901 | AAGACAAACA | AGTGTGHAG | CGACCCTTTG | CAGGCAGCGG | AACCCCCAC | |
| 951 | CTGGCGACAG | GTGCCTCTGC | GGCCAAAGC | CACGTGTATA | AGATACACCT | |
| 1001 | GCAAAGGCGG | CACACCCCA | GTGCCACGTT | GTGAGTTGGA | TAGTTGTGGA | |
| 1051 | AAGAGTCAAA | TGGCTCTCCT | CAAGCGTATT | CAACAAGGGG | CTGAAGGATG | |
| 1101 | CCCAGAAGGT | ACCCATTGT | ATGGGATCTG | ATCTGGGGCC | TCGGTGCACA | |
| 1151 | TGCTTTACAT | GTGTTTAGTC | GAGGTTAAAA | AAACGTCTAG | GCCCCCCGAA | |
| 1201 | CCACGGGGAC | GTGGTTTTCC | TTTGAAAAAC | ACGATGATAA | TATGGCCACA | |

Fig. 7

Delta24E1A (SEQ ID NO: 7)

```
       a tgagacatat tatctgccac ggaggtgtta ttaccgaaga
aatggccgcc agtctttgg accagctgat cgaagagta ctgctgata atctccacc
tcctagccat tttgaccac ctaccctca cgaactctca gattttcgca tgaggccc
cgaagtccc aacgaggagg cgtttcgca gattttcca gactctgtaa tgtgcgt
gaggaagg atgactac tcactttcc gccggcgcc ggtctccgg agccgctca
ccttccgg cagccggcc agcggagca gagagcctg gtccgtt ctatgcaaa
cctgtaccg gagtgatct ttccacccag tgacgacgag gatgaagagg gtgagagt
tgtgttagat tatgtggagc accccgggca cggttgcag tcttgtcat atcaccgag
gaatacgggg gacccagata tatgtttc gcttgctat ataggacct gtggcatgtt
tgtctacagt agtgaaaat tatggcagt ggtgataga gtgtggtt tgtgtgta
atttttta taattctac agttttctgg tttaaagaat tttgtattgt gatttttta
aaggtctg tgtcgaacc tgtcgcgag aaccgaggcc cgacatcacc tgtgtctaga
accccggtc ctaaatggc gcctctatc ctgaagcgcc ctgagccgg ctgtctaga
gaatgcaata gtagtacgga tagctgtgac tccgtcctt ctaacacac tcctgata
caccgggtgg tccgctgtg cccattaaa ccagttgccg tgaggttgg tgggcgtcgc
caggtgtga aatgtatga ggactgtct aacgagcct ggcaacctt gcattgago
tgtaaagcc ccaggcata
```

*Fig. 8*

Human E1A from adenovirus 5 (SEQ ID NO: 8)

```
    mrhlichggv lteemaasll dqlieevlad nlpppshfep pthelvyldl vtapedpnee
 61 avsqifpdsv mlavqegidl ltfppapgsp epphisrgpe qpegralgpv smpnlvpevi
121 dlicheagfp psddedeege efvldveehp ghgcrschyh rrntgdpdim calcymrtcg
181 mfvyspvsep epepeppep arptcrrpkma pailrptpsp vsecnastd scdsqpsntp
241 peihpvpic plkpvavrvg grqavecle dllnepqgpl dlsckrprp
```

*Fig. 9*

Thymidine kinase (SEQ ID NO: 9)

```
atgcagcagatgcagtcggggcggggtccagtccacttcgcatattaaggtgacgtgtgcct
cgaacacgagacgctgcagccctgcggagccggttaacagtgcaacagtgccgagatctgttgcgtg
aaactcccgaactcttcggcacagcgcctttctgtagaagcgtatgcttcgtaccccggccatcaaacacg
cgtctgcgttcgaccaggctgcgcgttctcgcggagccatagcaacggacgctacggggttgcgcctcgcg
gcagcaagaagcaggatggaaaaccaaccgctgtgtggcagaaaatgcccactactcgggtttatatagacggt
cccacgcgggatggggaaaaaccaaccacacgacgcaactgctgtggcgctccgagacaatcgcgagatatgtc
acgtaccgcagccgatgactactggcgggtgtgggctgtggagcggcggttaatgacaagcgccagata
acaacacgcgctctatgcgtgaccgacgccgttctgcctgcggcctcatcgggggagctgagct
acaatgggcatgccccgcctgcggcctcatctcgacctctgaacctgaacctgaacctgatcccaatccgtctgtacccc
cacacggggcggtacttagggcagcatgtgttcggacctgtctgtgggtcgtgcctcatccgcg
ggcggcgcggtacctatggcagcatgtgtctgttgccacgagacagacacatcgcgccgttaggctactgc
acctggccggcaccgagcgcgtgctgggacgcgtatgctggtgcggggaggactggccctatcgggaggacgcc
caatacggtgcggtatctgcagtgccccgggtgccgagcccccagtgaacgcgaccccatataacgatacgcgccgtattta
gtcctgttccggcgcccccgagttgctggcctccatgcagtcgtccattaactcctgatccgccccagccggtgga
cgtcttcggcgaccctgctgcaactaccctcgggatcgccggagatggggagatggggaaacgcccgctcacacggga
cgatggggcctgcgaccaactgacagcacaatgacaaagagacagaagtcaaaaagcgcgtttggctggttg
taaaaaggcgccgcggttctcgtcctttccaccaccgcccacaggctgcactgatacgagtccaccaatggggca
ttcataaacggaagggttcgtcttccccggcctgccataggcactgccctgcccatgtgctaaaggcctgccaggtgaggccgtgggcaa
atacgcccggctgtaaggaggccctgccccactagccactgccaggttggggtgaaggccccaggctgcagc
aacgtcgggcggcccaggctgatgggggtaggtaggacgggtccccatgagcc
tggtttatggttcgtggggttattattattttgccgttaaggttcgtggggtcAGGTCCACCACCAGCC
```

*Fig. 10*

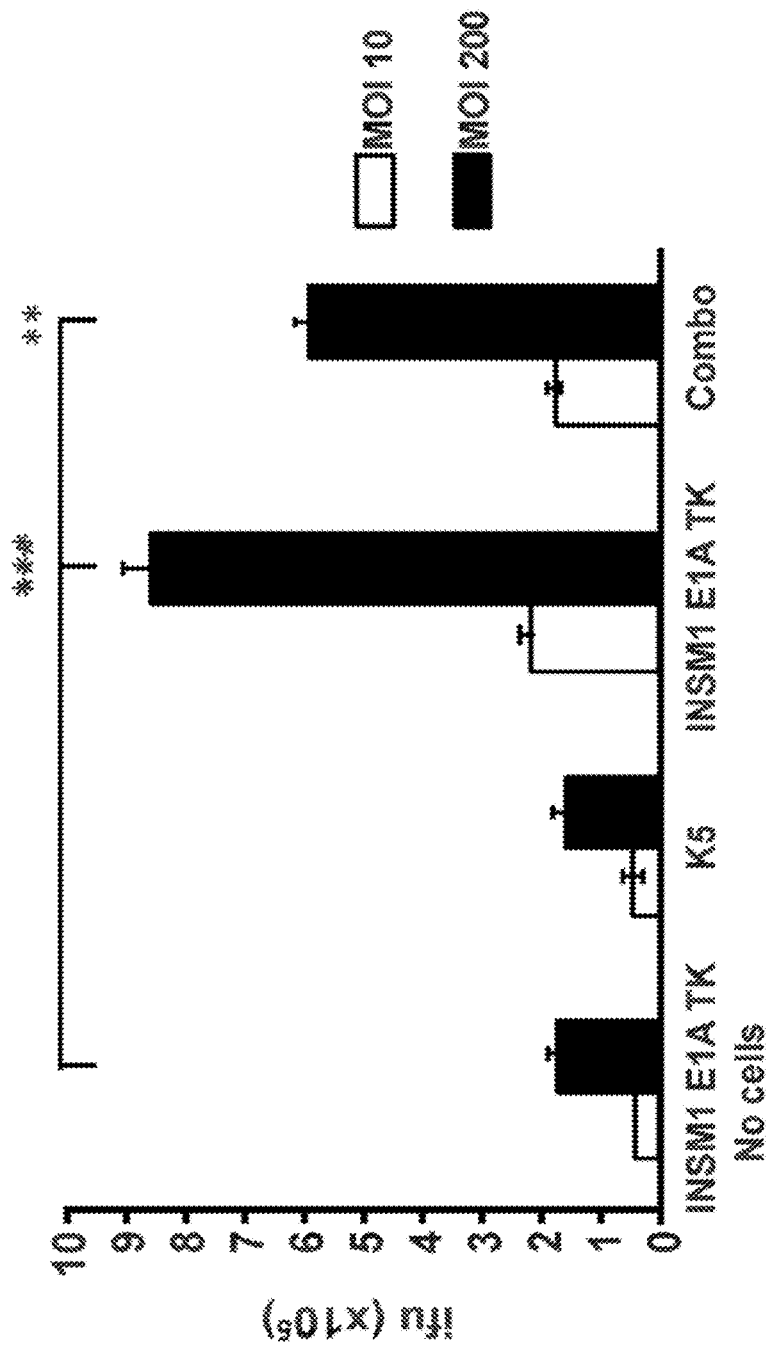

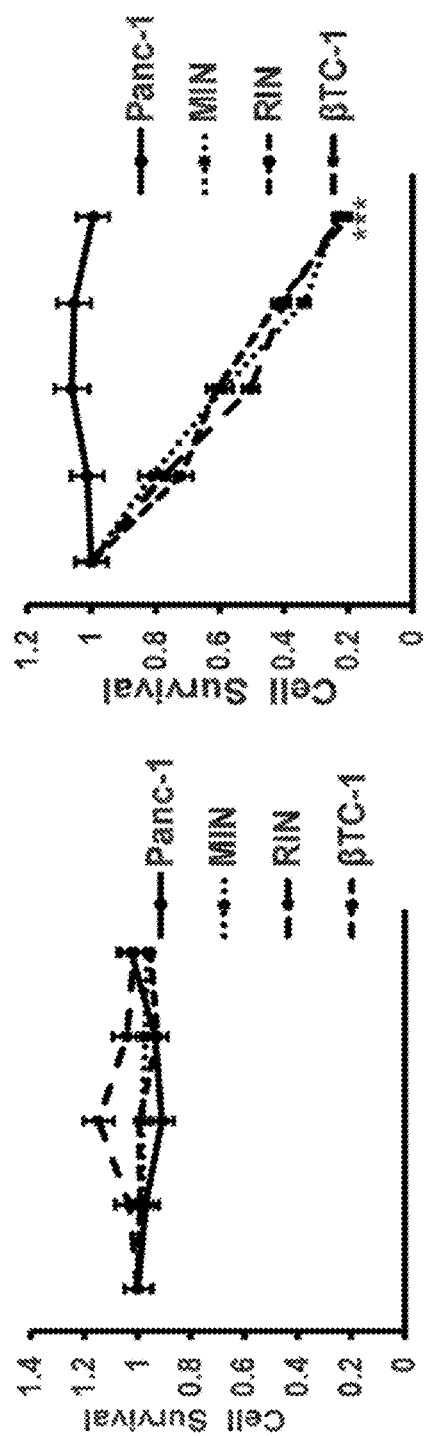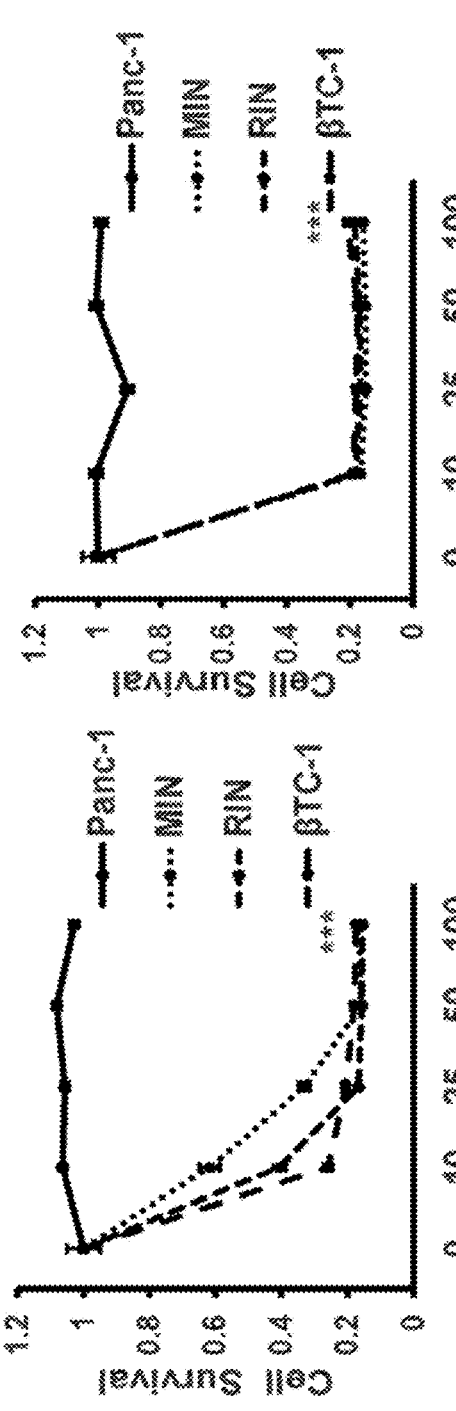
Fig. 13A  Fig. 13B  Fig. 13C  Fig. 13D

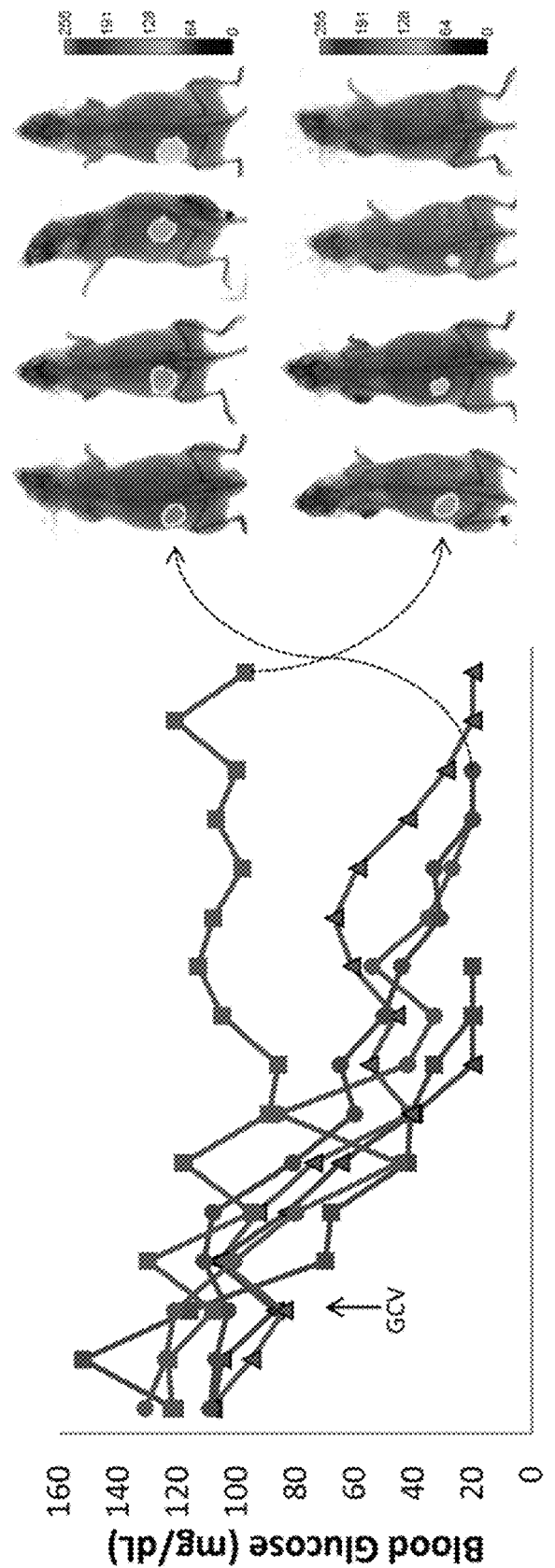

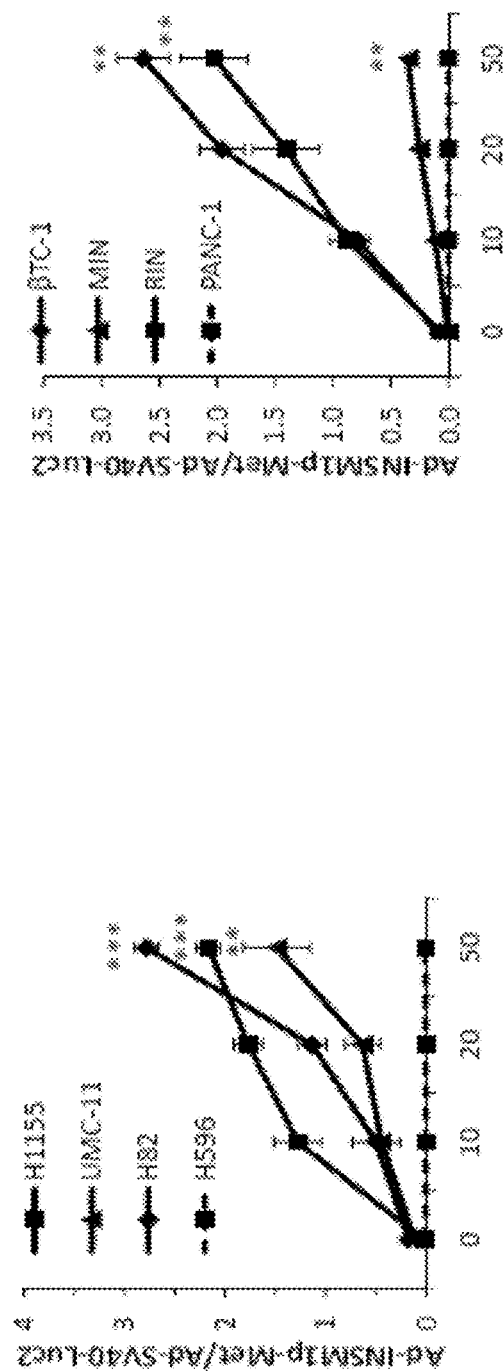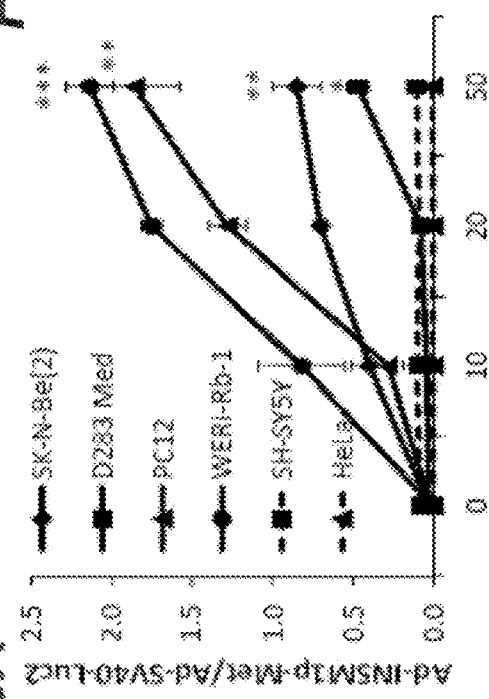

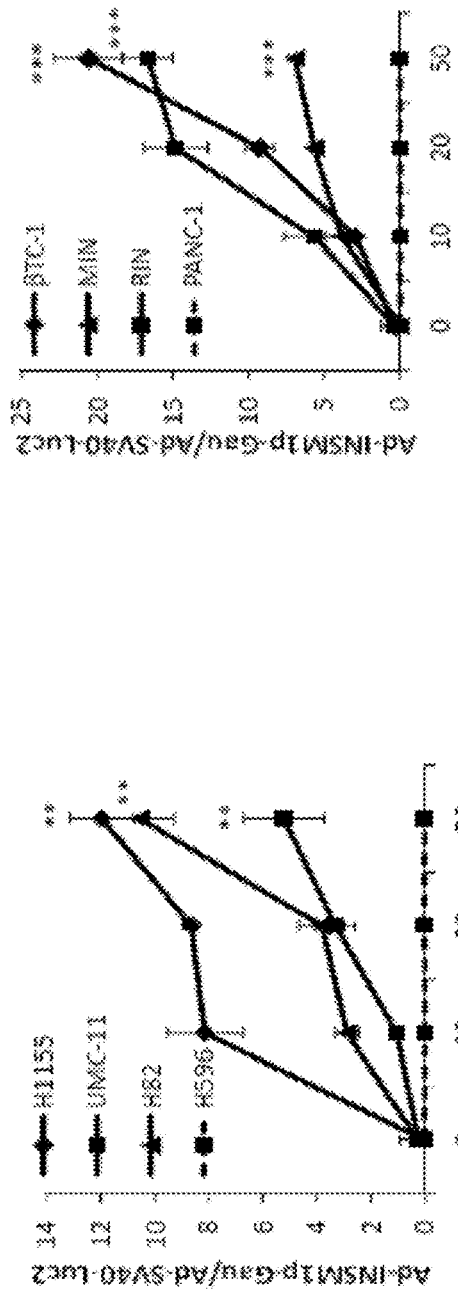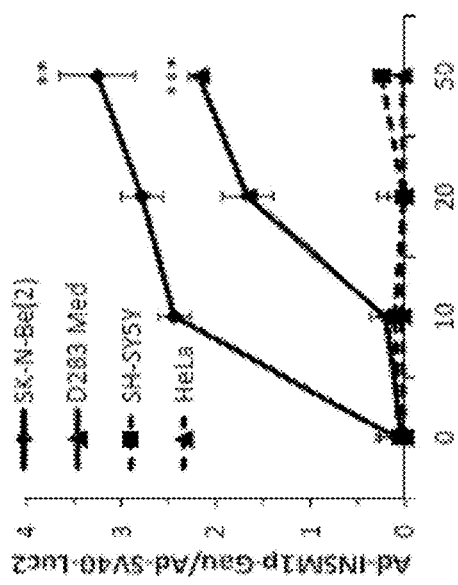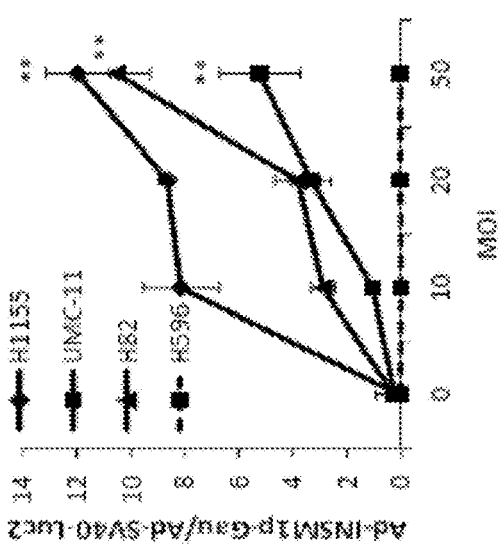
Fig. 20A
Fig. 20B
Fig. 20C

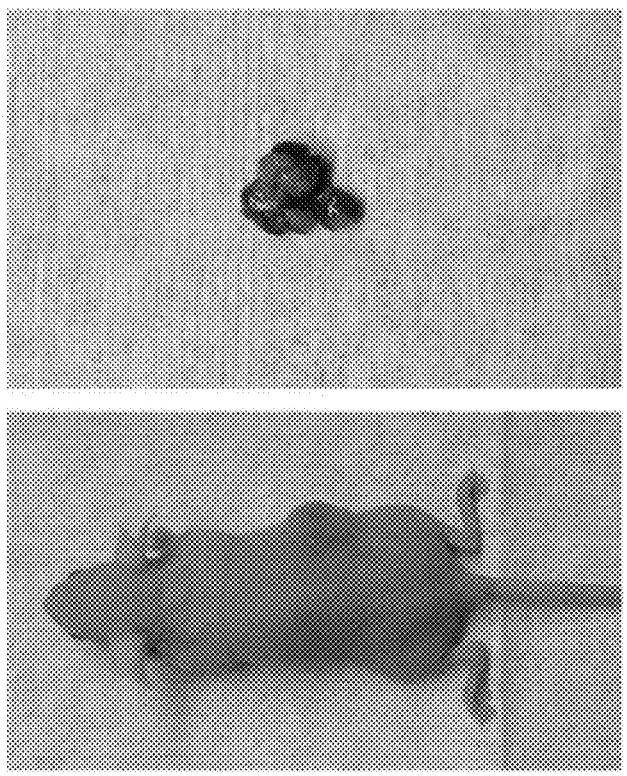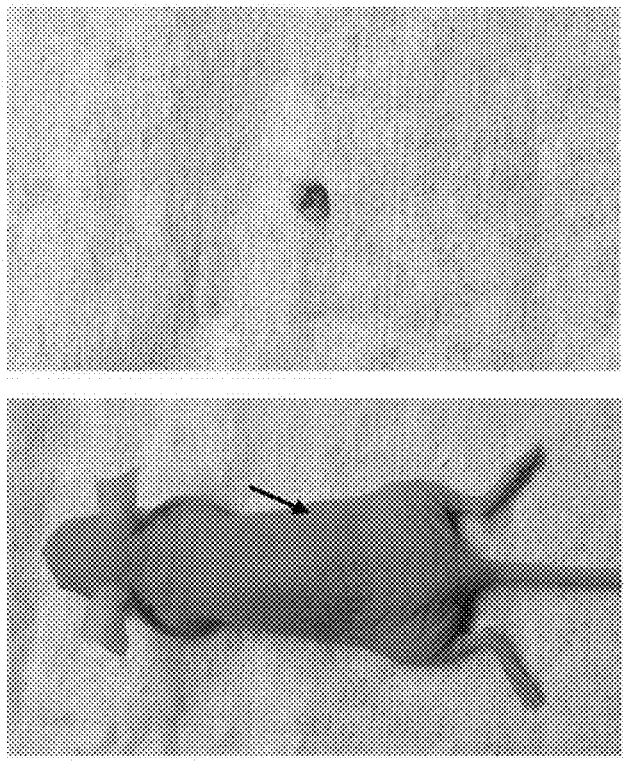
Fig. 28

Recombinant vector insert: 2Xins-INSM1p-2NRSE-D24E1A-IRES-HSVtk-3' untranslated region (SEQ ID NO: 11)

GAGCTCACGGGGACAGCCCCCCCCAAAGCCCCAGGGATGTAATTACGTCCCTCCCCCGCTAGGGGGCA
First insulator core sequence
GCAGCGAGCCGCCCGGGGCTCCGCTCCGGTCGGCGCTCCCCCGCATCCCCGAGCCGGCAGCGTGCGGG
First insulator core sequence
GACAGCCCGGGCACGGGAAGGTGGCACGGGATCGCTTTCCTCTGAACGCTTCTCGCTGCTCTTTGAGCC
First insulator core sequence
TGCAGACACCTGGGGGATACGGGGAAAAAGCTTGACCTCACGGGGACAGCCCCCCCCAAAGCCCCAGG GATGTAATTACGTCCCTCCCCCGCTAGGGGCAGCAGCGAGCCGCCCGGGGCTCCGCTCCGGTCGGCGC
Second insulator core sequence
TCCCCCGCATCCCCGAGCCGGCAGCGTGCGGGACAGCCCGGGCACGGGAAGGTGGCACGGGATCGCT
Second insulator core sequence
TTCCTCTGAACGCTTCTCGCTGCTCTTTGAGCCTGCAGACACCTGGGGGATACGGGGAAAAAGCTTGAGC
Second insulator core sequence
TCTTACGCGTGCTAGCCCaaagctttgcagaaaatgtttccttctctttcaataaagtgacatttttcct
INSM1
cacagcatatgacattttatgtggcttggctatttgttcccagtgttggacgatcagggccactcgca
INSM1
ctcgtgggttctctgccctgtccccgaagatctgccttttgtgtttcctcggggctggctggacag
INSM1
aggatggaggcaggcggcccagtctgggtccaaacggaacggcagcggaggtgggtggggtggggc
INSM1
gggggaatcttcgctgttgtctcttcctgtggcacagggaggcggcttgtcctctcggaggcctcag
INSM1
cctgcctcagagtacagattgccccccctcccccgtccagcacgcgtctctttgcgtccagattggcc
INSM1
gcgaccggagctcaatagcaggaggttaatttccttcacaaaggtgaaggggcacggctccgtgggc
INSM1
tgcgccagacaggcagcccctttatttcgcagcgccttgattggagccctttgatttagcatctgatgtca
INSM1
accggcaaacaaaatgcccgctcggaatgaaaatgcatgaggccgcgcgggaggagaaagccaacttca
INSM1
ctggggcgcacgaggccgacgcgcgtttcgggcttcggccaactcgaccggattaaccgagccttgga
INSM1
ccacgcggaagctccgggcggcctggtcggcccgcaaagatgccattcccaagcctccaagaaccca
INSM1
aaagttcagaaattcacgttcctctgggaaccagcccagcccgccgcgctccaatccgcgctttcgg
INSM1

*Fig. 32* gagactgagaaggcctgccaattccttctcaaactcgaagaaaccttctctagcccgtgggcgcg
INSM1 gaggctgcgagcacaaacatcgccctcggccactgccagaaggccggcccctgtccacacttggaacc
INSM1 ccgcggaaccttttgcttggctcttgggtccagcggccatcgtccaagtccggcggaggcgtcc
INSM1 cgacctgctgctctctcggattcttgtttatttcccaaacaccacgcagacgcactgcgctcgcaac
INSM1 gatctccccgaccgcccggcgcgcccgcccccaccaatcagcgcgcacaacttcccctcggct
INSM1 ccggctcggggattgaacctctgacatatttggggccattcttctccttgttgctattttgctagcg
INSM1 accgcgggtaatcccgcgcggagggggcgtgcattgtcgcgctgatggacgggccatttggcggc
INSM1 tccgcccccgagagagacacaaagccaggcacgtgcgctcccatagaagcagcagacgt
INSM1 gaaggaggcgggccggccgtgtgcctgaccggccggcgcgcgccggccgggcgaccagggc
INSM1 gcgcgcggggcccgcgcctcaggtacatctgccgacctaccggcgacccccgagtccggcccc
INSM1 ttttggccgcccatcgcctccacctgcagctgaggagctgcgacgactgattgctccaggg
INSM1 gaagcggaggcgagaacaatggccctccccgtaaaaggagcggctgccggccggggacagg
INSM1 gacgcgcgtgcaggcgcgagagctgggcgagccgtcgcGGCTCGAGTCTTTCAGCACCACGGACAGC
INSM1                                                      First NRSE

GCTCTTCAGCACCACGGACAGCGCTCGCGATCTAAGTTAAGCTTatgagacatattatctgccacggagg
                            Second NRSE tgttattaccgaagaaatggccgccagtcttttggaccagctgatcgaagaggtactggctgataatctt
Δ24E1A ccacctcctagccatttgaaccacctaccttcacgactgtatgatttagacgtgacggccccgaag
Δ24E1A atcccaacgaggaggcggtttcgcagattttcccgactctgtaatgttggcggtgcaggaagggattga
Δ24E1A cttactcactttccgccgcgcccggttctccggagccgctcacctttcccggcagcccgagcagcg
Δ24E1A gagcagagagccttgggtccggtttctatgccaaaccttgtaccggaggtgatctttccacccagtgacg
Δ24E1A acgaggatgaagagggtgaggagtttgtgttagattatgtggagcacccggcacggttgcaggtcttg
Δ24E1A

*Fig. 32-cont'd* tcattatcaccggaggaatacgnggaccagatattatgtgttcgctttgctatatgaggacctgtggc
Δ24E1A atgtttgtctacagtaagtgaaaattatgggcagtgggtgatagagtggtgggtttggtgtggtaatttt
Δ24E1A tttttttaatttttacagttttgtggtttaaagatttttgtattgtgattttttttaaaaggtcctgtgtct
Δ24E1A gaacctgagcctgagcccgagccagaaccggagcctgcaagacctaccgcgtcctaaaatggcgcctg
Δ24E1A ctatcctgagacgcccgacatcacctgtgtctagagaatgcaatagtagtacggatagctgtgactcgg
Δ24E1A tccttctaacacacctcctgagatacaccgggtggtccgctgtgcccattaaaccagttgccgtgaga
Δ24E1A gttggtgggcgtcgccaggctgtggaatgtatcgaggacttgcttaacgagcctgggcaacctttggact
Δ24E1A tgagctgtaaacgcccaggccataaGCCCTCTCCCTCCCCCCCCTAACGTTACTGGCCGAAGCCGC
IRES

TTGGAATAAGGCCGGTGTGCGTTTGTCTATATGTTATTTTCCACCATATTGCCGTCTTTTGGCAATGTGA
IRES

GGGCCCGGAAACCTGGCCCTGTCTTCTTGACGAGCATTCCTAGGGGTCTTTCCCCTCTCGCCAAAGGAAT
IRES

GCAAGGTCTGTTGAATGTCGTGAAGGAAGCAGTTCCTCTGGAAGCTTCTTGAAGACAAACAACGTCTGTA
IRES

GCGACCCTTTGCAGGCAGCGGAACCCCCCACCTGGCGACAGGTGCCTCTGCGGCCAAAGCCACGTGTAT
IRES

AAGATACACCTGCAAAGGCGGCACAACCCCAGTGCCACGTTGTGAGTTGGATAGTTGTGGAAAGAGTCAA
IRES

ATGGCTCTCCTCAAGCGTATTCAACAAGGGGCTGAAGGATGCCCAGAAGGTACCCCATTGTATGGGATCT
IRES

GATCTGGGGCCTCGGTGCACATGCTTTACATGTGTTTAGTCGAGGTTAAAAAACGTCTAGGCCCCCCGA
IRES

ACCACGGGACGTGGTTTTCCTTTGAAAAACACGATGATAATATGGCCACAGGATCCTTTCGaacacgca
IRES gatgcagtcggggcggcgcgtcccagtccacttcgcatattaaggtgacgcgtgtggcctcgaacacc
HSV-tk gagcgaccctgcagcgacccgcttaacagcgtcaacagcgtgccgcagatcttggtggcgtgaaactccc
HSV-tk gcacctcttcggccagcgccttgtagaagcgcgtatggcttcgtacccggccatcaacacgcgtctgcg
HSV-tk ttcgaccaggctgcgcgttctcgcggccatagcaaccgacgtacggcgttgcgccctcgccggcagcaag
HSV-tk

*Fig. 32-cont'd* aagccacggaagtcgccggagcagaaaatgcccacgctactgcgggtttatatagacggtcccacgg
HSV-tk gatggggaaaaccaccaccacgcaactgctggtggccctgggttcgcgcgacgatatcgtctacgtaccc
HSV-tk gagccgatgacttactggcgggtgctgggggcttccgagacaatcgcgaacatctacaccacacaacacc
HSV-tk gcctcgaccagggtgagatatcggccggggacgcggcggtggtaatgacaagcgcccagataacaatggg
HSV-tk catgccttatgccgtgaccgacgccgttctggctcctcatatcgggggggaggctgggagctcacatgcc
HSV-tk ccgccccggccctcaccctcatcttcgaccgccatcccatcgccgccctcctgtgctacccggccgcgg
HSV-tk ggtaccttatgggcagcatgaccccccaggccgtgctggcgttcgtggccctcatcccgccgaccttgcc
HSV-tk cggcaccaacatcgtgctgggggcccttccggaggacagacacatcgaccgcctggccaaacgccagcgc
HSV-tk cccggcgagcggctggacctggctatgctggctgcgattcgccgcgtttacgggctacttgccaatacgg
HSV-tk tgcggtatctgcagtgcggcgggtcgtggcgggagactgggacagctttcggggacggccggtgccgcc
HSV-tk ccagggtgccgagccccagagcaacgcggggccacgacccccatatcggggacacgttatttaccctgttt
HSV-tk cgggcccccgagttgctggccccaacgcgcgacctgtataacgtgtttgcctgggccttggacgtcttgg
HSV-tk ccaaacgcctccgttccatgcacgtctttatcctggattacgaccaatcgcccgccggctgccgggacgc
HSV-tk cctgctgcaacttacctccgggatggtccagaccacgtcaccacccccggctccataccgacgatatgc
HSV-tk gacctggcgcgcacgtttgccccgggagatggggagctaactgaaacacggaaggagacaataccggaa
HSV-tk ggaacccgcgctatgacggcaataaaaagacagaataaaacgcacgggtgttgggtcgtttgttcataaa
HSV-tk cgcggggttcgtcccagggctggcactctgtcgatacccaccgagacccattggggccaatacgccc
HSV-tk gcgtttcttccttttccccacccaccccccaagttcgggtgaaggcccagggctcgcagccaacgtcgg
HSV-tk ggcggcaggccctgccatagccactggccccgtgggttaggacgggtcccccatgggaatggtttat
HSV-tk ggttcgtggggttattatttttgggcgttgcgtggggtcAGGTCCACGACCCAAGCTTTCTAGAGTCGGG
HSV-tk

Fig. 32-cont'd

```
GCGGCCGCCGCTTCGACCAGACATGATAAGATACATTGATCAGTTTGGACAAACCACAACTAGAATGCA
                            3'-untranslated region
GTGAAAAAAATGCTTTATTTGTGAAATTTGTGATGCTATTGCTTTATTTGTAACCATTATAAGTGCAAT
                            3'-untranslated region
AAACAAGTTAACAACAACAATTGCATTCATTTTATGTTTCAGTTCAGGGGAGGTGTGGAGGTTTTTT
                            3'-untranslated region
AAAGCAAGTAAAACCTCTACAAATGTGGTAAAATCGATAAGGATCC
             3'-untranslated region
```

Fig. 32-cont'd

Recombinant vector insert: 2XIns-INSM1p-2XNRSE-Δ24E1A--IRES-HSV-tk-3'-untranslated region (SEQ ID NO: 12)

```
GAGCTCACGGGGACAGCCCCCCCCAAAGCCCCCAGGGATGTAATTACGTCCCTCCCCCGCTAGGGGGCA
GCACCGAGCCGCCCGGGGCTCCGCTCCGGTCCGGCGCTCCCCCCGCATCCCCGAGCCGGCAGCCGTGCCGGG
GACAGCCCGGGCACGGGGAAGGTGGCACGGGATCGCTTTCCTCTGAACGCTTCTCGCTGCTCTTTGAGCC
TGCAGACACCTGGGGATACGGGAAAAAGCTTGAGCTCACGGGGACAGCCCCCCCCAAAGCCCCCAGG
GATGTAATTACGTCCCTCCCCCGCTAGGGGGCAGCAGCGAGCCGCCCGGGGCTCCGCTCCGGTCCGGCGC
TCCCCCCGCATCCCCGAGCCGGCAGCGTGCCGGGACAGCCCGGGCACGGGGAAGGTGGCACGGGATCGCT
TTCCTCTGAACGCTTCTCGCTGCTCTTTGAGCCTGCAGACACCTGGGGATACGGGGAAAAAGCTTGAGC
TCTTACGCGTGCTAGCCCAAAGCTTTGCAGAAAATGTTTCCTTCTCTTTCAATAAAGTGACATTTTCCT
CACAGCATATGACATTTTATGTGGCTTGGCTATTTGTTCCCCAGTGTTGGACGATCAGGGCCACTACGCA
CTCGTGGGGTTCTCTGCCCTGTCCCCGAAGATTCTGCCTTTTGTGTTTCCTCGGGCTGGGCTGGACAG
AGGATGGAGGCAGGCGGCCCAGTCTGGGTCCAAACGGAACGGCAGCGGGAGGTGGGGGTGGGGGTGGGGGC
GGGGGGAATCTTCGCTGTTGTCTCTTCCTGGTGGACAGGGGAGGCGGCTTGTCCTCTCGGAGGCCTCAG
CCTGCCTCAGAGTACAGATTGCCCCCCCTCCCCCGTCCAGCACGCGTCTCTTTTGCGTCCAGATTGGCC
GCGACCGGAGCTCAATAGCAGGAGGTTAATTTCCTTCACAAAGGTGAAGGGGGCACGGCTCCGTGGGGC
TGCGCCAGACAGGCAGCCCCTTTATTTCGCAGCGCCTTGATTGGAGCCCTTGATTTAGCATCTGATGTCA
ACGGCAAACAAAATGCCCGCTCGGAATGAAAATGCATGAGGCCGCGCGGGGAGGAGAAAGCCAACTTCA
CTGGGGCGCACGAGGCCGACCGCCGCGTTTCGGGCTTCGGCCAACTCGACCCGGATTAACCGAGCCTTGGA
CCACGCGGAAGCTCCGGCGGCTGGGTCGGCCCCGCCAAAGATGCCATTCCCAAGCCTCCAAGAACCCA
AAAGTTCAGAAATTCACGTTCCTCTGGGAACCCAGCCCAGCCGCCCCGCGCTCCAATCCCGCGCTTTCGG
GAGACTGAGAAGGCCGTGCCAATTCCTTCTCAAACTCGAAAGAAACTTCTCTAGCCCCGTGGGCGCGCG
GAGGCTGCGAGCACAAACATCGCCCTCGGCCACTGCCAGAAGGCCGGCCCCCTGTCCACACTTGGAACC
CCGGGGAACCCTTTTGCTTGGCCTCTTGGGTCCAGCGGCCCATCCGTCCAAGGTCCGGCGGAGGCGTCC
GGACCCTGCTGCTCTCTGGATTCTTGTTTATTTCCAAACACCACGCGGACGCACTGCGCCTCCGCAAC
GATCTCCCCCGCACCGCCCCGGCGCGCCCCCGCCCCCACCCAATCAGCGCGCACAACTTCCCCCTCGGCT
CCGGCTCGCGGATTGAACCCTCCTGACATATTGGGGCATTCTTCTCCTTTGTTGCTATTTGCTAGCG
ACCCGCGGGTAATCCCCGCCGGGAGGGGGGCGTGCATTGTCGCGCTGATGGACGGGCCCATTTGGCGGC
TCCGCGCCCCCGGAGGAGAGACACAAAGCCCAGGCACGTGCGCCTCCCATAGAGAAGCAGCAGACCGT
GAAGGGAGGCGGGGCCGGGCGTGTGCCTGGACCGGCGGGGCGGCGGCGCCGGCGGGGCGACCAGGGGC
GCCGCGGGGCCCCGCGCCCTCAGGTACATCTGCCGCACCTACCGGGGACCCCGAGTCCCGCCCCC
TTTTGGCCGGCCCATCGGCCCTCCACCCTGCCAGGCTGAGGAGCTGGGACGCGCTGATTGGCTCCAGG
GAAGCGGGAGGCGAGAACAATGGCCCCCTCCCCCGTTAAAAGGGAGCGGCTGCCGGGGCCCGGGACAGG
GACGCGCGTGCAGGGCGCAGAGCTGGGCCGAGCCGTCGCCGGGCTCGAGTCTTTCAGCACCACGGACAGC
GCTCTTCAGCACCACGGACAGCGCTCGCGATCTAAGTTAAGCTTATGAGACATATTATCTGCCACGGAGG
TGTTATACCGAAGAAATGGCCGCCAGTCTTTTGGACCAGCTGATCGAAGAGGTACTGCTGATAATCTT
CCACCTCCTAGCCATTTTGAACCACTACCCTTCACGAACTGTATGATTAGACGTGACGGCCCCCGAAG
ATCCCAACGAGGAGGCGGTTTCGCAGATTTTTCCCGACTCTGTAATGTTGGCGGTGCAGGAAGGGATTGA
CTTACTCACTTTTCCGCCGGCGCCCGTTCTCCGGAGCCGCCTCACCTTTCCGGCAGCCGAGCAGCCG
GAGCAGAGAGCCTTGGGTCCGGTTTCTATGCCAAACCTTGTACCGGAGGTGATCTTTCCACCCAGTGACG
ACGAGGATGAAGAGGGTGAGGAGTTTGTGTTAGATTATGTGGAGCACCCCGGGCACGGTTGCAGGTCTTG
TCATTATCACCGGAGGAATACGGGGGACCCAGATATTATGTGTTCGCTTTGCTATATGAGGACCTGTGGC
ATGTTTGTCTACAGTAAGTGAAAATTATGGGCAGTGGGTGATAGAGTGGTGGGTTTGGTGTGGTAATTTT
TTTTTTAATTTTTACAGTTTTGTGGTTTAAAGAATTTTGTATTGTGATTTTTTAAAAGGTCCTGTGTCT
GAACCTGAGCCTGAGCCCGAGCCAGAACCGGAGCCTGCAAGACCTACCCGCCGTCCTAAAATGGCGCCTG
```

Fig. 33

```
CTATCCTGAGACGCCCGACATCACCTGTGTCTAGAGAATGCAATAGTAGTACGGATAGCTGTGACTCCGG
TCCTTCTAACACACCTCCTGAGATACACCCGGTGGTCCGCTGTGCCCATTAAACCAGTTGCCGTGAGA
GTTGGTGGGCGTCGCCAGCTGTGGAATGTATCGAGGACTTGCTTAACGAGCCTGGGCAACTTTTGGACT
TGAGCTGTAAACGCCCCAGGCCATAAGCCCCTCTCCTCCCCCCCCCTAACGTTACTGGTCGAAGCCGC
TTGGAATAAGGCCGGTGTGCGTTTGTCTATATGTTATTTTCTACCATATTGCCGTCTTTGGCAATGTGA
GGGCCCGGAAACCTGGCCCTGTCTTCTTGACGAGCATTCCTAGGGGTCTTTCCCTCTCGCCAAAGGAAT
GCAAGGTCTGTTGAATGTCGTGAAGGAAGCAGTTCCTCTGGAAGCTTCTTGAAGACAAACAACGTCTGTA
GCGACCCTTTGCAGCCACGGAACCCCCACCTGGCGACAGGTGCCTCTGCGGCAAAAGCCACGCGTAT
AAGATACACCTGCAAGGCGGCACAACCCCAGTGCCACGTTGTGAGTTGGATAGTTGTGGAAAGAGTCAA
ATGGCTCTCCTCAAGCGTATTCAACAAGGGCCTGAAGGATGCCCAGAAGGTACCCATTGTATGGGATCT
GATCTGGGGCCTCGGTGCACATGCTTTACATGTGTTAGTCGAGGTTAAAAAAACGTCTAGGCCCCCCGA
ACCACGGGGACCTGGTTTTCCTTTGAAAACACGATGATAATATGGCCACAAACACGCAGATGCAGTCGG
GGCGGCGCGGTCCCAGGTCCACTTCGCATATTAAGGTGACGCGTGTGGCCTCGAACACCGAGCGACCTG
CAGCGACCCGCTTAACAGCGTCAACAGCGTGCCGAGATCTTGGTGGCGTGAAACTCCCGCACCTCTTCG
GCCAGCGCCTTGTAGAAGCGCGTATGGCTTCGTACCCGGCCATCAACACGTCTGCGTTCGACCAGGC
TGCGCGTTCTCGCGGCCATAGCAACGACGTACGGCGTTGCGCCTCGCCCGCAGCAAGAAGCCACGGAA
GTCCGCCCGGAGCAGAAAATGCCCACGCTACTGCGGGTTTATATAGACGGTCCCACGGGATGGGGAAAA
CCACCACCACGCAACTGCTGGTGCCCTGGGTTCGCCGACGATATCGTCTACGTACCCGAGCTGATGAC
TTACTGGCGGGTGCTGGGGCTTCCGAGACAATCGCGAACATCTACACCACACAACACCGCTCGACCAG
GGTGAGATATCGGCCGGGACGCGGCGGTGGTAATGACAAGCGCCCAGATAACAATGGGCATGCCTATG
CCGTGACCGACGCCGTTCTGGCTCCTCATATCGGGGGGGAGCCTGGGAGTCACATGCCCGCCCCGGC
CCTCACCCTCATCTTCGACCGCCATCCATCGCCGCCTCTGTGCTACCCGGCGGCGGTACCTTATG
GGCAGCATGACCCCCAGCCGTGCTGGCGTTCGTGCCCTCATCCGCCGACCTTGCCCGGACCAACA
TCGTGCTTGGGCCCTTCCGGAGGACAGACACATTGACTGCTGGCTCAAACGCCAGTCCCTGGCTAGCG
GCTGGACCTGGCTATGCTGGCTGCGATTCGCCGCGTTTACGGGCTACTTGCAATACGGTGCGGTATCTG
CAGTGCGGCGGGTCGTGCGCGGAGGACTGGGACAGCTTTCGGGGACGGCCGTGCCGCCCAGGGTGCCG
AGCCCAGAGCAACGCGGCCCACGACCCCATATCGGGGACACGTTATTTACCCTGTTTCGGGTCCCGA
GTTGCTGGCCCCAACGGCGACCTGTATAACGTGTTTGCCTGGCCCTTGGACGTCTTGGGCAAACGCCTC
CGTTCCATGCACGTCTTTATCCTGGATTACGACCAATCGCCCGCCGCTGCCGGACGCCCTGCTGCAAC
TTACCTCCGGGATGGTCCAGACCCACGTCACCACCCCCGGCTCCATACGGACGATATGGGACCTGGCGG
CACGTTTGCCCGGGAGATGGGGAGGCTAACTGAAACACGGAAGGAGACAATACCCGAAGGAACCCGCC
TATGACGGCAATAAAAAGACAGAATAAAACGCACGGGTGTTGGTCGTTTGTTCATAAACGCGGGGTTCG
GTCCCAGGGCTGGCACTCTGTCGATACCCCACCGAGACTCCATTGGGGCCAATACGCCCGCGTTTCTTCC
TTTTCCCACCCCACCCCCAGTTCGGGTGAAGGCCCAGGGCTCGCAGCCAACGTCGGGGCGGCAGGCC
CTGCCATAGCCACTGGCCCGTGGTTAGGACGGGGTCCCCATGGGGAATGGTTTATGGTTCGTGGGG
GTTATTATTTTGGGCGTTGCGTGGGTCAGGTCCACGACCCAAGCTTTCTAGAGTCGGGGCGGCCGCCC
CTTCGAGCAGACATGATAAGATACATTGATGAGTTTGGACAAACCACAACTAGAATGCAGTGAAAAAAAT
GCTTTATTTGTGAAATTTGTGATGCTATTGCTTTATTTGTAACCATTATAAGCTGCAATAAACAAGTTAA
CAACAACAATTGCATTCATTTATGTTTCAGGTTCAGGGGGAGGTGTGGGAGGTTTTTAAAGCAAGTAA
AACCTCTACAAATGTGGTAAAATCGATAAGGATCC
```

*Fig. 33-cont'd*

Recombinant vector insert: 2Xins-INSM1p-2XNRSE-Δ24E1A-3'-untranslated region (SEQ ID NO: 13)

GAGCTCACGGGGACAGCCCCCCCCAAGCCCCCAGGGATGTAATTACGTCCTCCCCGCTAGGGGGCA
*First insulator core sequence*
GCAGCGAGCCGCCCGGGGCTCCGCTCCGGTCCGGCGCTCCCCCGCATCCCGAGCCGGCAGGGTGCGGG
*First insulator core sequence*
GACAGCCCGGGCACGGGGAAGGTGGCACGGGATCGCTTTCCTCTGAACGCTTCTCGGTTGCTCTTTGAGCC
*First insulator core sequence*
TGCAGACACCTGGGGGATACGGGGAAAAAGCTTGAGCTCACGGGACAGCCCCCCCCAAAGCCCCCAGG
*First insulator core sequence*    *Second insulator core sequence*
GATGTAATTACGTCCTCCCsequenceCCGCTAGGGGCAGCACGACCCGCCCGGGGCTCCGCTCCGG
*Second insulator core sequence*
TCCGGCGCTCCCCCGCATCCCGAGCCGGCAGGTGCGGGACAGCCCGGGCACGGGAAGGTGGCACG
*Second insulator core sequence*
GGATCGCTTTCCTCTGAACGCTTCTCGGTTGCTCTTTGAGCCTGCAGACACCTGGGGATACGGGGAAAAA
*Second insulator core sequence*
GCTTGAGCTCTTACGCGTGCTAGCCCaaagctttgcagaaaaatgtttccttctctttCAATAAAGTGAC
INSM1
ATTTCCTCACAGCATATGACATTTATGTGGCTTGGCTATTTGTTCCcagtgttggacgatcagggcc
INSM1
actacgcactcgtgggttctctgccctgtccccgaagattctgcctttgtgtttcctcggggctggg
INSM1
ctgacagagtatgtagtgcaggcgtcccagtctggtccaaacggaacggcagcggagtggggtgggg
INSM1
gtggggcggggggaatcttcgctgttgtctcttcctggtggcacaggggaggcggcttgtcctctcgga
INSM1
ggcctcagcctgcctcagagtacagattgccccccctcccccgtccagcacgcgtctcttttgcgtcca
INSM1
gattggccgcgaccggagctcaatagcaggaggttaatttccttcacaaaggtgaaggggcacggctcc
INSM1
gtggggctgcgccagacaggcagccccttttatttcgcagcgccttgattggagcccttgatttagcatc
INSM1
tgatgtcaaccggcaaacaaaatgcccgctcggaatgaaatgcatgaggccgcgcgggaggagaaagc
INSM1
caacttcactgggcgcacgagccgaccgcgcgtttcgggcttcggccaactgacccggattaaccga
INSM1
gccttggaccacgcggaagctccgggcggcctgggtcgccccgccaaagatgccattcccaagcctcca
INSM1

*Fig. 34* agaacccaaaagttcagaaattcacgttcctctggaaccagccagcccgcccgcgctccaatcccgc
INSM1 gctttcggagactgagaaggccgtgccaattcctctcaaactcgaaagaaaccttctctagcccgtg
INSM1 ggcgcgccggaggctacgagcacaaacatcgccctcgccactgccagaaggccggaccctgtccacac
INSM1 ttggaacccggggaaccctttttacttcacctctgtgtgtcagcggccatccgtccaagtccgggcg
INSM1 aggcgtccggacctgctgctctctcggattcttgtttatttcccaaacaccacgcggacgcactgccc
INSM1 tccgcaacgatctccccgcacgccccggcgcgcccccgccccacccaatcagcgcgcacaacttccc
INSM1 cctcggctccggctcgcggattgaaccctctgacatatttgggccattcttctcctttgttgctattt
INSM1 tgctagcgaccgcgggtaatcccgcgcggagcggggcgtgcattgtcgcgctgatggacgggccat
INSM1 ttggcggctccgcgccccccggaggagagacacaaagcccaggcacgtgcgcctccccatagagaagcag
INSM1 cagaccgtgaaggcaggcgggcggccgccgtgtgcctgaccgggcgggcggggcgccggccggagcga
INSM1 ccagggcgcgcgcggggccccgcgccctcaggtacatctgccgcacctacgggcgaccccgagtcc
INSM1 cggcccccttttggccgcccatcgccctcccaccctgccaggctgaggagctgcggacgcgctgattgg
INSM1 ctccaggggaagcggagcgagaacaatgcccctcccccgttaaaaggagcggctgccggaccg
INSM1 ggacagggacgcgcgtgcaaggcgcagagctggccgagccgtcgccGGGCTCGAGTCTTTCAGCACCA
INSM1                                                              FIRST
NRSE
CGGACAGGCTCTTCAGCACCACGGACAGGGCTGCGATCTAAGTTAAGCTTatgagacatattatctgc
NRSE         SECOND NRSE                                           Δ24E1A cacggaggtgttattaccgaagaaatggccgccagtcttttggaccagctgatcgaagaggtactggctg
Δ24E1A ataatcttccacctcctagccattttgaaccacctacccttcacgaactgtatgatttagacgtgacggc
Δ24E1A ccccgaagatcccaacgaggaggcggtttcgcagattttttcccgactctgtaatgttggcggtgcaggaa
Δ24E1A gggattgacttactcacttttccgccggcgccccggttctccggagccgcctccaccttttcccggcagccg
Δ24E1A

*Fig. 34-cont'd* agcagccggagcagagagccttgggtccggtttctatgccaaaccttgtacggaggtgatctttccacc
Δ24E1A
cagtgacgacgaggatgaagagggtgaggagtttgtgttagattatgtgagcacccggggcacggttgc
Δ24E1A
aggtcttgtcattatcaccggaggatacggggacccagatattatgtgttcgctttgctatatgagga
Δ24E1A
cctgtggcatgtttgtctacagtaagtgaaaattatggcagtgggtgatagagtggtgggtttggtgtg
Δ24E1A
gtaattttttttttaattttttacagttttgtggtttaaagaattttgtattgtgatttttttaaaaggtc
Δ24E1A
ctgtgtctgaacctgagcctgagccgagccagaaccggagcctgcaagacctaccgccgtcctaaaat
Δ24E1A
ggcgcctgctatcctgagacgccgacatcacctgtgtctagagaatgcaatagtagtacggatagctgt
Δ24E1A
gactccggtccttctaacacacctcctgagatacaccggtggtcccgctgtgcccattaaaccagttg
Δ24E1A
ccgtgagagttggtgggcgtcgccaggctgtggaatgtatcgaggacttgcttaacgagcctgggcaacc
Δ24E1A
tttggacttgagctgtaaacgccccaggccataaAGGTCCACGACCCAAGCTTTCTAGAGTCGGGCCGGC
Δ24E1A
CGGCCGCTTCGAGCAGACATGATAAGATACATTGATGAGTTTGGACAAACCACAACTAGAATGCAGTGAA
3'-untranslated region
AAAAATGCTTTATTTGTGAAATTTGTGATGCTATTGCTTTATTTGTAACCATTATAAGCTGCAATAAACA
3'-untranslated region
AGTTAACAACAACAATTGCATTCATTTTATGTTTCAGGTTCAGGGGGAGGTGTGGGAGGTTTTTTAAAGC
3'-untranslated region
AAGTAAAACCTCTACAAATGTGGTAAAATCGATAAGGATCC
3'-untranslated region

*Fig. 34-cont'd*

Recombinant vector insert: 2XIns-INSM1p-2XNRSE-Gaussia-3'-untranslated region (SEQ ID NO: 14)

GAGCTCACGGGGACAGCCCCCCCCAAAGCCCCCAGGGAGTAATTAGTCCCTCCCCCGTAGGGGCA
First insulator core sequence
GCAGGGAGCCGCCCGGGCTCCGTCCGGTCCGGGCTCCCCCGCATCCCCGAGCCGGCAGGTGCGGG
First insulator core sequence
GACAGCCCGGGCACGGGGAAGGTGGCACGGGATGGCTTTCTCTGAACGCTTCTCGGTGCTCTTGAGCC
First insulator core sequence
TGCAGACACCTGGGGGATACGGGGAAAAAGCTTGAGCTCACGGGGACAGCCCCCCCCAAAGCCCCCAGG
First insulator core sequence         Second insulator core sequence
GATGTAATTAGTCCCTCCCCCGTAGGGGCAGGACCGACGGCCCGGGGCTCCGCTCCGTCCGGGC
Second insulator core sequence
TCCCCCGCATCCCGAGCCGGCAGGTGCGGGGACAGCCCGGGCACGGGGAAGGTGGCACGGGATGGCT
Second insulator core sequence
TTCCTCTGAACGCTTCTCGGTGCTCTTGAGCCTGCAGACACCTGGGGGATACGGGGAAAAAGCTTGAGC
Second insulator core sequence
TCTTACGCGTGCTAGCCCaaagctttgcagaaaatgtttccttctctttcaataaagtgacatttcct
INSM
cacagcatatgacatttatgtggcttggctatttgttcccagtgttggacgatcagggccactacgca
INSM
ctcgtgggttctctgccctgtccccgaagattctgcctttgtgtttcctggggctggctggacag
INSM
aggatggaggcaggcggcccagtctgggtccaaacggaacggcagcggaagtgggagtgggtagggc
INSM
ggggggaatcttcgctgttgtctcttcctgtgtgcacagggaggcggcttgtcctctcggaggcctcag
INSM
cctgcctcagagtacagattgccccccctccccgtccagcacgggtctcttttgcgtccagattggcc
INSM
gcgacggagctcaatagcaggaggttaatttccttcacaaagtgaaggggcacggctccgtggggc
INSM
tgggccagacaggcagcccctttatttcgtagcgccttgattggagcccttgatttagcatctgatgtca
INSM
accggcaaacaaaatgccggctcggaatgaaaatgcatgaggccgcgcgggaggagaaagccaacttca
INSM
ctgggcgcacgaggcgaccgcgcgtttcgggcttcggccaactcgaccggattaaccgagcttgga
INSM
ccacgcggaagctcggggcggcctgggtcggcccggccaaagatgccattccaagctcaagaaccca
INSM

*Fig. 35* aaagttcagaaattcacgttcctctcgaaccagccagcccgcccgcgctccaatcccgcgctttcgg
　　　　　　　　　　　　　　　　　　INSM1 gagactgagaagccgtgccaattccttctcaaactcgaaagaaaccttctctagcccgtggcgcgcg
　　　　　　　　　　　　　　　　　　INSM1 gaggctgcgagcacaaacatcgccctcggccactgccagaagccggccccctgtccacacttggaacc
　　　　　　　　　　　　　　　　　　INSM1 ccggggaacccttttgcttggcctcttgggtcagcggccatccgtccaaggtccggcggaggcgtcc
　　　　　　　　　　　　　　　　　　INSM1 ggaccctgctgctctctcggattcttgtttatttcccaaacaccacgcggacgcactgcgcctccgcaac
　　　　　　　　　　　　　　　　　　INSM1 gatctccccgcacggccccggcgcgccccgcccccacccaatcagcgcgcacaacttcccctcggct
　　　　　　　　　　　　　　　　　　INSM1 ccggctcgcgattgaaccctcctgacatattgggccattcttctccttgttgctatttgctagcg
　　　　　　　　　　　　　　　　　　INSM1 accgcgggtaatcccgcgcggagggggcgtgcattgtcgcgctgatggacgggccatttggcggc
　　　　　　　　　　　　　　　　　　INSM1 tccgcgccccccgaggagagacacaaagcccaggcacgtgcgcctcccatagagaagcagcagaccgt
　　　　　　　　　　　　　　　　　　INSM1 gaacggaggcggccaggcatgtgcctggaccgggcggcgcgcgccaggcaggcgaccaggagc
　　　　　　　　　　　　　　　　　　INSM1 gcgcgcgggcgcccgcgccctcaggtacatctgccgcacctaccgggcgacccccgagtcccggcccc
　　　　　　　　　　　　　　　　　　INSM1 ttttggccgcccatcgccctcccaccctgccaggctgaggagctgcggacgcgctgattgcctccaggg
　　　　　　　　　　　　　　　　　　INSM1 gaagcggaggcgagaacaatgccccctccccccgttaaaaggcagcggctgccggccccggacagg
　　　　　　　　　　　　　　　　　　INSM1 gacgcgcgtgcagggcgcagagctgggccgagccgtcgccGGGCTCGAGTCTTTCAGCACCACGGACAGC
　　　　　　　　INSM1　　　　　　　　　　　　　　　　　First NRSE
GCTCTTCAGCACCACGGACAGCGCTCGCGATCTAAGTTAAGCTTGGATCCGCCACCatgggagtcaaagt
　　　　　　　　Second NRSE tctgtttgccctgatctgcatcgctgtggccgaggccaagcccaccgagaacaacgaagacttcaacatc
　　　　　　　　　　　　　　　　　Gaussia luciferase gtggccgtggccagcaacttcgcgaccacggatctcgatgctgaccgcgggaagttgcccggcaagaagc
　　　　　　　　　　　　　　　　　Gaussia luciferase tgccgctggaggtgctcaaagagttggaagccaatgcccggaaagctggctgcaccaggggctgtctgat
　　　　　　　　　　　　　　　　　Gaussia luciferase

*Fig. 35-cont'd*

```
ctgcctgtcccacatcaagtgcacgcccaagatgaagaagttcatccaggacgctgccacacctacgaa
```
Gaussia luciferase
```
ggcgacaaagagtccgcacagggcggcataggcgaggcgatcgtcgacattcctgagattcctgggttca
```
Gaussia luciferase
```
aggacttggagcccttggagcagttcatcgcacaggtcgatctgtgtgtggactgcacaactggctgcct
```
Gaussia luciferase
```
caaggggcttgccaacgtgcagtgttctgacctgctcaagaagtggctgcccaacgctgtgcgacctt
```
Gaussia luciferase
```
gccagcaagatccagggccaggtggacaagatcaagggggccggtggtgactaaGCGGCCGCAGGTCCAC
```
Gaussia luciferase
GACCCAAGCTTTCTAGAGTCGGGCGGCCGGCCGCTTCGAGCAGACATGATAAGATACATTGATGAGTTT
3'-untranslated region
GGACAAACCACAACTAGAATGCAGTGAAAAAAATGCTTTATTTGTGAAATTTGTGATGCTATTGCTTTAT
3'-untranslated region
TTGTAACCATTATAAGCTGCAATAAACAAGTTAACAACAACAATTGCATTCATTTATGTTTCAGGTTCA
3'-untranslated region
GGGGGAGGTGTGGGAGGTTTTTTAAAGCAAGTAAAACCTCTACAAATGTGGTAAAATCGATAAGGATCC
3'-untranslated region

Fig. 35-cont'd

SEQUENCE LISTING

<160> NUMBER OF SEQ ID NOS: 14

<210> SEQ ID NO 1
<211> LENGTH: 1702
<212> TYPE: DNA
<213> ORGANISM: Artificial sequence
<220> FEATURE:
<223> OTHER INFORMATION: INSM1 promoter
<220> FEATURE:
<221> NAME/KEY: misc_feature
<222> LOCATION: (2)..(7)
<223> OTHER INFORMATION: HindIII site

<400> SEQUENCE: 1

```
aaagctttgc agaaaaatgt ttccttctct ttcaataaag tgacattttc ctcacagcat      60
atgacatttt atgtggcttg ctatttgtt ccccagtgtt ggacgatcag ggccactacg     120
cactcgtggg gttctctgcc ctgtcccccg aagattctgc cttttgtgtt tcctcggggc    180
tgggctggac agaggatgga ggcaggcggc ccagtctggg tccaaacgga acggcagcgg    240
aggtggggggt gggggtgggg gcggggggaa tcttcgctgt tgtctcttcc tggtggcaca    300
ggggaggcgg cttgtcctct cggaggcctc agcctgcctc agagtacaga ttgccccccc    360
tcccccccgtc cagcacgcgt ctcttttgcg tccagattgg ccgcgaccgg agctcaatag    420
caggaggtta atttccttca caaggtgaa ggggcacgg ctccgtgggg gctgcgccag      480
acaggcagcc cctttatttc gcagcgcctt gattggagcc cttgatttag catctgatgt    540
caaccggcaa acaaaatgcc cgctcggaat gaaaatgcat gaggccgcgc ggggaggaga    600
aagccaactt cactggggcg cacgaggccg accgcgcgtt tcgggcttcg gccaactcga    660
cccggattaa ccgagccttg gaccacgcgg aagctccggg cggcctgggt cggccccgcc    720
aaagatgcca ttcccaagcc tccaagaacc caaaagttca gaaattcacg ttcctctggg    780
aacccagccc agcccgcccg cgctccaatc ccgcgctttc gggagactga gaaggccgtg    840
ccaattcctt ctcaaactcg aaagaaacct tctctagccc cgtgggcgcg cggaggctgc    900
gagcacaaac atcgccctcg gccactgcca gaaggccggg ccccctgtcc acacttggaa    960
ccccgggaa cccttttgct tggcctcttg ggtccagcgg cccatccgtc caaggtccgg    1020
gcggaggcgt ccggaccctg ctgctctctc ggattcttgt ttatttccca aacaccacgc   1080
ggacgcactg cgcctccgca acgatctccc ccgcaccgcc ccggcgcgcc cccgccccca   1140
cccaatcagc gcgcacaact tcccctcgg ctccggctcg cggattgaac cctcctgaca    1200
tatttggggc cattcttctc ctttgttgct attttgctag cgacccgcgg gtaatccccg   1260
cgcgggaggg gggcgtgcat tgtcgcgctg atggacgggc ccatttggcg gctccgcgcc   1320
ccccggagga gagacacaaa gcccaggcac gtgcgcctcc ccatagagaa gcagcagacc   1380
gtgaagggag gcggggccgg gcgtgtgcct ggaccgggcg gggcggcggc gccgggcggg   1440
gcgaccaggg gcgcgcgcgg gggccccgcg ccctcaggta catctgccgc acctaccggg   1500
cgacccccga gtcccggccc ccttttggcc gccccatcgc cctcccaccc tgccaggctg   1560
aggagctgcg gacgcgctga ttggctccag gggaagcggg aggcgagaac aatggccccc   1620
tccccccgtt aaagggagc ggctgccggg cccggggaca gggacgcgcg tgcagggcgc   1680
agagctgggc cgagccgtcg cc                                            1702
```

<210> SEQ ID NO 2
<211> LENGTH: 62
<212> TYPE: DNA
<213> ORGANISM: Artificial sequence

```
<220> FEATURE:
<223> OTHER INFORMATION: Tandem N-acetylcholine receptor (NRSE) elements
<220> FEATURE:
<221> NAME/KEY: misc_feature
<222> LOCATION: (2)..(7)
<223> OTHER INFORMATION: Bgl II site
<220> FEATURE:
<221> NAME/KEY: misc_feature
<222> LOCATION: (8)..(29)
<223> OTHER INFORMATION: First nictonic acetylcholine receptor neuronal
      restrictive silencer element (NRSE)
<220> FEATURE:
<221> NAME/KEY: misc_feature
<222> LOCATION: (30)..(51)
<223> OTHER INFORMATION: Second nictonic acetylcholine receptor neuronal
      restrictive silencer element (NRSE)
<220> FEATURE:
<221> NAME/KEY: misc_feature
<222> LOCATION: (52)..(57)
<223> OTHER INFORMATION: HindIII site

<400> SEQUENCE: 2
cagatctttc agcaccacgg acagcgctct tcagcaccac ggacagcgct caagcttggt      60
ac                                                                    62

<210> SEQ ID NO 3
<211> LENGTH: 1211
<212> TYPE: DNA
<213> ORGANISM: Artificial sequence
<220> FEATURE:
<223> OTHER INFORMATION: HS4 insulator sequence
<220> FEATURE:
<221> NAME/KEY: misc_feature
<222> LOCATION: (1)..(6)
<223> OTHER INFORMATION: Saci site
<220> FEATURE:
<221> NAME/KEY: misc_feature
<222> LOCATION: (1)..(6)
<223> OTHER INFORMATION: SacI site
<220> FEATURE:
<221> NAME/KEY: misc_feature
<222> LOCATION: (1206)..(1211)
<223> OTHER INFORMATION: SspI site

<400> SEQUENCE: 3
gagctcacgg ggacagcccc ccccaaagc ccccagggat gtaattacgt ccctccccg       60 ctaggggca gcagcgagcc gcccggggct ccgctccggt ccggcgctcc ccccgcatcc     120
ccgagccggc agcgtgcggg gacagcccgg gcacggggaa ggtggcacgg gatcgctttc    180
ctctgaacgc ttctcgctgc tctttgagcc tgcagacacc tgggggata cggggaaaaa     240 gctttaggct gaaagagaga tttagaatga cagaatcata gaacgcctg ggttgcaaag     300 gagcacagtg ctcatccaga tccaaccccc tgctatgtgc agggtcatca accagcagcc    360
caggctgccc agagccacat ccagcctggc cttgaatgcc tgcagggatg gggcatccac    420
agcctccttg ggcaacctgt tcagtgcgtc accaccctct gggggaaaaa ctgcctcctc    480
atatccaacc caaacctccc ctgtctcagt gtaaagccat tccccttgt cctatcaagg     540 gggagtttgc tgtgacattg ttggtctggg gtgacacatg tttgccaatt cagtgcatca    600
cggagaggca gatcttgggg ataaggaagt gcaggacagc atggacgtgg gacatgcagg    660
tgttgagggc tctggacac tctccaagtc acagcgttca gaacagcctt aaggataaga     720
agataggata gaaggacaaa gagcaagtta aaacccagca tggagaggag cacaaaaagg    780
ccacagacac tgctggtccc tgtgtctgag cctgcatgtt tgatggtgtc tggatgcaag    840 cagaagggt ggaagagctt gcctggagag atacagctgg gtcagtagga ctgggacagg     900
```

```
cagctggaga attgccatgt agatgttcat acaatcgtca aatcatgaag gctggaaaag    960
ccctccaaga tccccaagac caaccccaac ccacccaccg tgcccactgg ccatgtccct   1020
cagtgccaca tccccacagt tcttcatcac ctccagggac ggtgacccccc ccacctccgt   1080 gggcagctgt gccactgcag caccgctctt tggagaaggt aaatcttgct aaatccagcc   1140
cgaccctccc ctggcacaac gtaaggccat tatctctcat ccaactccag gacggagtca   1200
gtgagaatat t                                                         1211
```

<210> SEQ ID NO 4
<211> LENGTH: 243
<212> TYPE: DNA
<213> ORGANISM: Artificial sequence
<220> FEATURE:
<223> OTHER INFORMATION: HS4 core sequence
<220> FEATURE:
<221> NAME/KEY: misc_feature
<222> LOCATION: (1)..(6)
<223> OTHER INFORMATION: SacI site
<220> FEATURE:
<221> NAME/KEY: misc_feature
<222> LOCATION: (238)..(243)
<223> OTHER INFORMATION: HindIII site

<400> SEQUENCE: 4

```
gagctcacgg ggacagcccc ccccaaagc ccccagggat gtaattacgt ccctcccccg     60 ctaggggggca gcagcgagcc gcccggggct ccgctccggt ccggcgctcc ccccgcatcc   120
ccgagccggc agcgtgcggg gacagcccgg gcacggggaa ggtggcacgg gatcgctttc   180
ctctgaacgc ttctcgctgc tctttgagcc tgcagacacc tgggggatac ggggaaaaag   240
ctt                                                                  243
```

<210> SEQ ID NO 5
<211> LENGTH: 578
<212> TYPE: DNA
<213> ORGANISM: Artificial sequence
<220> FEATURE:
<223> OTHER INFORMATION: Gaussia luciferase with terminal HindIII and
      NotI sites
<220> FEATURE:
<221> NAME/KEY: misc_feature
<222> LOCATION: (1)..(6)
<223> OTHER INFORMATION: BamHI site
<220> FEATURE:
<221> NAME/KEY: misc_feature
<222> LOCATION: (571)..(578)
<223> OTHER INFORMATION: Not I site

<400> SEQUENCE: 5

```
ggatccgcca ccatgggagt caaagttctg tttgccctga tctgcatcgc tgtggccgag     60
gccaagccca ccgagaacaa cgaagacttc aacatcgtgg ccgtggccag caacttcgcg   120
accacggatc tcgatgctga ccgcgggaag ttgcccggca agaagctgcc gctggaggtg   180
ctcaaagagt tggaagccaa tgcccggaaa gctggctgca ccaggggctg tctgatctgc   240
ctgtcccaca tcaagtgcac gcccaagatg aagaagttca tcccaggacg ctgccacacc   300
tacgaaggcg acaaagagtc cgcacagggc ggcataggcg aggcgatcgt cgacattcct   360
gagattcctg ggttcaagga cttggagccc ttggagcagt tcatcgcaca ggtcgatctg   420
tgtgtggact gcacaactgg ctgcctcaaa gggcttgcca acgtgcagtg ttctgacctg   480
ctcaagaagt ggctgccgca acgctgtgcg acctttgcca gcaagatcca gggccaggtg   540
gacaagatca aggggccgg tggtgactaa gcggccgc                             578
```

<210> SEQ ID NO 6
<211> LENGTH: 585
<212> TYPE: DNA
<213> ORGANISM: Artificial sequence
<220> FEATURE:
<223> OTHER INFORMATION: IRES
<220> FEATURE:
<221> NAME/KEY: misc_feature
<222> LOCATION: (578)..(583)
<223> OTHER INFORMATION: MscI site

<400> SEQUENCE: 6

```
gcccctctcc ctccccccccc cctaacgtta ctggccgaag ccgcttggaa taaggccggt      60
gtgcgtttgt ctatatgtta ttttccacca tattgccgtc ttttggcaat gtgagggccc     120
ggaaacctgg ccctgtcttc ttgacgagca ttcctagggg tctttcccct ctcgccaaag     180
gaatgcaagg tctgttgaat gtcgtgaagg aagcagttcc tctggaagct tcttgaagac     240
aaacaacgtc tgtagcgacc ctttgcaggc agcggaaccc cccacctggc gacaggtgcc     300
tctgcggcca aaagccacgt gtataagata cacctgcaaa ggcggcacaa ccccagtgcc     360
acgttgtgag ttggatagtt gtggaaagag tcaaatggct ctcctcaagc gtattcaaca     420
aggggctgaa ggatgcccag aaggtacccc attgtatggg atctgatctg gggcctcggt     480
gcacatgctt tacatgtgtt tagtcgaggt taaaaaaacg tctaggcccc ccgaaccacg     540
gggacgtggt tttcctttga aaacacgat gataatatgg ccaca                      585
```

<210> SEQ ID NO 7
<211> LENGTH: 962
<212> TYPE: DNA
<213> ORGANISM: Artificial sequence
<220> FEATURE:
<223> OTHER INFORMATION: Delta24E1A

<400> SEQUENCE: 7

```
atgagacata ttatctgcca cggaggtgtt attaccgaag aaatggccgc cagtcttttg      60
gaccagctga tcgaagaggt actggctgat aatcttccac ctcctagcca ttttgaacca     120
cctaccctcc acgaactgta tgatttagac gtgacggccc ccgaagatcc caacgaggag     180
gcggtttcgc agattttttcc cgactctgta atgttggcgg tgcaggaagg gattgactta     240
ctcactttc cgccggcgcc cggttctccg gagccgcctc accttttccg gcagcccgag     300
cagccggagc agagagcctt gggtccggtt tctatgccaa accttgtacc ggaggtgatc     360
tttccaccca gtgacgacga ggatgaagag ggtgaggagt ttgtgttaga ttatgtggag     420
cacccggggc acggttgcag gtcttgtcat tatcaccgga ggaatacggg ggacccagat     480
attatgtgtt cgctttgcta tatgaggacc tgtggcatgt ttgtctacag taagtgaaaa     540
ttatgggcag tgggtgatag agtggtgggt ttggtgtggt aattttttt ttaattttta     600
cagttttgtg gtttaaagaa ttttgtattg tgatttttttt aaaaggtcct gtgtctgaac     660
ctgagcctga gccgagccca gaaccggagc ctgcaagacc tacccgccgt cctaaaatgg     720
cgcctgctat cctgagacgc ccgacatcac ctgtgtctag aatgcaat agtagtacgg     780
atagctgtga ctccggtcct tctaacacac ctccctgagat acaccggtg gtcccgctgt     840
gcccccattaa accagttgcc gtgagagttg gtgggcgtcg ccaggctgtg gaatgtatcg     900
aggacttgct taacgagcct gggcaacctt tggacttgag ctgtaaacgc cccaggccat     960
aa                                                                    962
```

```
<210> SEQ ID NO 8
<211> LENGTH: 289
<212> TYPE: PRT
<213> ORGANISM: Artificial sequence
<220> FEATURE:
<223> OTHER INFORMATION: Human E1A polypeptide sequence from Ad5 vector

<400> SEQUENCE: 8
```

Met Arg His Ile Ile Cys His Gly Gly Val Ile Thr Glu Glu Met Ala
1               5                   10                  15

Ala Ser Leu Leu Asp Gln Leu Ile Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
50                  55                  60

Ile Phe Pro Asp Ser Val Met Leu Ala Val Gln Gly Ile Asp Leu
65                  70                  75                  80

Leu Thr Phe Pro Pro Ala Pro Gly Ser Pro Gly Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Glu Glu Phe Val Leu
130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
        195                 200                 205

Met Ala Pro Ala Ile Leu Arg Arg Pro Thr Ser Pro Val Ser Arg Glu
210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255

Val Arg Val Gly Gly Arg Arg Gln Ala Val Glu Cys Ile Glu Asp Leu
            260                 265                 270

Leu Asn Glu Pro Gly Gln Pro Leu Asp Leu Ser Cys Lys Arg Pro Arg
        275                 280                 285

Pro

```
<210> SEQ ID NO 9
<211> LENGTH: 1676
<212> TYPE: DNA
<213> ORGANISM: Artificial sequence
<220> FEATURE:
<223> OTHER INFORMATION: Thymidine kinase from pWSTK3 construct

<400> SEQUENCE: 9
```
aacacgcaga tgcagtcggg gcggcgcggt cccaggtcca cttcgcatat taaggtgacg      60
cgtgtggcct cgaacaccga gcgaccctgc agcgacccgc ttaacagcgt caacagcgtg     120

```
ccgcagatct tggtggcgtg aaactcccgc acctcttcgg ccagcgcctt gtagaagcgc      180
gtatggcttc gtaccccggc catcaacacg cgtctgcgtt cgaccaggct gcgcgttctc      240
gcggccatag caaccgacgt acggcgttgc ccctcgccg gcagcaagaa gccacggaag      300
tccgcccgga gcagaaaatg cccacgctac tgcgggttta tatagacggt ccccacggga      360
tggggaaaac caccaccacg caactgctgg tggccctggg ttcgcgcgac gatatcgtct      420
acgtacccga ccgatgact tactgggggg tgctgggggc ttccgagaca atcgcgaaca      480
tctacaccac acaacaccgc ctcgaccagg gtgagatatc ggccggggac gcggcggtgg      540
taatgacaag cgcccagata acaatgggca tgccttatgc cgtgaccgac gccgttctgg      600
ctcctcatat cggggggggag gctgggagct cacatgcccc gccccggcc ctcaccctca      660 tcttcgaccg ccatcccatc gccgccctcc tgtgctaccc ggccgcgcgg taccttatgg      720
gcagcatgac ccccaggcc gtgctggcgt tcgtggccct catcccgccg accttgcccg      780
gcaccaacat cgtgcttggg gcccttccgg aggacagaca catcgaccgc ctggccaaac      840
gccagcgccc cggcgagcgg ctggacctgg ctatgctggc tgcgattcgc cgcgtttacg      900
ggctacttgc caatacggtg cggtatctgc agtgcggcgg gtcgtggcgg gaggactggg      960
gacagctttc ggggacggcc gtgccgcccc agggtgccga gccccagagc aacgcgggcc     1020
cacgacccca tatcggggac acgttattta ccctgtttcg ggccccgag ttgctggccc     1080 ccaacggcga cctgtataac gtgtttgcct gggccttgga cgtcttggcc aaacgcctcc     1140
gttccatgca cgtctttatc ctggattacg accaatcgcc cgccggctgc cgggacgccc     1200
tgctgcaact tacctccggg atggtccaga cccacgtcac caccccggc tccataccga     1260 cgatatgcga cctggcgcgc acgtttgccc gggagatggg ggaggctaac tgaaacacgg     1320
aaggagacaa taccggaagg aacccgcgct atgacggcaa taaaaagaca gaataaaacg     1380
cacgggtgtt gggtcgtttg ttcataaacg cggggttcgg tcccagggct ggcactctgt     1440 cgataccccca ccgagacccc attggggcca atacgcccgc gtttcttcct tttccccacc     1500 ccaccccca agttcgggtg aaggcccagg gctcgcagcc aacgtcgggg cggcaggccc     1560
tgccatagcc actggccccg tgggttaggg acggggtccc ccatgggaa tggttttatgg     1620 ttcgtggggg ttattatttt gggcgttgcg tggggtcagg tccacgaccc aagctt         1676
```

<210> SEQ ID NO 10
<211> LENGTH: 240
<212> TYPE: DNA
<213> ORGANISM: Artificial sequence
<220> FEATURE:
<223> OTHER INFORMATION: 3-prime untranslated region
<220> FEATURE:
<221> NAME/KEY: misc_feature
<222> LOCATION: (2)..(7)
<223> OTHER INFORMATION: XbaI site

<400> SEQUENCE: 10

```
atctagataa ctgatcataa tcagccatac cacatttgta gaggttttac ttgctttaaa       60
aaacctccca cacctccccc tgaacctgaa acataaaatg aatgcaattg ttgttgttaa      120
cttgtttatt gcagcttata atggttacaa ataaagcaat agcatcacaa atttcacaaa      180
taaagcattt ttttcactgc attctagttg tggtttgtcc aaactcatca atgtatctta      240
```

<210> SEQ ID NO 11
<211> LENGTH: 5786
<212> TYPE: DNA
<213> ORGANISM: Artificial sequence

```
<220> FEATURE:
<223> OTHER INFORMATION: Recombinant vector having
      2xins-INSM1p-2xNRSE-Delta24E1A-IRES-HSVtk-3-prime untranslated
      region
<220> FEATURE:
<221> NAME/KEY: misc_feature
<222> LOCATION: (1)..(6)
<223> OTHER INFORMATION: SacI site
<220> FEATURE:
<221> NAME/KEY: misc_feature
<222> LOCATION: (7)..(243)
<223> OTHER INFORMATION: First insulator core sequence
<220> FEATURE:
<221> NAME/KEY: misc_feature
<222> LOCATION: (244)..(486)
<223> OTHER INFORMATION: Second insulator core sequence
<220> FEATURE:
<221> NAME/KEY: misc_feature
<222> LOCATION: (509)..(2210)
<223> OTHER INFORMATION: INSM1 promoter
<220> FEATURE:
<221> NAME/KEY: misc_feature
<222> LOCATION: (2223)..(2244)
<223> OTHER INFORMATION: First nicotinic acetylcholine receptor neuronal
      restrictive silencer element
<220> FEATURE:
<221> NAME/KEY: misc_feature
<222> LOCATION: (2245)..(2266)
<223> OTHER INFORMATION: Second nicotinic acetylcholine receptor
      neuronal restrictive silencer element
<220> FEATURE:
<221> NAME/KEY: misc_feature
<222> LOCATION: (2285)..(3246)
<223> OTHER INFORMATION: Delta24E1A coding region
<220> FEATURE:
<221> NAME/KEY: misc_feature
<222> LOCATION: (3247)..(3831)
<223> OTHER INFORMATION: IRES
<220> FEATURE:
<221> NAME/KEY: misc_feature
<222> LOCATION: (3843)..(5518)
<223> OTHER INFORMATION: HSV-thymidine kinase coding region
<220> FEATURE:
<221> NAME/KEY: misc_feature
<222> LOCATION: (5519)..(5786)
<223> OTHER INFORMATION: 3-prime untranslated region

<400> SEQUENCE: 11
gagctcacgg ggacagcccc cccccaaagc ccccagggat gtaattacgt ccctcccccg       60 ctaggggca gcagcgagcc gcccggggct ccgctccggt ccggcgctcc ccccgcatcc       120
ccgagccggc agcgtgcggg gacagcccgg gcacggggaa ggtggcacgg gatcgctttc      180
ctctgaacgc ttctcgctgc tctttgagcc tgcagacacc tgggggatac ggggaaaaag     240
cttgagctca cggggacagc ccccccccaa agccccaggg gatgtaatta cgtccctccc     300
ccgctagggg gcagcagcga gccgcccggg gctccgctcc ggtccggcgc tcccccccgca    360 tccccgagcc ggcagcgtgc ggggacagcc cgggcacggg gaaggtggca cgggatcgct     420
ttcctctgaa cgcttctcgc tgctctttga gcctgcagac acctggggga tacggggaaa    480
aagcttgagc tcttacgcgt gctagcccaa agctttgcag aaaaatgttt ccttctcttt    540
caataaagtg acattttcct cacagcatat gacatttat gtggcttggc tatttgttcc    600
ccagtgttgg acgatcaggg ccactacgca ctcgtggggt tctctgccct gtcccccgaa   660
gattctgcct tttgtgtttc ctcggggctg ggctggacag aggatggagg caggcggcc    720 agtctgggtc caaacggaac ggcagcggag gtggggggtgg gggtggggggc ggggggaatc  780 ttcgctgttg tctcttcctg gtggcacagg ggaggcggct tgtcctctcg gaggcctcag    840
cctgcctcag agtacagatt gccccccctc ccccccgtcca gcacgcgtct cttttgcgtc   900
```

```
cagattggcc gcgaccggag ctcaatagca ggaggttaat ttccttcaca aaggtgaagg      960
gggcacggct ccgtggggc  tgcgccagac aggcagcccc tttatttcgc agcgccttga     1020
ttggagccct tgatttagca tctgatgtca accggcaaac aaaatgcccg ctcggaatga     1080
aaatgcatga ggccgcgcgg ggaggagaaa gccaacttca ctggggcgca cgaggccgac     1140
cgcgcgtttc gggcttcggc caactcgacc cggattaacc gagccttgga ccacgcggaa     1200
gctccgggcg gcctgggtcg gccccgccaa agatgccatt cccaagcctc caagaaccca     1260
aaagttcaga aattcacgtt cctctgggaa cccagcccag cccgcccgcg ctccaatccc     1320
gcgctttcgg gagactgaga aggccgtgcc aattccttct caaactcgaa agaaaccttc     1380
tctagccccg tgggcgcgcg gaggctgcga gcacaaacat cgcctcggc  cactgccaga     1440
aggccgggcc ccctgtccac acttggaacc ccggggaacc cttttgcttg gcctcttggg     1500
tccagcggcc catccgtcca aggtccgggc ggaggcgtcc ggaccctgct gctctctcgg     1560
attcttgttt atttcccaaa caccacgcgg acgcactgcg cctccgcaac gatctccccc     1620
gcaccgcccc ggcgcgcccc cgcccccacc caatcagcgc gcacaacttc ccctcggct     1680
ccggctcgcg gattgaaccc tcctgacata tttggggcca ttcttctcct tgttgctat     1740
tttgctagca acccgcgggt aatccccgcg cgggaggggg gcgtgcattg tcgcgctgat     1800
ggacgggccc atttggcggc tccgcgcccc ccggaggaga gacacaaagc ccaggcacgt     1860
gcgcctcccc atagagaagc agcagaccgt aagggaggc  ggggccgggc gtgtgcctgg     1920
accgggcggg gcggcggcgc cgggcggggc gaccaggggc gcgcgcgggg gccccgcgcc     1980
ctcaggtaca tctgccgcac ctaccggcg  accccgagt  cccggccccc ttttggccgc     2040
cccatcgccc tcccaccctg ccaggctgag gagctgcgga cgcgctgatt ggctccaggg     2100
gaagcgggag gcgagaacaa tggccccctc cccccgttaa aagggagcgg ctgccgggcc     2160
cggggacagg gacgcgcgtg cagggcgcag agctgggccg agccgtcgcc gggctcgagt     2220
cttcagcac  cacggacagc gctcttcagc accacggaca cgcgctcgcga tctaagttaa     2280
gcttatgaga catattatct gccacggagg tgttattacc gaagaaatgg ccgccagtct     2340
tttggaccag ctgatcgaag aggtactggc tgataatctt ccacctccta gccattttga     2400
accacctacc cttcacgaac tgtatgattt agacgtgacg gcccccgaag atcccaacga     2460
ggaggcggtt tcgcagattt ttcccgactc tgtaatgttg gcggtgcagg aagggattga     2520
cttactcact tttccgccgg cgcccggttc tccggagccg cctcacccttt cccggcagcc     2580
cgagcagccg gagcagagag ccttgggtcc ggtttctatg ccaaaccttg taccggaggt     2640
gatcttttcca cccagtgacg acgaggatga agagggtgag gagtttgtgt tagattatgt     2700
ggagcacccc gggcacggtt gcaggtcttg tcattatcac cggaggaata cggggggaccc     2760
agatattatg tgttcgcttt gctatatgag gacctgtggc atgtttgtct acagtaagtg     2820
aaaattatgg gcagtgggtg atagagtggt gggtttggtg tggtaatttt ttttttaatt     2880
tttacagttt tgtggtttaa agaattttgt attgtgattt ttttaaaagg tcctgtgtct     2940
gaacctgagc ctgagcccga gccagaaccg gagcctgcaa gacctacccg ccgtcctaaa     3000
atggcgcctg ctatcctgag acgcccgaca tcacctgtgt ctagagaatg caatagtagt     3060
acggatagct gtgactccgg tccttctaac acacctcctg agatacaccc ggtggtcccg     3120
ctgtgcccca ttaaaccagt tgccgtgaga gttggtgggc gtcgccaggc tgtggaatgt     3180
atcgaggact tgcttaacga gcctgggcaa cctttggact tgagctgtaa acgccccagg     3240
ccataagccc ctctccctcc ccccccccta acgttactgg ccgaagccgc ttggaataag     3300
```

```
gccggtgtgc gtttgtctat atgttatttt ccaccatatt gccgtctttt ggcaatgtga   3360
gggcccggaa acctggccct gtcttcttga cgagcattcc tagggtctt  tcccctctcg    3420
ccaaaggaat gcaaggtctg ttgaatgtcg tgaaggaagc agttcctctg gaagcttctt   3480
gaagacaaac aacgtctgta gcgacccttt gcaggcagcg aaccccccca cctggcgaca   3540
ggtgcctctg cggccaaaag ccacgtgtat aagatacacc tgcaaaggcg gcacaacccc   3600
agtgccacgt tgtgagttgg atagttgtgg aaagagtcaa atggctctcc tcaagcgtat   3660
tcaacaaggg gctgaaggat gcccagaagg taccccattg tatgggatct gatctggggc   3720
ctcggtgcac atgctttaca tgtgtttagt cgaggttaaa aaaacgtcta ggcccccga    3780
accacgggga cgtggttttc ctttgaaaaa cacgatgata atatgccac  aggatccttt    3840
cgaacacgca gatgcagtcg gggcggcgcg gtcccaggtc cacttcgcat attaaggtga   3900
cgcgtgtggc ctcgaacacc gagcgaccct gcagcgaccc gcttaacagc gtcaacagcg   3960
tgccgcagat cttggtggcg tgaaactccc gcacctcttc ggccagcgcc ttgtagaagc   4020
gcgtatggct tcgtaccccg gccatcaaca cgcgtctgcg ttcgaccagg ctgcgcgttc   4080
tcgcggccat agcaaccgac gtacggcgtt gcgccctcgc cggcagcaag aagccacgga   4140
agtccgcccg gagcagaaaa tgcccacgct actgcgggtt tatatagacg gtccccacgg   4200
gatgggaaa  accaccacca cgcaactgct ggtggccctg ggttcgcgcg acgatatcgt    4260
ctacgtaccc gagccgatga cttactggcg ggtgctgggg gcttccgaga caatcgcgaa   4320
catctacacc acacaacacc gcctcgacca gggtgagata tcggccgggg acgcggcggt   4380
ggtaatgaca agcgcccaga taacaatggg catgccttat gccgtgaccg acgccgttct   4440
ggctcctcat atcgggggg  aggctgggag ctcacatgcc ccgccccgg  ccctcaccct    4500
catcttcgac cgccatccca tcgccgccct cctgtgctac ccggccgcgc ggtaccttat   4560
gggcagcatg acccccagg  ccgtgctggc gttcgtggcc ctcatcccgc cgaccttgcc    4620
cggcaccaac atcgtgcttg ggcccttcc  ggaggacaga cacatcgacc gcctggccaa    4680
acgccagcgc cccggcgagc ggctggacct ggctatgctg gctgcgattc gccgcgttta   4740
cgggctactt gccaatacgg tgcggtatct gcagtgcggg gggtcgtggc gggaggactg   4800
gggacagctt tcggggacgg ccgtgccgcc ccagggtgcc gagccccaga gcaacgcggg   4860
cccacgaccc catatcgggg acacgttatt taccctgttt cgggccccg  agttgctggc    4920
ccccaacggc gacctgtata acgtgtttgc ctgggccttg gacgtcttgg ccaaacgcct   4980
ccgttccatg cacgtcttta tcctggatta cgaccaatcg cccgccggct gccgggacgc   5040
cctgctgcaa cttacctccg ggatggtcca gacccacgtc accaccccg  gctccatacc    5100
gacgatatgc gacctggcgc gcacgtttgc ccggagatg  ggggaggcta actgaaacac    5160
ggaaggagac aataccggaa ggaacccgcg ctatgacggc aataaaaaga cagaataaaa   5220
cgcacgggtg ttgggtcgtt tgttcataaa cgcggggttc ggtccagggg ctggcactct   5280
gtcgataccc caccgagacc ccattgggc  caatacgccc gcgtttcttc  cttttcccca    5340
ccccaccccc caagttcggg tgaaggccca gggctcgcag ccaacgtcgg ggcggcaggc   5400
cctgccatag ccactggccc cgtgggttag ggacggggtc cccatgggg  aatggtttat     5460
ggttcgtggg ggttattatt ttgggcgttg cgtggggtca ggtccacgac ccaagctttc   5520
tagagtcggg gcggccggcc gcttcgagca gacatgataa gatacattga tgagtttgga   5580
caaaccacaa ctagaatgca gtgaaaaaaa tgctttattt gtgaaatttg tgatgctatt   5640
```

```
gctttatttg taaccattat aagctgcaat aaacaagtta acaacaacaa ttgcattcat    5700
tttatgtttc aggttcaggg ggaggtgtgg gaggtttttt aaagcaagta aaacctctac    5760
aaatgtggta aaatcgataa ggatcc                                         5786
```

<210> SEQ ID NO 12
<211> LENGTH: 5775
<212> TYPE: DNA
<213> ORGANISM: Artificial sequence
<220> FEATURE:
<223> OTHER INFORMATION: Recombinant vector having the
      2xins-INSM1p-2xNRSE-Delta24E1A-IRES-HSVtk-3-prime untranslated
      region insert

<400> SEQUENCE: 12

```
gagctcacgg ggacagcccc cccccaaagc ccccagggat gtaattacgt ccctccccg       60 ctaggggggca gcagcgagcc gcccggggct ccgctccggt ccggcgctcc ccccgcatcc     120
ccgagccggc agcgtgcggg gacagcccgg gcacggggaa ggtggcacgg gatcgctttc     180
ctctgaacgc ttctcgctgc tctttgagcc tgcagacacc tggggatac ggggaaaaag      240 cttgagctca cggggacagc ccccccccaa agccccagg gatgtaatta cgtccctccc      300 cgctagggg gcagcagcga gccgcccggg gctccgctcc ggtccggcgc tccccccgca      360
tccccgagcc ggcagcgtgc ggggacagcc cgggcacggg gaaggtggca cgggatcgct     420
ttcctctgaa cgcttctcgc tgctctttga gcctgcagac acctggggga tacggggaaa    480
aagcttgagc tcttacgcgt gctagcccaa agctttgcag aaaatgtttt ccttctcttt    540
caataaagtg acattttcct cacagcatat gacattttat gtggcttggc tatttgttcc    600
ccagtgttgg acgatcaggg ccactacgca ctcgtgggt tctctgccct gtccccgaa       660 gattctgcct tttgtgtttc ctcggggctg ggctggacag aggatggagg caggcggccc    720
agtctgggtc caaacggaac ggcagcggag gtgggggtgg gggtggggc gggggggaatc    780 ttcgctgttg tctcttcctg gtggcacagg ggaggcggct tgtcctctcg gaggcctcag     840
cctgcctcag agtacagatt gccccccctc ccccgtcca gcacgcgtct cttttgcgtc     900
cagattggcc gcgaccggag ctcaatagca ggaggttaat ttccttcaca aaggtgaagg    960
gggcacggct ccgtggggc tgcgccagac aggcagcccc tttatttcgc agcgccttga   1020 ttggagcccct tgatttagca tctgatgtca accggcaaac aaaatgcccg ctcggaatga   1080
aaatgcatga ggccgcgcgg ggaggagaaa gccaacttca ctggggcgca cgaggccgac   1140
cgcgcgtttc gggcttcggc caactcgacc cggattaacc gagccttgga ccacgcggaa   1200 gctccggggcg gcctgggtcg gccccgccaa agatgccatt cccaagcctc caagaaccca  1260
aaagttcaga aattcacgtt cctctgggaa cccagcccag cccgcccgcg ctccaatccc   1320
gcgctttcgg gagactgaga aggccgtgcc aattccttct caaactcgaa agaaaccttc  1380
tctagccccg tgggcgcgcg gaggctgcga gcacaaacat cgcccctcggc cactgccaga  1440 aggccgggcc ccctgtccac acttggaacc ccggggaacc cttttgcttg gcctcttggg   1500
tccagcggcc catccgtcca aggtccgggc ggaggcgtcc ggaccctgct gctctctcgg    1560
attcttgttt atttcccaaa caccacgcgg acgcactgcg cctccgcaac gatctccccc    1620
gcaccgcccc ggcgcgcccc cgcccccacc caatcagcgc gcacaacttc cccctcggct    1680
ccggctcgcg gattgaaccc tcctgacata tttggggcca ttcttctcct ttgttgctat    1740
tttgctagcg acccgcgggt aatccccgcg cgggaggggg gcgtgcattg tcgcgctgat    1800
ggacgggccc atttggcggc tccgcgcccc ccggaggaga gacacaaagc ccaggcacgt    1860
```

```
gcgcctcccc atagagaagc agcagaccgt gaagggaggc ggggccgggc gtgtgcctgg    1920
accgggcggg gcggcggcgc cgggcggggc gaccaggggc gcgcgcgggg gccccgcgcc    1980
ctcaggtaca tctgccgcac ctaccgggcg accccgagt  cccggccccc ttttggccgc    2040
cccatcgccc tcccaccctg ccaggctgag gagctgcgga cgcgctgatt ggctccaggg    2100
gaagcgggag gcgagaacaa tggccccctc ccccgttaa  aagggagcgg ctgccgggcc    2160
cggggacagg gacgcgcgtg cagggcgcag agctgggccg agccgtcgcc gggctcgagt    2220 cttcagcac  cacggacagc gctcttcagc accacggaca gcgctcgcga tctaagttaa    2280
gcttatgaga catattatct gccacggagg tgttattacc gaagaaatgg ccgccagtct    2340
tttggaccag ctgatcgaag aggtactggc tgataatctt ccacctccta gccattttga    2400
accacctacc cttcacgaac tgtatgattt agacgtgacg gccccgaag  atcccaacga    2460 ggaggcggtt tcgcagattt ttcccgactc tgtaatgttg gcggtgcagg aagggattga    2520
cttactcact tttcgccgg  cgccggttc  tccggagccg cctcacccttt cccgcagcc    2580 cgagcagccg gagcagagag ccttgggtcc ggtttctatg ccaaaccttg taccggaggt    2640
gatctttcca cccagtgacg acgaggatga agagggtgag gagtttgtgt tagattatgt    2700
ggagcacccc gggcacggtt gcaggtcttg tcattatcac cggaggaata cggggaccc    2760 agatattatg tgttcgcttt gctatatgag gacctgtggc atgtttgtct acagtaagtg    2820
aaaattatgg gcagtgggtg atagagtggt gggtttggtg tggtaatttt ttttttaatt    2880
tttacagttt tgtggtttaa agaattttgt attgtgattt ttttaaaagg tcctgtgtct    2940
gaacctgagc ctgagcccga gccagaaccg gagcctgcaa gacctacccg ccgtcctaaa    3000
atggcgcctg ctatcctgag acgcccgaca tcacctgtgt ctagagaatg caatagtagt    3060
acggatagct gtgactccgg tccttctaac acacctcctg agatacaccc ggtggtcccg    3120
ctgtgcccca ttaaaccagt tgccgtgaga gttggtgggc gtcgccaggc tgtggaatgt    3180
atcgaggact tgcttaacga gcctgggcaa cctttggact tgagctgtaa acgccccagg    3240
ccataagccc ctctccctcc ccccccccta acgttactgg ccgaagccgc ttggaataag    3300
gccggtgtgc gtttgtctat atgttatttt ccaccatatt gccgtctttt ggcaatgtga    3360
gggcccggaa acctgcccct gtcttcttga cgagcattcc tagggtctt  tcccctctcg    3420 ccaaaggaat gcaaggtctg ttgaatgtcg tgaaggaagc agttcctctg gaagcttctt    3480
gaagacaaac aacgtctgta gcgacccttt gcaggcagcg gaaccccca  cctggcgaca    3540 ggtgcctctg cggccaaaag ccacgtgtat aagatacacc tgcaaaggcg gcacaaccccc   3600 agtgccacgt tgtgagttgg atagttgtgg aaagagtcaa atggctctcc tcaagcgtat    3660
tcaacaaggg gctgaaggat gcccagaagg taccccattg tatgggatct gatctggggc    3720
ctcggtgcac atgctttaca tgtgtttagt cgaggttaaa aaaacgtcta ggccccccga    3780
accacgggga cgtggttttc ctttgaaaaa cacgatgata tatggccac  aaacacgcag    3840 atgcagtcgg ggcggcgcgg tcccaggtcc acttcgcata ttaaggtgac gcgtgtggcc    3900
tcgaacaccg agcgaccctg cagcgacccg cttaacagcg tcaacagcgt gccgcagatc    3960
ttggtggcgt gaaactcccg cacctcttcg gccagcgcct tgtagaagcg cgtatggctt    4020
cgtaccccgg ccatcaacac gcgtctgcgt tcgaccaggc tgcgcgttct cgcggccata    4080
gcaaccgacg tacggcgttg cgccctcgcc ggcagcaaga agccacgaa  gtccgcccgg    4140 agcagaaaat gcccacgcta ctgcgggttt atatagacgg tccccacggg atggggaaaa    4200
```

```
ccaccaccac gcaactgctg gtggccctgg gttcgcgcga cgatatcgtc tacgtacccg    4260
agccgatgac ttactggcgg gtgctggggg cttccgagac aatcgcgaac atctacacca    4320
cacaacaccg cctcgaccag ggtgagatat cggccggga cgcggcggtg gtaatgacaa    4380
gcgcccagat aacaatgggc atgccttatg ccgtgaccga cgccgttctg gctcctcata    4440
tcggggggga ggctgggagc tcacatgccc cgcccccggc cctcaccctc atcttcgacc    4500
gccatcccat cgccgccctc ctgtgctacc cggccgcgcg gtaccttatg ggcagcatga    4560
cccccccaggc cgtgctggcg ttcgtggccc tcatcccgcc gaccttgccc ggcaccaaca    4620
tcgtgcttgg ggcccttccg gaggacagac acatcgaccg cctggccaaa cgccagcgcc    4680
ccggcgagcg gctggacctg gctatgctgg ctgcgattcg ccgcgtttac gggctacttg    4740
ccaatacggt gcggtatctg cagtgcggcg ggtcgtggcg ggaggactgg ggacagcttt    4800
cggggacggc cgtgccgccc cagggtgccg agccccagag caacgcgggc ccacgacccc    4860
atatcgggga cacgttattt accctgtttc gggcccccga gttgctggcc ccaacggcg    4920
acctgtataa cgtgtttgcc tgggccttgg acgtcttggc caaacgcctc cgttccatgc    4980
acgtctttat cctggattac gaccaatcgc ccgccggctg ccgggacgcc ctgctgcaac    5040
ttacctccgg gatggtccag acccacgtca ccaccccgg ctccataccg acgatatgcg    5100
acctggcgcg cacgtttgcc cgggagatgg gggaggctaa ctgaaacacg aaggagaca    5160
ataccggaag gaacccgcgc tatgacggca ataaaaagac agaataaaac gcacgggtgt    5220
tgggtcgttt gttcataaac gcggggttcg gtcccagggc tggcactctg tcgataccc    5280
accgagaccc cattggggcc aatacgcccg cgtttcttcc ttttccccac cccaccccc    5340
aagttcgggt gaaggcccag ggctcgcagc caacgtcggg gcggcaggcc ctgccatagc    5400
cactggcccc gtgggttagg gacggggtcc cccatgggga atggtttatg gttcgtgggg    5460
gttattattt tgggcgttgc gtggggtcag gtccacgacc caagctttct agagtcgggg    5520
cggccggccg cttcgagcag acatgataag atacattgat gagtttggac aaaccacaac    5580
tagaatgcag tgaaaaaaat gctttatttg tgaaatttgt gatgctattg ctttatttgt    5640
aaccattata agctgcaata aacaagttaa caacaacaat tgcattcatt ttatgtttca    5700
ggttcagggg gaggtgtggg aggttttta aagcaagtaa aacctctaca aatgtggtaa    5760
aatcgataag gatcc                                                    5775
```

<210> SEQ ID NO 13
<211> LENGTH: 3533
<212> TYPE: DNA
<213> ORGANISM: Artificial sequence
<220> FEATURE:
<223> OTHER INFORMATION: Recombinant vector having a
      2xins-INSM1p-2xNRSE-Delta24E1A-3-prime untranslated region

<400> SEQUENCE: 13

```
gagctcacgg ggacagcccc ccccaaagc ccccagggat gtaattacgt ccctcccccg       60
ctaggggca gcagcgagcc gcccggggct ccgctccggt ccggcgctcc ccccgcatcc      120
ccgagccggc agcgtgcggg gacagcccgg gcacggggaa ggtggcacgg gatcgctttc     180
ctctgaacgc ttctcgctgc tctttgagcc tgcagacacc tggggatac ggggaaaaag      240
cttgagctca cggggacagc cccccccaa agccccagg gatgtaatta cgtccctccc       300
ccgctagggg gcagcagcga gccgcccggg gctccgctcc ggtccggcgc tcccccgca      360
tccccgagcc ggcagcgtgc gggacagcc cgggcacggg gaaggtggca cgggatcgct      420
```

```
ttcctctgaa cgcttctcgc tgctctttga gcctgcagac acctggggga tacgggaaa       480 aagcttgagc tcttacgcgt gctagcccaa agctttgcag aaaaatgttt ccttctcttt       540
caataaagtg acattttcct cacagcatat gacattttat gtggcttggc tatttgttcc       600
ccagtgttgg acgatcaggg ccactacgca ctcgtgggt tctctgccct gtcccccgaa        660
gattctgcct tttgtgtttc ctcggggctg ggctggacag aggatggagg caggcggccc       720
agtctgggtc caaacggaac ggcagcgag gtggggtgg ggtgggggc gggggaatc          780 ttcgctgttg tctcttcctg gtggcacagg ggaggcggct tgtcctctcg gaggcctcag       840
cctgcctcag agtacagatt gcccccctc ccccgtcca gcacgcgtct cttttgcgtc         900
cagattggcc gcgaccggag ctcaatagca ggaggttaat ttccttcaca aaggtgaagg      960
gggcacggct ccgtggggc tgcgccagac aggcagcccc tttatttcgc agcgccttga       1020
ttggagccct tgatttagca tctgatgtca accggcaaac aaaatgcccg ctcggaatga     1080
aaatgcatga ggccgcgcgg ggaggagaaa gccaacttca ctgggcgca cgaggccgac      1140 cgcgcgtttc gggcttcggc caactcgacc cggattaacc gagccttgga ccacgcgaa       1200 gctccgggcg gcctgggtcg gccccgccaa agatgccatt cccaagcctc caagaaccca    1260
aaagttcaga aattcacgtt cctctgggaa cccagcccag cccgcccgcg ctccaatccc      1320 gcgcttcgg gagactgaga aggccgtgcc aattccttct caaactcgaa agaaaccttc       1380
tctagccccg tgggcgcgcg gaggctgcga gcacaaacat cgcccttcggc cactgccaga   1440 aggccgggcc ccctgtccac acttggaacc ccggggaacc cttttgcttg gcctcttggg      1500
tccagcggcc catccgtcca aggtccgggc ggaggcgtcc ggaccctgct gctctctcgg     1560
attcttgttt atttcccaaa caccacgcgg acgcactgcg cctccgcaac gatctccccc       1620
gcaccgcccc ggcgcgcccc cgcccccacc caatcagcgc gcacaacttc cccctcggct     1680
ccggctcgcg gattgaaccc tcctgacata tttggggcca ttcttctcct ttgttgctat        1740
tttgctagcg acccgcgggt aatccccgcg cgggagggg gcgtgcattg tcgcgctgat     1800
ggacgggccc atttggcggc tccgcgcccc ccggaggaga gacacaaagc ccaggcacgt     1860
gcgcctcccc atagagaagc agcagaccgt gaagggaggc ggggccgggc gtgtgcctgg      1920
accgggcggg gcggcggcgc cgggcggggc gaccagggc gcgcgcgggg gccccgcgcc    1980
ctcaggtaca tctgccgcac ctaccggcg accccgagt cccggcccc ttttggccgc         2040 cccatcgccc tcccacccctg ccaggctgag gagctgcgga cgcgctgatt ggctccaggg    2100
gaagcgggag gcgagaacaa tggccccctc ccccgttaa agggagcgg ctgccgggcc      2160 cggggacagg gacgcgcgtg cagggcgcag agctgggccg agccgtcgcc gggctcgagt     2220 cttcagcac cacggacagc gctcttcagc accacggaca cgctcgcga tctaagttaa       2280 gcttatgaga catattatct gccacggagg tgttattacc gaagaaatgg ccgccagtct      2340
tttggaccag ctgatcgaag aggtactggc tgataatctt ccacctccta gccattttga      2400
accacctacc cttcacgaac tgtatgattt agacgtgacg gccccgaag atcccaacga      2460 ggaggcggtt tcgcagattt ttcccgactc tgtaatgttg gcggtgcagg aagggattga     2520
cttactcact tttccgccgg cgcccggttc tcctgagccg cctcacctt ccggcagcc        2580 cgagcagccg gagcagagag ccttgggtcc ggtttctatg ccaaaccttg taccggaggt      2640
gatctttcca cccagtgacg acgaggatga agagggtgag gagtttgtgt tagattatgt      2700
ggagcacccc gggcacggtt gcaggtcttg tcattatcac cggaggaata cggggaccc      2760 agatattatg tgttcgcttt gctatatgag gacctgtggc atgtttgtct acagtaagtg     2820
```

```
aaaattatgg gcagtgggtg atagagtggt gggtttggtg tggtaatttt ttttttaatt      2880
tttacagttt tgtggtttaa agaattttgt attgtgattt ttttaaaagg tcctgtgtct      2940
gaacctgagc ctgagcccga gccagaaccg gagcctgcaa gacctacccg ccgtcctaaa      3000
atggcgcctg ctatcctgag acgcccgaca tcacctgtgt ctagagaatg caatagtagt      3060
acggatagct gtgactccgg tccttctaac acacctcctg agatacaccc ggtggtcccg      3120
ctgtgcccca ttaaaccagt tgccgtgaga gttggtgggc gtcgccaggc tgtggaatgt      3180
atcgaggact tgcttaacga gcctgggcaa cctttggact tgagctgtaa acgccccagg      3240
ccataaaggt ccacgaccca agctttctag agtcggggcg gccggccgct tcgagcagac      3300
atgataagat acattgatga gtttggacaa accacaacta gaatgcagtg aaaaaaatgc      3360
tttatttgtg aaatttgtga tgctattgct ttatttgtaa ccattataag ctgcaataaa      3420
caagttaaca acaacaattg cattcatttt atgtttcagg ttcaggggga ggtgtgggag      3480
gttttttaaa gcaagtaaaa cctctacaaa tgtggtaaaa tcgataagga tcc            3533
```

<210> SEQ ID NO 14
<211> LENGTH: 3149
<212> TYPE: DNA
<213> ORGANISM: Artificial sequence
<220> FEATURE:
<223> OTHER INFORMATION: Recombinant vector having a 2xins-INSM1p-
      2xNRSE-Gaussia luciferase-3-prime untranslated region <400> SEQUENCE: 14

```
gagctcacgg ggacagcccc cccccaaagc ccccagggat gtaattacgt ccctcccccg        60 ctaggggca gcgcgagcc gcccggggct ccgctccggt ccggcgctcc ccccgcatcc         120
ccgagccggc agcgtgcggg gacagcccgg gcacggggaa ggtggcacgg gatcgctttc       180
ctctgaacgc ttctcgctgc tctttgagcc tgcagacacc tgggggatac ggggaaaaag       240
cttgagctca cggggacagc ccccccccaa agccccagg gatgtaatta cgtccctccc        300
ccgctagggg gcagcagcga gcccggggct cccgctccgg tccggccgcc gtccccccgca      360 tccccgagcc ggcagcgtgc ggggacagcc cgggcacggg gaaggtggca cgggatcgct       420
ttcctctgaa cgcttctcgc tgctctttga gcctgcagac acctggggga tacggggaaa       480
aagcttgagc tcttacgcgt gctagcccaa agctttgcag aaaaatgttt ccttctcttt       540
caataaagtg acattttcct cacagcatat gacatttat gtggcttggc tatttgttcc       600
ccagtgttgg acgatcaggg ccactacgca ctcgtggggt tctctgccct gtccccgaa       660 gattctgcct tttgtgtttc ctcggggctg ggctggacag aggatggagg caggcggccc      720
agtctgggtc caaacggaac ggcagcgag gtgggggtgg gggtgggggc gggggaatc        780 ttcgctgttg tctcttcctg gtggcacagg ggaggcggct tgtcctctcg gaggcctcag      840
cctgcctcag agtacagatt gccccccctc ccccgtcca gcacgcgtct cttttgcgtc       900
cagattggcc gcgaccggag ctcaatagca ggaggttaat ttccttcaca aaggtgaagg      960
gggcacggct ccgtgggggc tgcgccagac aggcagcccc tttatttcgc agcgccttga     1020
ttggagccct tgatttagca tctgatgtca accggcaaac aaaatgcccg ctcggaatga     1080
aaatgcatga ggccgcgcgg ggaggagaaa gccaacttca ctggggcgca cgaggccgac     1140
cgcgcgtttc gggcttcggc caactcgacc cggattaacc gagccttgga ccacgcggaa     1200
gctccgggcg gcctgggtcg gccccgccaa agatgccatt cccaagcctc caagaaccca     1260
aaagttcaga aattcacgtt cctctgggaa cccagcccag cccgcccgcg ctccaatccc     1320
```

-continued

```
gcgctttcgg gagactgaga aggccgtgcc aattccttct caaactcgaa agaaaccttc    1380
tctagccccg tgggcgcgcg gaggctgcga gcacaaacat cgccctcggc cactgccaga    1440
aggccgggcc ccctgtccac acttggaacc ccggggaacc cttttgcttg gcctcttggg    1500
tccagcggcc catccgtcca aggtccgggc ggaggcgtcc ggaccctgct gctctctcgg    1560
attcttgttt atttcccaaa caccacgcgg acgcactgcg cctccgcaac gatctccccc    1620
gcaccgcccc ggcgcgcccc cgcccccacc caatcagcgc gcacaacttc ccctcggct    1680 ccggctcgcg gattgaaccc tcctgacata tttggggcca ttcttctcct tgttgctat     1740 tttgctagcg acccgcgggt aatccccgcg cgggaggggg gcgtgcattg tcgcgctgat    1800
ggacgggccc atttggcggc tccgcgcccc ccggaggaga gacacaaagc ccaggcacgt    1860
gcgcctcccc atagagaagc agcagaccgt gaagggaggc ggggccgggc gtgtgcctgg    1920
accgggcggg gcggcggcgc cgggcggggc gaccagggc gcgcgcgggg ccccgcgcc     1980 ctcaggtaca tctgccgcac ctaccggcg accccgagt cccggccccc ttttggccgc      2040
cccatcgccc tcccacccctg ccaggctgag gagctgcgga cgcgctgatt ggctccaggg   2100
gaagcgggag gcgagaacaa tggccccctc ccccgttaa aagggagcgg ctgccgggcc    2160
cggggacagg gacgcgcgtg cagggcgcag agctgggccg agccgtcgcc gggctcgagt    2220
ctttcagcac cacggacagc gctcttcagc accacggaca gcgctcgcga tctaagttaa    2280
gcttggatcc gccaccatgg gagtcaaagt tctgtttgcc ctgatctgca tcgctgtggc    2340
cgaggccaag cccaccgaga acaacgaaga cttcaacatc gtggccgtgg ccagcaactt    2400
cgcgaccacg gatctcgatg ctgaccgcgg gaagttgccc ggcaagaagc tgccgctgga    2460
ggtgctcaaa gagttggaag ccaatgcccg gaaagctggc tgcaccaggg gctgtctgat    2520
ctgcctgtcc cacatcaagt gcacgcccaa gatgaagaag ttcatcccag gacgctgcca    2580
cacctacgaa ggcgacaaag agtccgcaca gggcggcata ggcgaggcga tcgtcgacat    2640
tcctgagatt cctgggttca aggacttgga gcccttggag cagttcatcg cacaggtcga    2700
tctgtgtgtg gactgcacaa ctggctgcct caaagggctt gccaacgtgc agtgttctga    2760
cctgctcaag aagtggctgc cgcaacgctg tgcgaccttt gccagcaaga tccagggcca    2820
ggtggacaag atcaaggggg ccggtggtga ctaagcggcc gcaggtccac gacccaagct    2880
ttctagagtc ggggcggccg gccgcttcga gcagacatga taagatacat tgatgagttt    2940
ggacaaacca caactagaat gcagtgaaaa aaatgcttta tttgtgaaat ttgtgatgct    3000
attgctttat ttgtaaccat tataagctgc aataaacaag ttaacaacaa caattgcatt    3060
cattttatgt ttcaggttca gggggaggtg tgggaggttt tttaaagcaa gtaaaacctc    3120
tacaaatgtg gtaaaatcga taaggatcc                                     3149
```

TUMOR-SPECIFIC ADENOVIRUS VECTORS AND THERAPEUTIC USES

CROSS-REFERENCE TO RELATED APPLICATION

This application is the 35 U.S.C. § 371 national stage application of PCT Application No. PCT/US2016/059382, filed Oct. 28, 2016, where the PCT claims priority to and the benefit of U.S. Provisional Application 62/247,229, entitled "TUMOR-SPECIFIC ADENOVIRUS VECTORS AND THERAPEUTIC USES" filed on Oct. 28, 2015, the entireties of which are herein incorporated by reference.

SEQUENCE LISTING

This application contains a sequence listing filed in electronic form as an ASCII.txt file entitled "2222272100_ST25" created on Oct. 18, 2016. The content of the sequence listing is incorporated herein in its entirety.

TECHNICAL FIELD

The present disclosure is generally related to compositions and methods for enhancing tumor-specific gene expression from a viral vector. The present disclosure is also generally related to methods of inhibiting the proliferation of tumor cells, and especially of insulinoma cells, or their imaging.

BACKGROUND

Insulinoma-associated 1 (INSM1) is a transcriptional repressor protein that is required for the development of the endocrine pancreas, adrenal gland, basal neuronal progenitor cells in the neocortex, and the monoaminergic neurons in the hindbrain (Lan & Breslin (2009) *FASEB J.* 23: 2024-2033). INSM1 expression is restricted to early fetal development in neuronal and endocrine tissues (Breslin et al., (2003) *J. Biol. Chem.* 278: 38991-38997; Duggan et al., (2008) *J. Comp Neurol.* 507: 1497-1520; Goto et al., (1992) *J. Biol. Chem.* 267: 15252-15257; Mellitzer et al., (2006) *EMBO J.* 25: 1344-1352; Xie et al., (2002) *Genomics* 80: 54-61). One striking feature of the INSM1 mRNA is despite its absence in normal adult tissues, it is strongly expressed in tumors of neuroendocrine origin such as small cell lung carcinoma (SCLC), medullablastoma, neuroblastoma, medullary thyroid carcinoma, insulinoma, retinoblastoma, pheochromocytoma, and pituitary tumors (Goto et al., (1992) *J. Biol. Chem.* 267: 15252-15257; Lan et al., (1993) *Cancer Res.* 53: 4169-4171; Taniwaki et al., (2006) *Int. J. Oncol.* 29: 567-575). Using a transgenic animal model and in vitro reporter gene assays, the spatial and temporal expression of INSM1 has been demonstrated to be regulated by the 5' 1.7 kilobase pair promoter region (Breslin et al., (2003) *J. Biol. Chem.* 278: 38991-38997; Li et al., (1997) *Biochem. Biophys. Res. Commun.* 236: 776-781). The 1.7 kbp promoter region has been linked to a suicide gene for delivery into tumor cells. The ability of the INSM1 promoter to drive expression of the herpes simplex virus thymidine kinase gene selectively has been tested in small cell lung cancer (SCLC) cells and in pediatric brain tumors (Pedersen et al., (2006) *Cancer Gene Ther.* 13: 375-384; Wang et al., (2009) *Hum. Gene Ther.* 20: 1308-1318; see also, U.S. Patent Application Publication No. 2005/0037445). Adenoviral vectors are one of the most widely exploited viral delivery systems for gene therapy due to their ability to infect a wide range of host cells and the minimal risk associated with the use of a non-replicating form of the virus. The adenovirus genome is easily manipulated and with the deletion of the E1 and E3 genes allows for the incorporation of up to 7.5 kilobase pairs of exogenous sequence. However, one major drawback of adenovirus is host mediated immunity to the virus. In addition, due to the high liver transduction efficiency following intravenous delivery of adenovirus, the liver is most susceptible to toxic side effects.

SUMMARY

The compositions and methods of the disclosure are suitable for the treatment and/or diagnosis of human neuroendocrine tumors using a combination of a first expression construct comprising the nucleic acid sequence from the human insulinoma-associated 1 (INSM1) promoter, one or more elements selected from neuron restrictive silencer elements and insulator elements, and a suicide or toxin-encoding element for treatment of tumors and/or a reporter gene for visualization or detection. A second expression construct comprises a modified adenovirus E1A region that in combination with the first construct results in enhanced tumor-specific expression of the toxin polypeptide or the reporter gene. The construct may be linked directly with a reporter gene for diagnosis of neuroendocrine tumors.

One aspect of the disclosure, therefore, encompasses embodiments of a neuroendocrine tumor-specific viral expression vector whose genome comprises: (a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8; (b) an insulator region upstream from said promoter, wherein said insulator region comprises an insulator element or a tandem pair of core insulator elements; (c) a pair of tandem neuronal restrictive silencer elements (NRSE) downstream from said promoter; (d) an IRES element operatively linked upstream of one or more open reading frame nucleotide sequences encoding at least one of a polypeptide toxin lethal or conditionally lethal to cells in which the toxin is expressed and a secreted bioluminescent reporter molecule; and (e) at least one nucleotide sequence encoding a 3'-untranslated region, wherein: (i) said insulator region is adapted to block the influence of viral regulatory elements on the transcription within mammalian cells of said one or more nucleotide sequences, but not to affect the influence of the INSM1 promoter or the influence of the neuronal restrictive silencer elements on the transcription of said one or more polypeptide encoding nucleotide sequences; (ii) said INSM1 promoter is adapted to cause the selective transcription of said one or more nucleotide sequences in tumor cells of neuroendocrine origin; and (iii) said pair of tandem neuronal restrictive silencer elements are operatively linked to the INSM1 promoter, and are adapted to selectively repress the transcription of said one or more nucleotide sequences in non-neuronal cells.

Another aspect of the disclosure encompasses embodiments of a composition comprising a first neuroendocrine tumor-specific viral expression vector whose genome comprises: (a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8; (b) an insulator region upstream from said promoter, wherein said insulator region comprises an insulator element or a tandem pair of core insulator elements; (c) a pair of tandem neuronal restrictive silencer elements (NRSE) downstream from said promoter; (d) an IRES element operatively linked upstream of one or more open reading frame nucleotide sequences encoding at least one of a polypeptide toxin lethal or conditionally lethal to cells in which the toxin is expressed and a secreted bioluminescent reporter molecule; and (e) at least one nucleotide sequence encoding a 3'-untranslated region, wherein: (i) said insulator region is adapted to block the influence of viral regulatory elements on the transcription within mammalian cells of said one or more nucleotide sequences, but not to affect the influence of the INSM1 promoter or the influence of the neuronal restrictive silencer elements on the transcription of said one or more polypeptide encoding nucleotide sequences; (ii) said INSM1 promoter is adapted to cause the selective transcription of said one or more nucleotide sequences in tumor cells of neuroendocrine origin; and (iii) said pair of tandem neuronal restrictive silencer elements are operatively linked to the INSM1 promoter, and are adapted to selectively repress the transcription of said one or more nucleotide sequences in non-neuronal cells.

In some embodiments of this aspect of the disclosure, the composition can further comprise a second neuroendocrine tumor-specific viral expression vector, the genome of said second viral expression vector comprising: (a) a human Insulinoma-associated 1 promoter (INSM1p) operatively linked to a nucleotide sequence encoding a polypeptide toxin lethal or conditionally lethal to cells in which the toxin is expressed and a polypeptide reporter molecule; (b) an insulator region upstream from said promoter, wherein said insulator region comprises an insulator element or a tandem pair of core insulator elements; (c) a pair of tandem neuronal restrictive silencer elements downstream from said promoter; and (d) a nucleotide sequence encoding a 3'-untranslated region, wherein: (i) said second viral expression vector is competent to infect at least some mammalian cells; (ii) said insulator region is adapted to block the influence of viral regulatory elements on the transcription within mammalian cells of said one or more nucleotide sequences, but not to affect the influence of said promoter or the influence of said neuronal restrictive silencer elements on the transcription of said one or more nucleotide sequences; (iii) said INSM1 promoter is adapted to cause the selective transcription of said one or more nucleotide sequences in tumor cells of neuroendocrine origin; and (iv) said tandem neuronal restrictive silencer elements are operatively linked to said promoter, and are adapted to selectively repress the transcription of said one or more nucleotide sequences in non-neuronal cells; wherein the level of expression of the polypeptide toxin or the polypeptide reporter molecule from the combination of the first and second vectors in a recipient cell is synergistically greater compared to expression from the first or second vector alone.

Yet another aspect of the disclosure encompasses embodiments of a method of increasing the tumor-specific expression of a polypeptide from a viral vector, said method comprising delivering to a neuroendocrine tumor cell or tumor a first neuroendocrine tumor-specific viral expression vector whose genome comprises: (a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8; (b) an insulator region upstream from said promoter, wherein said insulator region comprises an insulator element or a tandem pair of core insulator elements; (c) a pair of tandem neuronal restrictive silencer elements (NRSE) downstream from said promoter; (d) an IRES element operatively linked upstream of one or more open reading frame nucleotide sequences encoding at least one of a polypeptide toxin lethal or conditionally lethal to cells in which the toxin is expressed and a secreted bioluminescent reporter molecule; and (e) at least one nucleotide sequence encoding a 3'-untranslated region wherein: (i) said insulator region is adapted to block the influence of viral regulatory elements on the transcription within mammalian cells of said one or more nucleotide sequences, but not to affect the influence of the INSM1 promoter or the influence of the neuronal restrictive silencer elements on the transcription of said one or more polypeptide encoding nucleotide sequences; (ii) said INSM1 promoter is adapted to cause the selective transcription of said one or more nucleotide sequences in tumor cells of neuroendocrine origin; and (iii) said pair of tandem neuronal restrictive silencer elements are operatively linked to the INSM1 promoter, and are adapted to selectively repress the transcription of said one or more nucleotide sequences in non-neuronal cells.

In some embodiments of this aspect of the disclosure, the method can further comprise delivering to the neuroendocrine tumor cell or tumor a second neuroendocrine tumor-specific viral expression vector, the genome of said second viral expression vector comprising: (a) a human Insulinoma-associated 1 promoter (INSM1p) operatively linked to a nucleotide sequence encoding a polypeptide toxin lethal or conditionally lethal to cells in which the toxin is expressed and a polypeptide reporter molecule; (b) an insulator region upstream from said promoter, wherein said insulator region comprises an insulator element or a tandem pair of core insulator elements; (c) a pair of tandem neuronal restrictive silencer elements downstream from said promoter; and (d) a nucleotide sequence encoding a 3'-untranslated region, wherein: (i) said second viral expression vector is competent to infect at least some mammalian cells; (ii) said insulator region is adapted to block the influence of viral regulatory elements on the transcription within mammalian cells of said one or more nucleotide sequences, but not to affect the influence of said promoter or the influence of said neuronal restrictive silencer elements on the transcription of said one or more nucleotide sequences; (iii) said INSM1 promoter is adapted to cause the selective transcription of said one or more nucleotide sequences in tumor cells of neuroendocrine origin; and (iv) said tandem neuronal restrictive silencer elements are operatively linked to said promoter, and are adapted to selectively repress the transcription of said one or more nucleotide sequences in non-neuronal cells; wherein the level of expression of the at least one of the polypeptide toxin and the polypeptide reporter molecule from the combination of the first and second vectors in the recipient cell or tumor is synergistically greater compared to expression from the first or second vector alone.

In some embodiments of this aspect of the disclosure, the first and second neuroendocrine tumor-specific viral expression vectors can each comprise a nucleotide sequence encoding a polypeptide toxin and wherein, if said polypeptide toxin is only conditionally lethal, then said method additionally can comprise the step of providing conditions that produce the lethal phenotype; whereby cells of the neuroendocrine tumor are selectively killed.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 2 illustrates the nucleotide sequence of an INSM1 promoter (−1661-+40 bp) having the sequence SEQ ID NO: 1.

FIG. 3 illustrates the nucleotide sequence of a pair of tandem nicotinic acetylcholine receptor (nAChR) neuronal restrictive silencer elements (NRSEs) having a 5' terminal BgIII restriction site and a 3' HindIII restriction site and having the nucleotide sequence SEQ ID NO: 2.

FIG. 4 illustrates the nucleotide sequence of an HS4 insulator sequence (approximately 1.2 kb) having the nucleotide sequence SEQ ID NO: 3.

FIG. 5 illustrates the nucleotide sequence of an HS4 core sequence (approximately 250 bp) having the nucleotide sequence SEQ ID NO: 4.

FIG. 6 illustrates the nucleotide sequence encoding a *Gaussia* bioluminescent reporter having a 5' terminal HindIII restriction site and a 3' NotI restriction site and having the nucleotide sequence SEQ ID NO: 5.

FIG. 7 illustrates the nucleotide sequence of an IRES element having the nucleotide sequence SEQ ID NO: 6.

FIG. 8: illustrates the nucleotide sequence encoding a Δ24E1A polypeptide having the nucleotide sequence SEQ ID NO: 7.

FIG. 9 illustrates the amino acid sequence (SEQ ID NO: 8) of a human E1A polypeptide.

FIG. 10 illustrates the nucleotide sequence encoding a thymidine kinase (TK) having the nucleotide sequence SEQ ID NO: 9.

FIG. 11 illustrates the nucleotide sequence of a 3'-untranslated region having the nucleotide sequence SEQ ID NO: 10.

FIGS. 12A-12E illustrate viral replication and protein expression.

FIG. 12A is a graph illustrating viral replication in INSM1-positive rat insulinoma cells (RIN). RIN cells were seeded in a 6-well plate at a density of $2 \times 10^6$ cells per well and infected with a viral concentration of 10 MOI or 200 MOI. After incubation for 3 days, cells and medium were collected and the viral particles were released into the medium by freeze-thaw lysis. The isolated viruses were then titered by immunostaining (n=6). To examine the expression of viral proteins (HSV-tk and E1A), Ad-INSM1p-HSV-tk and Ad-INSM1p-E1A-HSV-tk were used to infect RIN, MIN, β-TC1 (INSM1-positive insulinomas), and Panc-1 (INSM1-negative pancreatic epithelioid carcinoma) cells at 50 MOI. After incubation for 48 hours, total protein extracts were isolated from each cell line for HSV-tk and E1A analyses.

FIG. 12B is a digital image of a gel analysis for Ad-INSM1p-E1A-HSV-tk.

FIG. 12C is a digital image of a gel analysis for Ad-INSM1p-HSV-tk (K5).

FIG. 12D is a digital image of a gel analysis for Combination viruses.

FIG. 12E is a digital image of a gel analysis for CAR expression in uninfected cells.

FIGS. 13A-13D illustrate that the oncolytic virus in combination with Ad-INSM1p-HSV-tk increased efficacy of tumor cell killing. An MTS colorimetric assay was conducted to measure the cell survival with 3 insulinoma cell lines: RIN, MIN, β-TC1 (INSM1$^+$ insulinomas), and Panc-1 (INSM1$^-$ pancreatic epithelioid carcinoma).

FIG. 13A is a graph illustrating cells treated with Ad-INSM1p-Luc2.

FIG. 13B is a graph illustrating cells treated with Ad-INSM1p-E1A-HSV-tk

FIG. 13C is a graph illustrating cells treated with Ad-IMSM1p-HSV-tk (K5)

FIG. 13D is a graph illustrating cells treated with a combination of Ad-IMSM1p-HSV-tk and Ad-INSM1p-E1A-HSV-tk viruses. Cells were first treated with virus ranging from 0-100 MOI. Three days after infection, cells were treated with 100 μM GCV for five additional days. Cell survival was measured by MTS colorimetric analysis at 490 nm. (n=6).

FIG. 14A is a graph illustrating cells treated with Ad-INSM1p-Luc2.

FIG. 14B is a graph illustrating cells treated with Ad-INSM1p-E1A-HSV-tk.

FIG. 14C is a graph illustrating cells treated with Ad-IMSM1p-HSV-tk (K5).

FIG. 14D is a graph illustrating cells treated with a combination of Ad-IMSM1p-HSV-tk and Ad-INSM1p-E1A-HSV-tk viruses. Cancer cells were infected with 50 MOI viruses for 3 days, after which 0-200 μM ganciclovir was added for five additional days. Cell survival was measured by MTS colorimetric analysis at 490 nm. (n=6).

FIGS. 15A-15C illustrate that a combination virus treatment in an in vivo subcutaneous mouse xenograft tumor model.

FIG. 15A is a graph illustrating blood glucose levels in RIN cells pre-treated with 5 MOI Ad-INSM1-Luc2 for 24 hours and then injected into the right flank of 6-8 week old Nu/Nu mice. After 48 hours, Ad-INSM1-Luc2 ($10^9$ ifu) or a combination of Ad-INSM1-HSV-tk and Ad-INSM1-E1A-HSV-tk ($5 \times 10^8$ ifu each) were injected directly into the tumor site (marked after tumor cell injection). GCV treatment was started 3 days after injection (arrow) to allow for viral replication to occur inside the tumor cells. Blood glucose was measured daily via tail vein.

FIG. 15B is a digital image illustrating luminescent activity of the tumor in a representative mouse treated with either Ad-INSM1-Luc2 measured at days 3, 6, 9, and 12.

FIG. 15C is a digital image illustrating luminescent activity of the tumor in a representative mouse treated with a combination of Ad-IMSM1-HSV-tk and Ad-INSM1-E1A-HSV-tk was measured at days 3, 6, 9, and 12.

FIGS. 18A-18C illustrate Ad-INSM1p-Met vector expressed *Metridia* luciferase specifically in INSM1-positive cell lines. An increasing Ad-INSM1p-Met concentration (0-50 MOI) and a constant Ad-SV40-Luc2 concentration (5 MOI) was used to infect INSM1-positive (solid lines) and -negative (dot lines) cell lines in culture.

FIG. 18A is a graph illustrating Ad-INSM1p-Met vector expressed *Metridia* luciferase expression specifically in NE lung cancer H1155, UMC-11, H82, and lung adenosquamous carcinoma H596 cells.

FIG. 18B is a graph illustrating Ad-INSM1p-Met vector expressed *Metridia* luciferase expression specifically in Neuroblastoma SK-N-Be(2) and SH-SYSY, retinoblastoma WERI-Rb-1, pheochromocytoma PC-12, medulloblastoma D283 Med, and cervical adenocarcinoma HeLa cells.

FIG. 18C is a graph illustrating Ad-INSM1p-Met vector expressed *Metridia* luciferase expression specifically in Insulinoma βTC-1, MIN, RIN, and pancreatic epithelioid carcinoma PANC-1 cells were used. Values are expressed as ratios between extracellular and intracellular luciferase activity. *: $p<0.05$, : $p<0.01$, *: $p<0.001$ (n=3).

Figure 19:
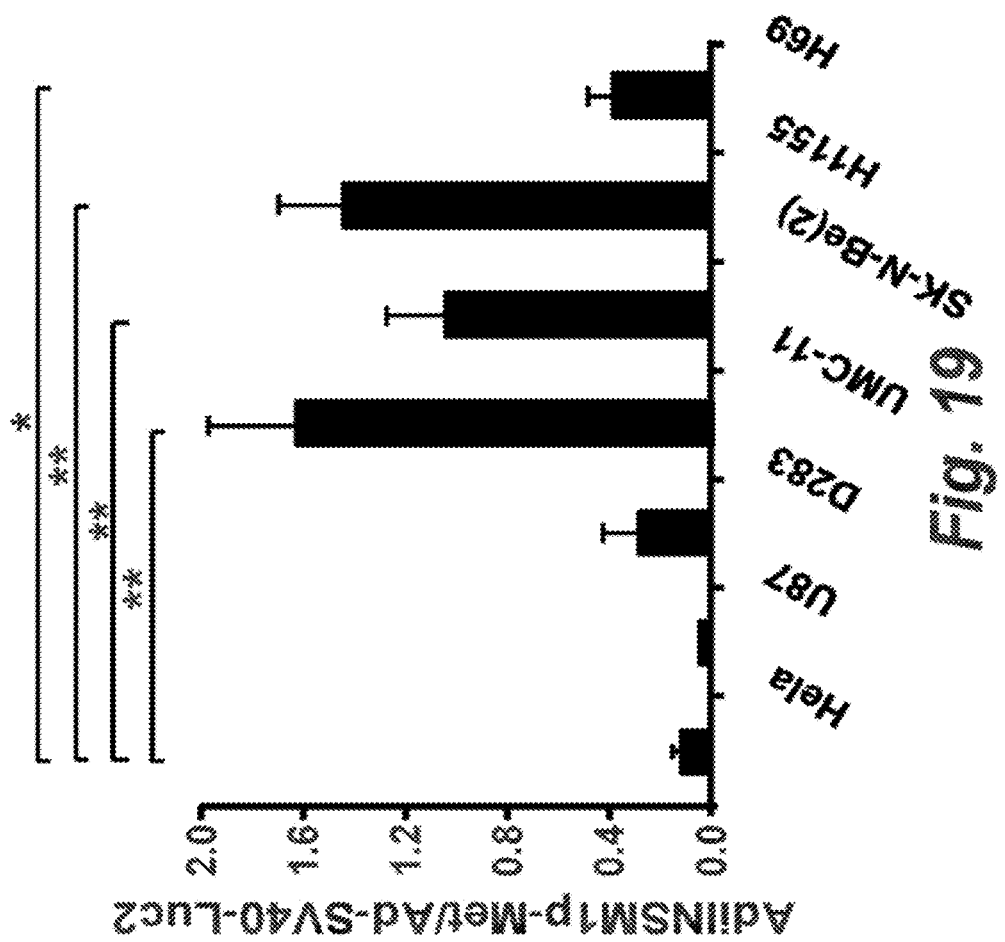

FIG. 19 is a graph illustrating *Metridia* luciferase secretion in xenograft human tumor culture. Ad-INSM1p-Met vector specifically expressed *Metridia* luciferase in ex vivo NE tumor cells. Cells harvested from established xenograft human tumors were infected with Ad-INSM1p-Met (100 MOI) and AdSV40-Luc2 (100 MOI). Data points are displayed as ratios between extracellular and intracellular luciferase luminescence. *: $p<0.05$, : $p<0.01$, *: $p<0.001$ (n=4).

FIGS. 20A-20C illustrate Ad-INSM1p-Gau vector expressed *Gaussia* luciferase specifically in INSM1-positive cell lines. An increasing Ad-INSM1p-Gau concentration (0-50 MOI) and a constant AdSV40-Luc2 concentration (5 MOI) was used to infect INSM1-positive (solid lines) and -negative (dot lines) cell lines in culture.

FIG. 20A is a graph illustrating Ad-INSM1p-Gau vector expressed *Gaussia* luciferase specifically in NE lung cancer H1155, UMC-11, H82, and lung adenosquamous carcinoma H596 cells.

FIG. 20B is a graph illustrating Ad-INSM1p-Gau vector expressed *Gaussia* luciferase specifically in Neuroblastoma SK-N-Be(2) and SH-SY5Y, medulloblastoma D283Med, and cervical adenocarcinoma HeLa cells.

FIG. 20C is a graph illustrating Ad-INSM1p-Gau vector expressed *Gaussia* luciferase specifically in Insulinoma βTC-1, MIN, RIN, and pancreatic epithelioid carcinoma PANC-1 cells were used. Values are expressed as ratios between extracellular and intracellular luciferase activity. *: $p<0.05$, : $p<0.01$, *: $p<0.001$ (n=3).

Figure 21:
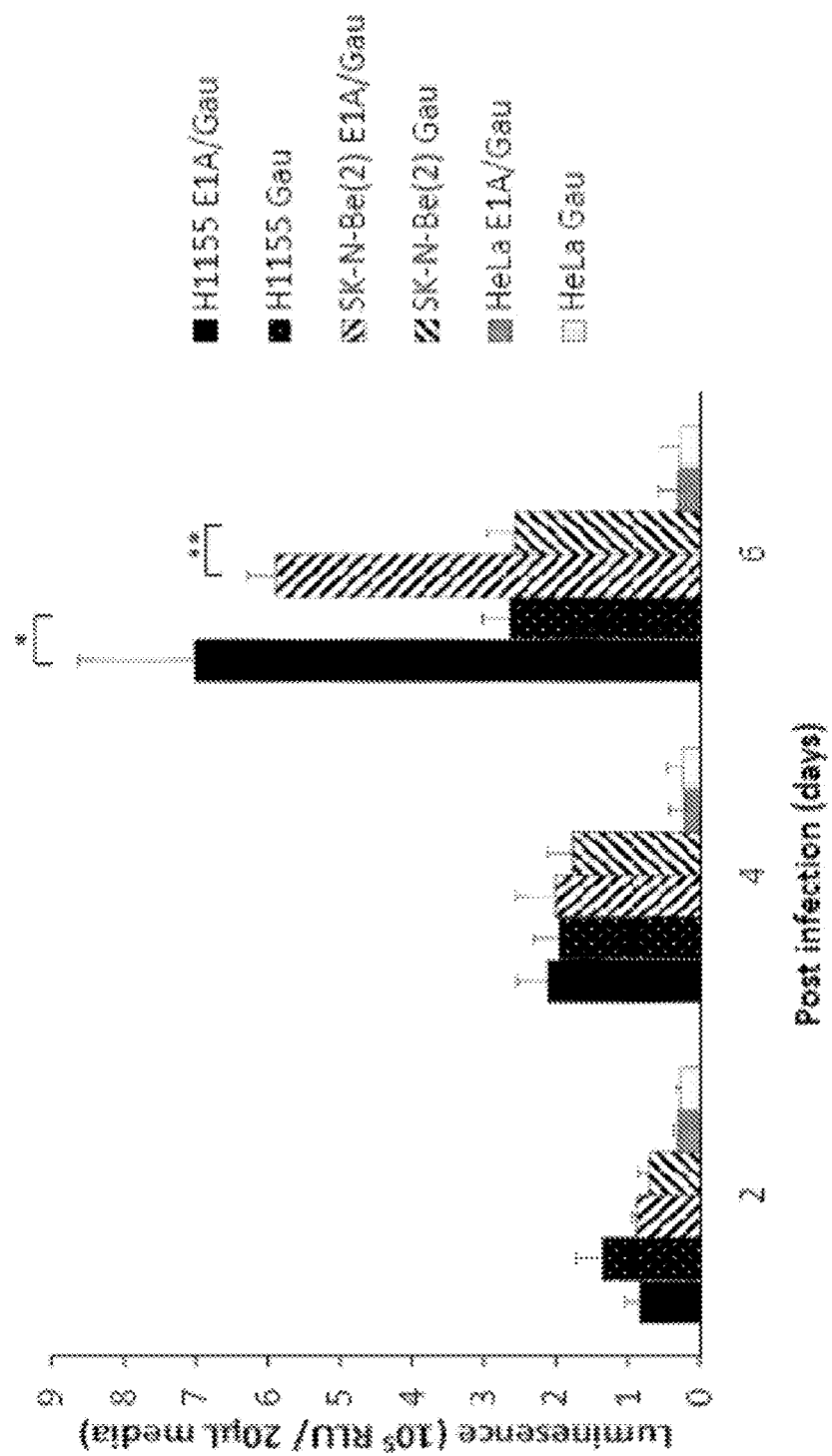

FIG. 21 is a graph illustrating oncolytic virus in combination with Ad-INSM1p-Gau increases sensitivity of *Gaussia* luciferase detection. The combination of Ad-INSM1p-Gau and Ad-INSM1p-Δ24E1A was able to increase the sensitivity of luciferase detection after 6 days post infection. To test the effects of Ad-INSM1p-Gau in combination with the conditionally replicating adenovirus Ad-INSM1p-Δ24E1A, cells were infected with combination of 10 MOI Ad-INSM1p-Gau and Ad-INSM1p-Δ24E1A (a total of 20 MOI). Media were collected 2, 4, and 6 days after infection and showed the highest luciferase activity at day 6. *: $p<0.05$, **: $p<0.01$ (n=3).

Figure 22:
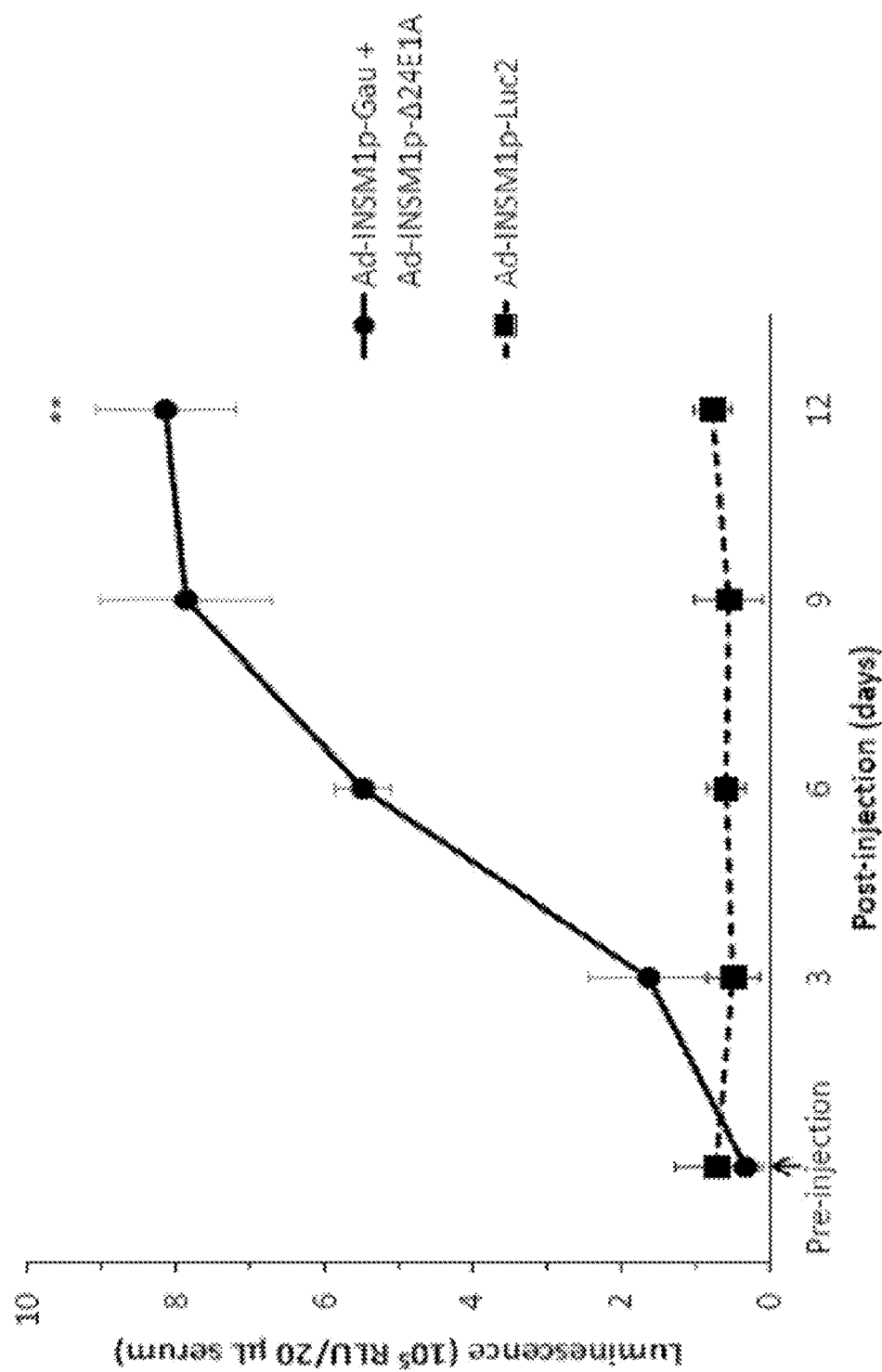

FIG. 22 is a graph illustrating in vivo *Gaussia* secretion assay in a mouse xenograft tumor model. The combination assay in a mouse xenograft tumor model. The combination of Ad-INSM1p-Gau and Ad-INSM1p-Δ24E1A was able to express detectable *Gaussia* luciferase in circulation 12 days after infection in vivo. A mixture of Ad-INSM1p-Gau in combination with the Ad-INSM1p-Δ24E1A conditionally replicating adenovirus (1×109 ifu total) was injected into established xenograft tumors (H1155 NE lung cancer cells). Serum was collected from each animal (n=3) 3 to 12 days post infection. **: $p<0.01$ (n=3).

Figure 23:
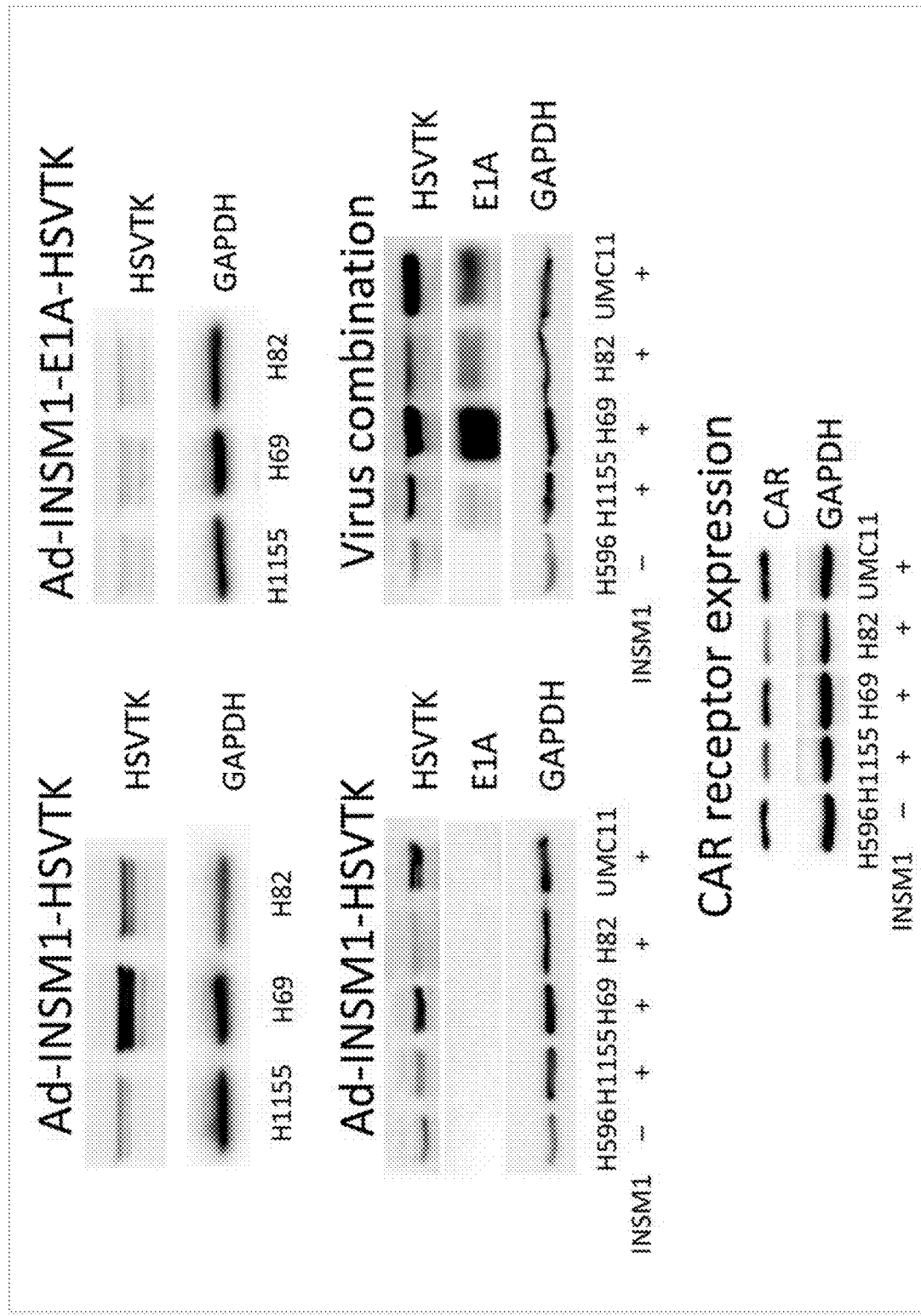

FIG. 23 is a series of digital images illustrating Western blot analyses of viral protein expression. To examine the expression of viral proteins, Ad-INSM1-HSVTK and Ad-INSM1-E1A-HSVTK were used to infect H155 (INSM1+ LCLC), H69, H82, UMC11 (all INSM1+ SCLC), and H596 (INSM1-non-SCLC) cells at 50 MOI. After incubation for 48 hours, total protein extracts were isolated from each cell line. The viral combination expressed higher levels of HSVTK than either virus alone.

Figure 24:
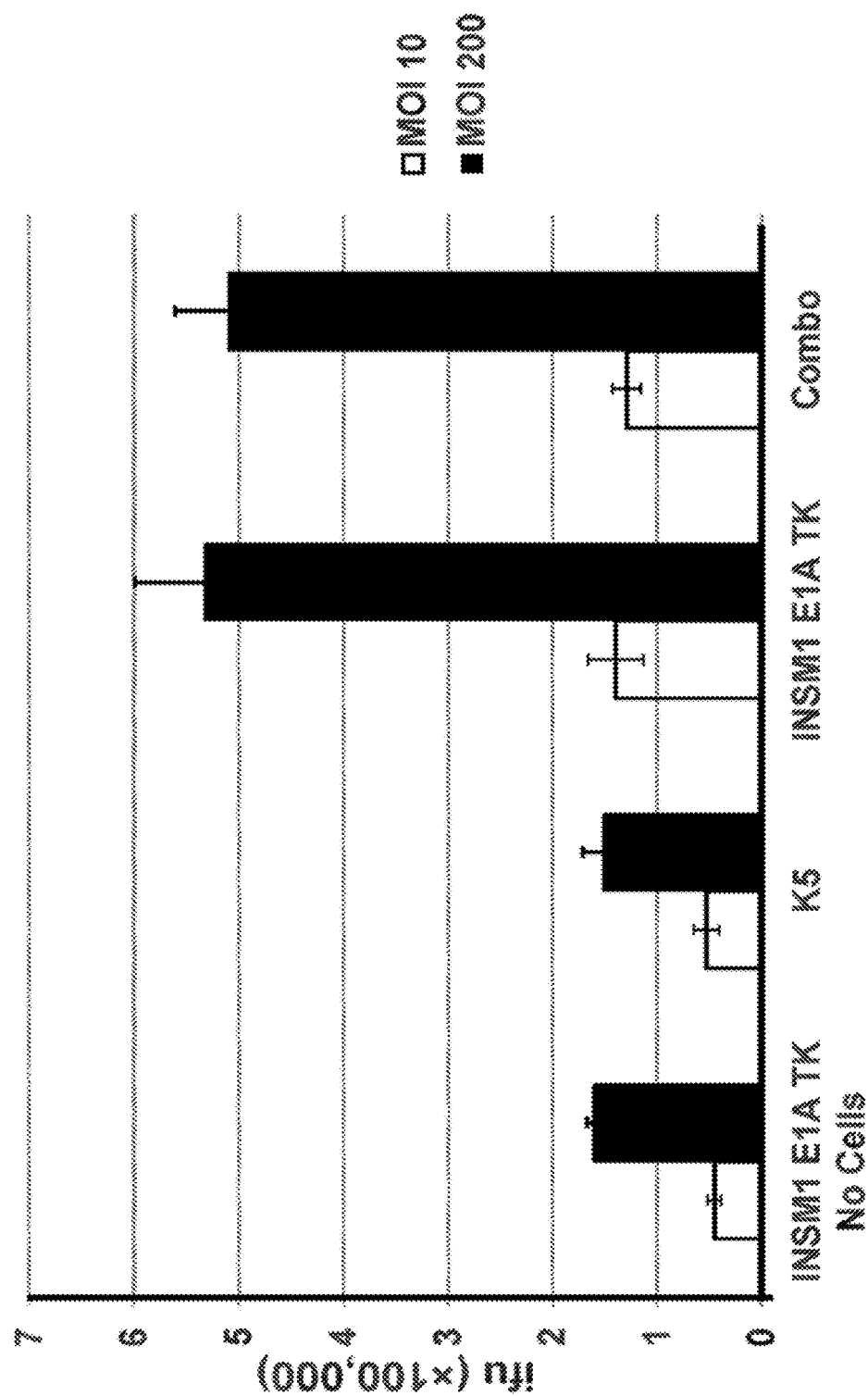

FIG. 24 is a graph illustrating viral replication in INSM1 positive SCLC cells. H1155 cells were plated on 6-well plates at a density of 2×10⁶ cells/well and infected with a viral concentration of 10 MOI or 200 MOI. After incubation for approximately 3 days, cells were collected and viral particles released by freeze thaw lysis. The isolated virus were then titered by immunostaining. (n=6)

Figure 25:
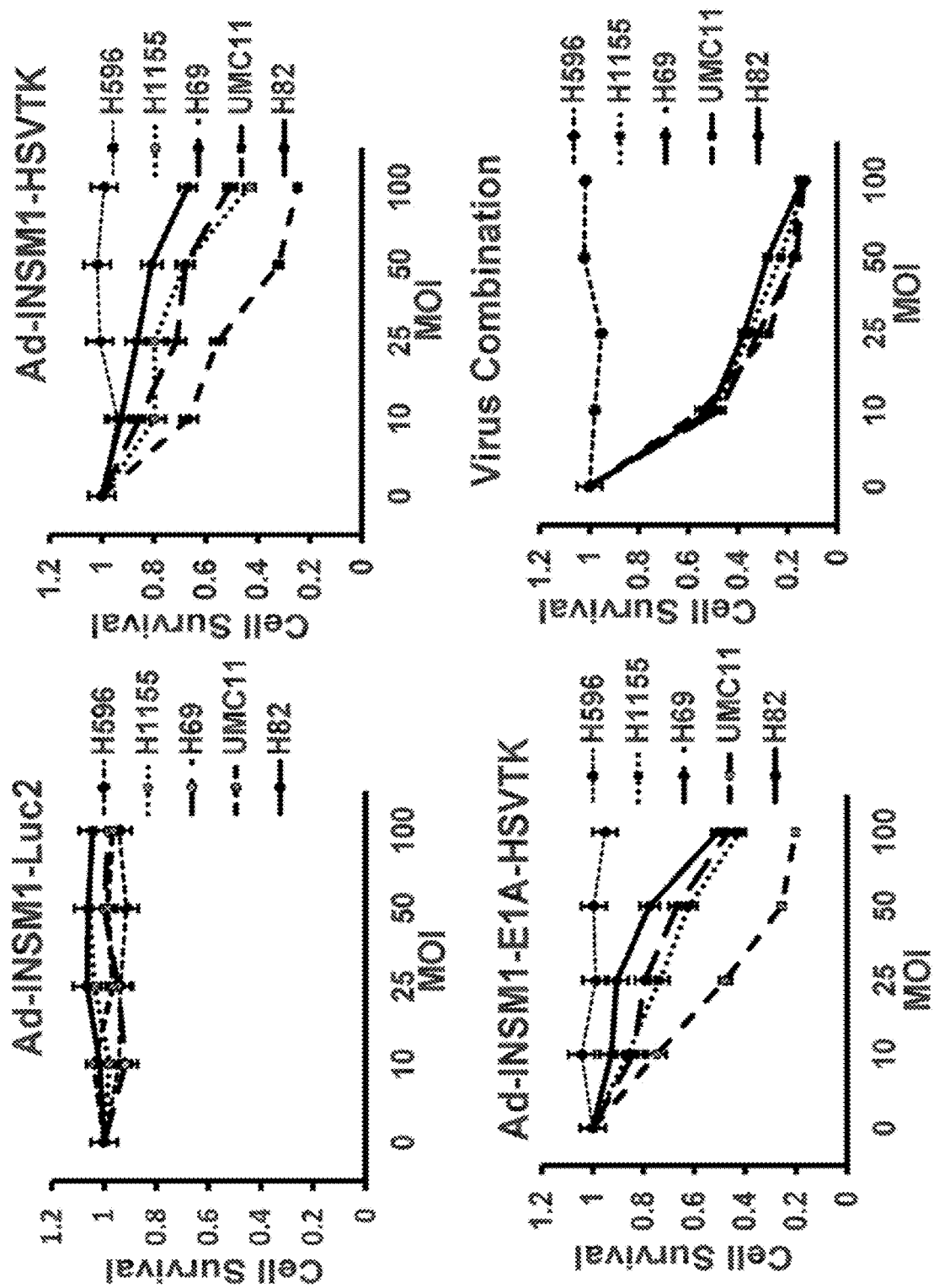

FIG. 25 is a series of graphs illustrating cell survival assay. An MTS colorimetric assay was conducted with 5 lung cancer cell lines: H155 (INSM1⁺ LCLC), H69, H82, UMC11 (all INSM1⁺ SCLC), and H596 (INSM1⁻ non-SCLC). Cells are first treated with virus ranging from 0-200 MOI. Three days after infection with viral constructs, cells were treated with 100 μM GCV for 5 days. Cell survival was measured by MTS colorimetric analysis at 490 nm. (n=3)

Figure 26:
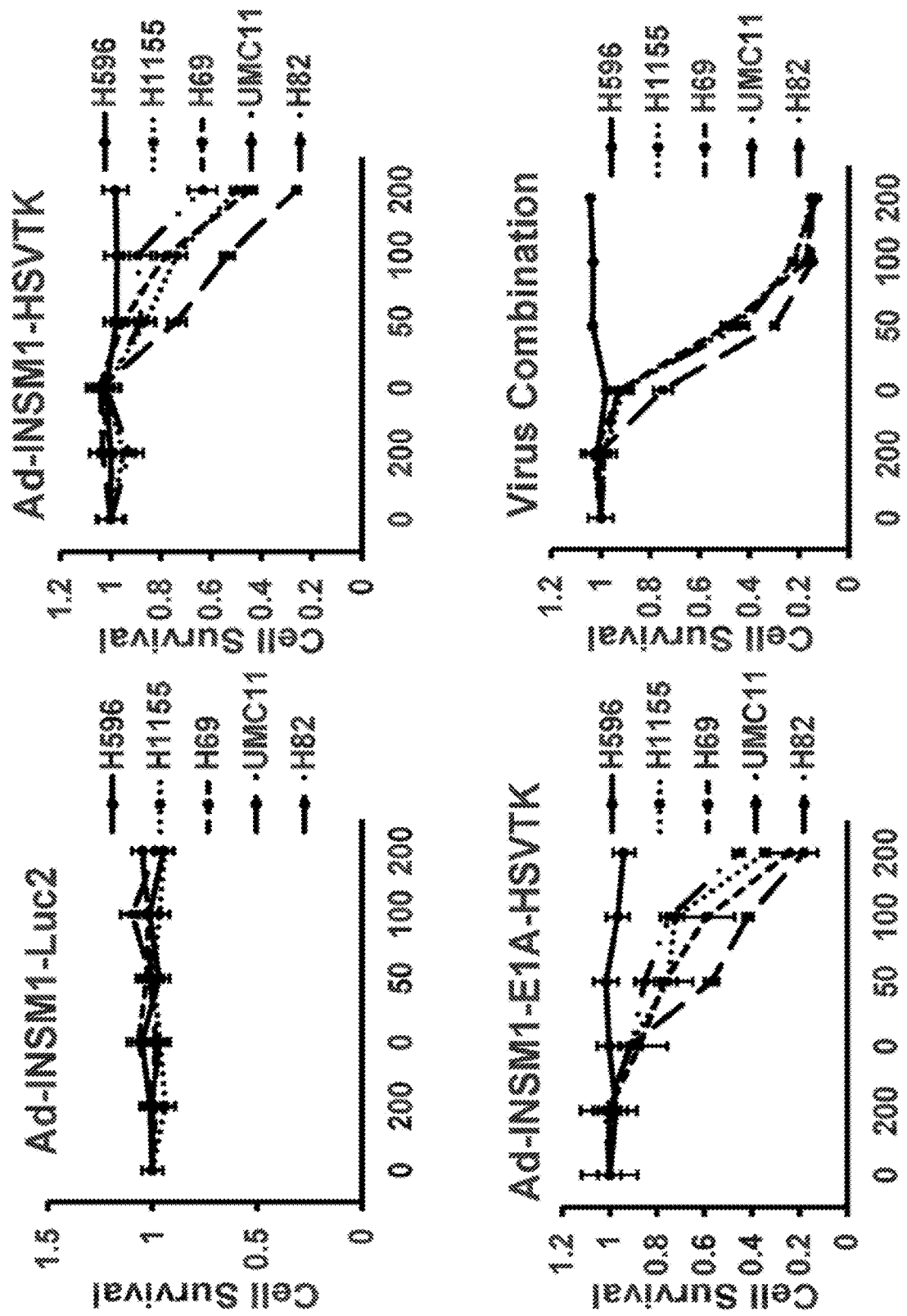

FIG. 26 is a series of graphs illustrating cell survival assay. An MTS assay was conducted with 5 lung cancer cell lines: H155 (INSM1⁺ LCLC), H69, H82, UMC11 (all INSM1+ SCLC), and H596 (INSM1-non-SCLC). Cancer cells were infected with 50 MOI viruses for 3 days, after which 0-200 μM ganciclovir was added for 5 additional days. Cell survival was measured by MTS colorimetric analysis at 490 nm. (n=3).

Figure 27A:
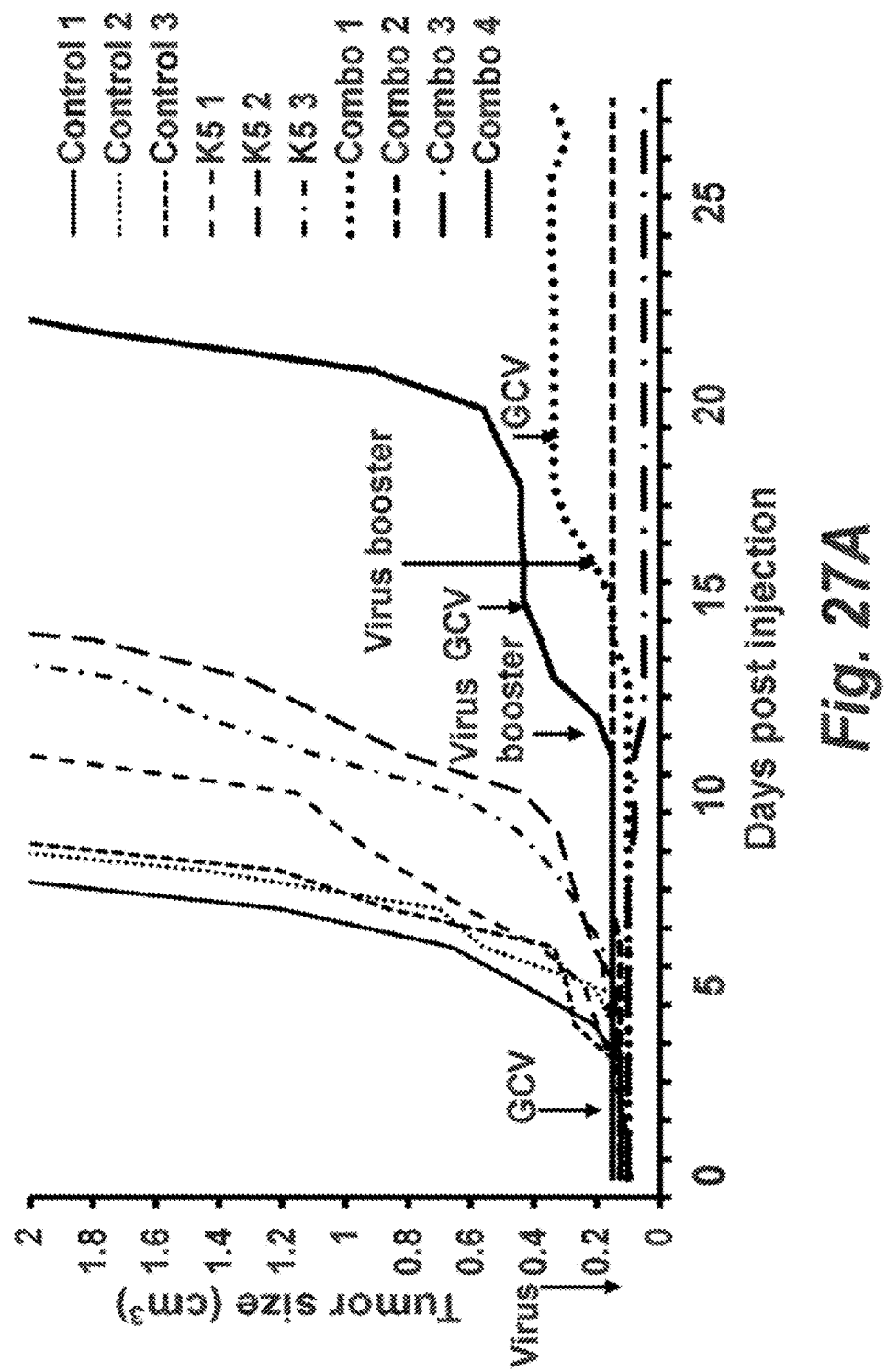
Figure 27B:
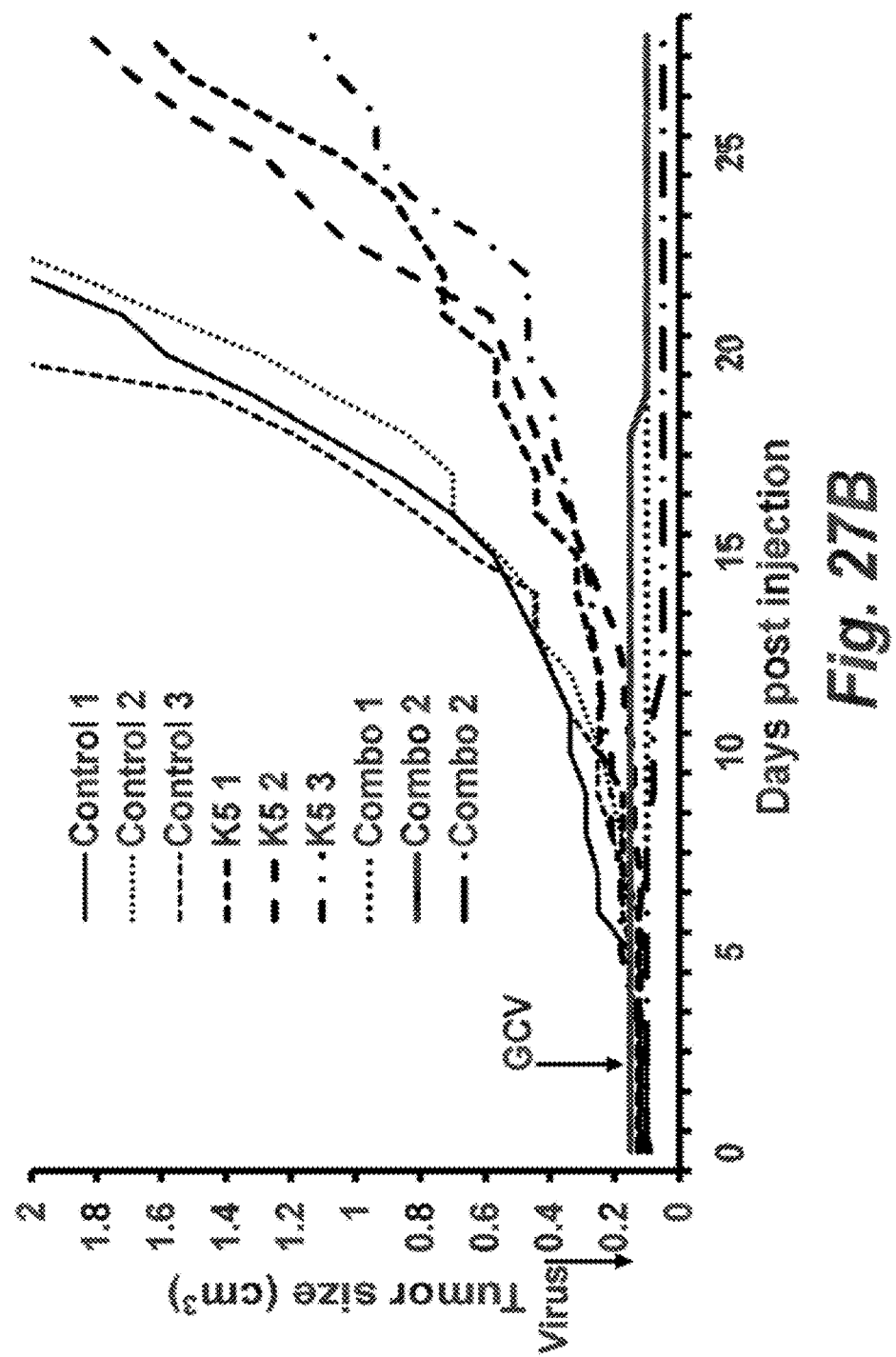
Figure 27C:
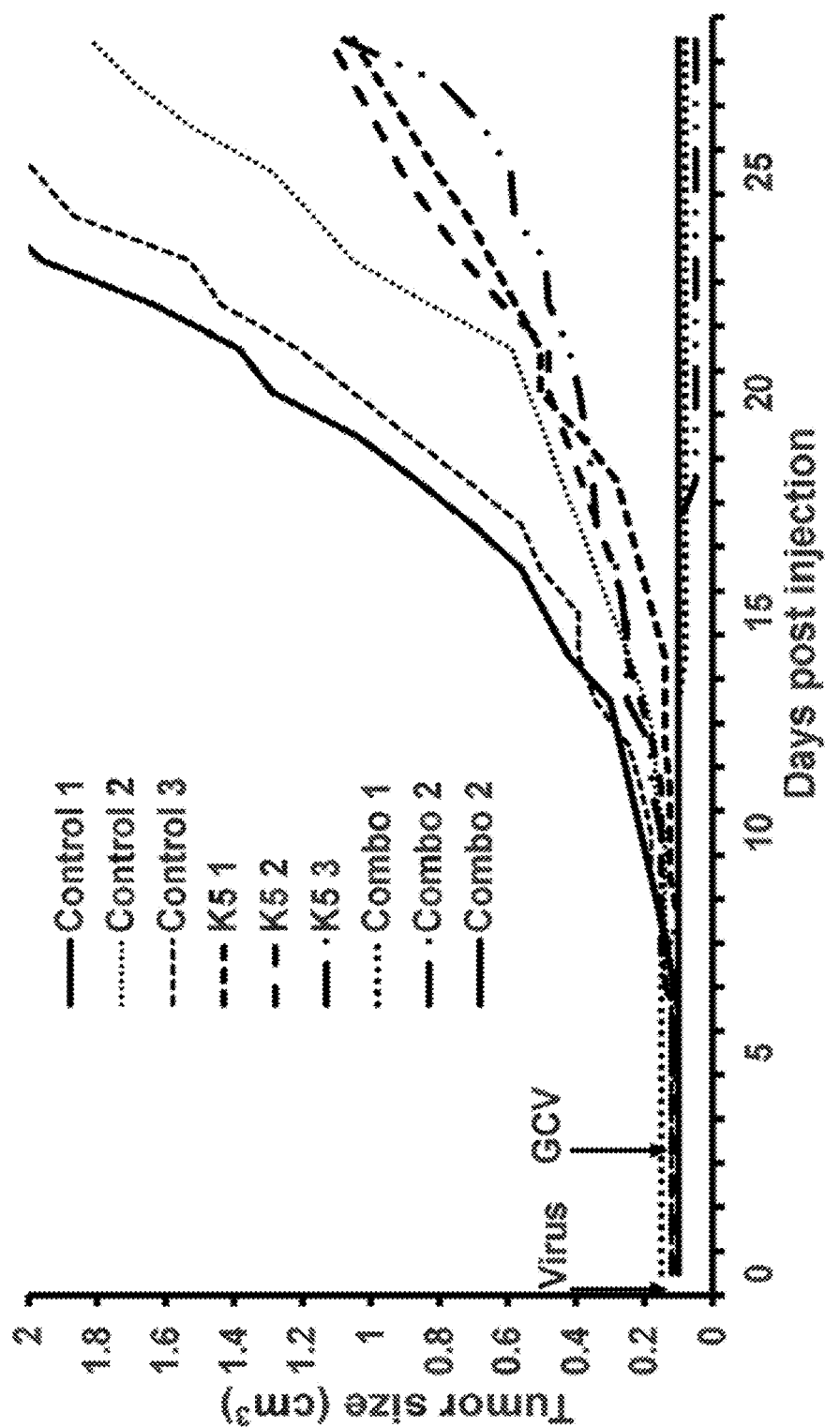

FIGS. 27A-27C illustrate subcutaneous xenograft tumors. A total of 10⁹ cells were injected subcutaneously into the right flank of 4 week old Nu/Nu mice. After establishment of tumor, the viral combination was introduced via injection into the tumor. GCV treatment was started 3 days after infection to allow for viral replication to occur. In certain tumors, a second viral boost was introduced after tumor growth accelerated despite viral treatment. Tumors were measured daily in 3 dimensions to determine volume.

FIG. 27A is a graph illustrating H1155 large cell lung carcinoma.

FIG. 27B is a graph illustrating UMC11 SCLC.

FIG. 27C is a graph illustrating H82 SCLC.

FIG. 28 are digital images illustrating subcutaneous xenograft tumors. Photograph of H1155 subcutaneous tumors after completion of treatment with combination virus (left) or control Ad-INSM1-Luc2 virus (right).

Figure 29:
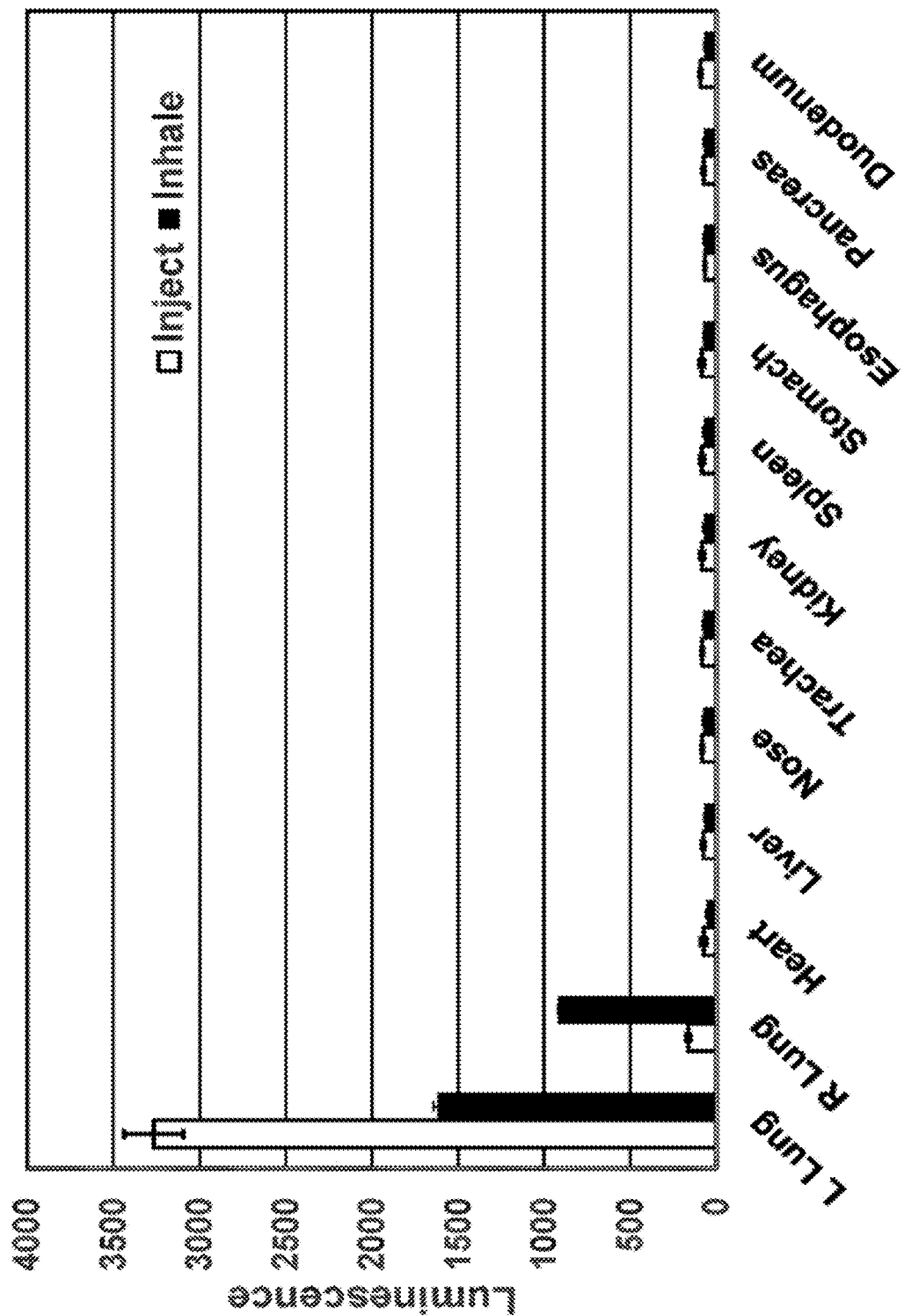

FIG. 29 is a graph illustrating nasal inhalation delivers viruses primarily into the left and right lungs. Nasal inhalation of virus was conducted using 10⁹ ifu Ad-CMV-Luc2 at a total volume of 40 μL into 4 week old Nu/Nu mice. After incubation for 24 h post-inhalation, organs were harvested from each mouse the protein extracts were produced. Luciferase activity was detected in each organ using 20 μL of extract to be used for the Pierce Luciferase Glow Assay Kit. (n=3).

Figure 30:
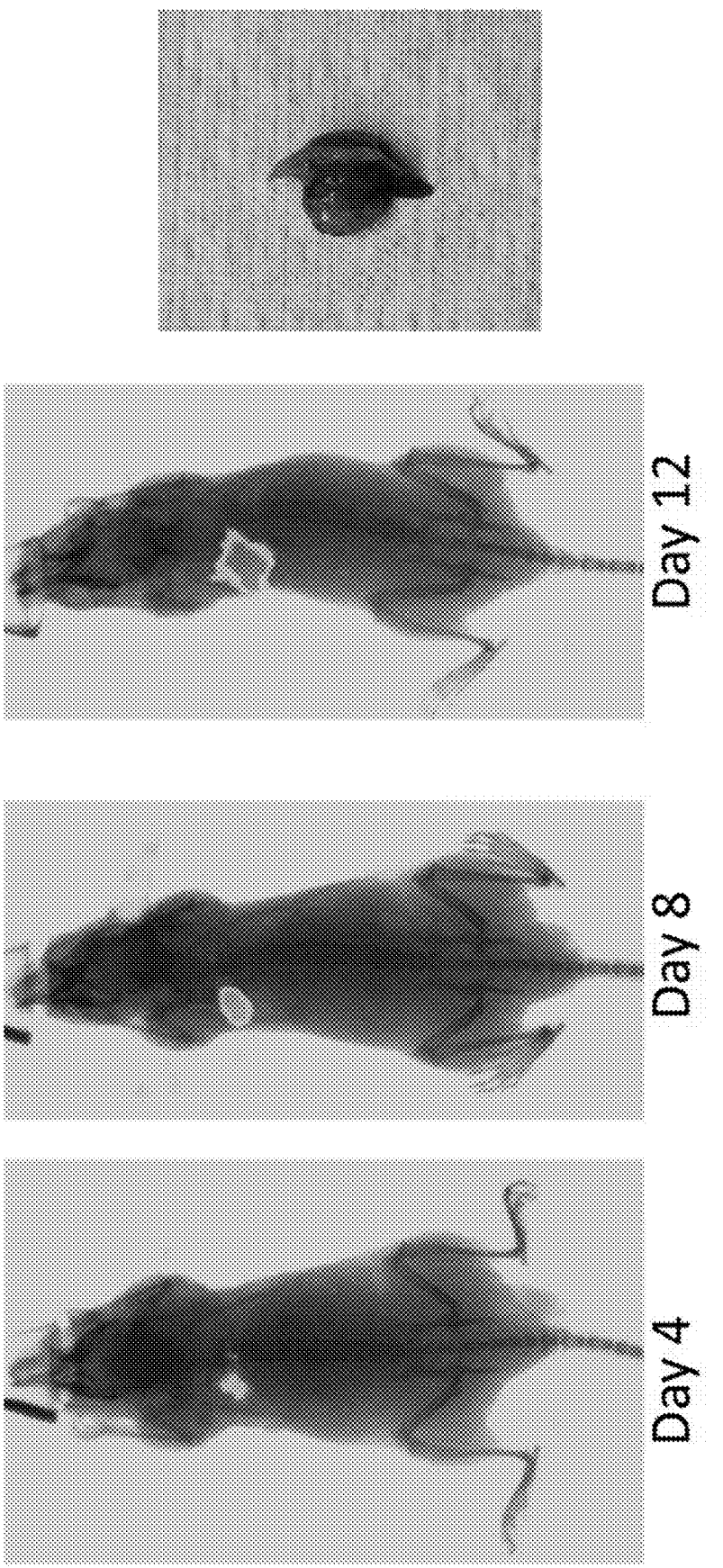

FIG. 30 are digital images illustrating orthotopic lung tumor generation. H1155 tumor cells were injected into the left lung of Nu/Nu mice. A total of $10^9$ cells were injected mixed with a 1:5 concentration of matrigel. After 3 days, $10^9$ ifu Ad-INSM1-Luc2 was introduced to the tumor bearing mouse by nasal inhalation. Luciferin substrate was injected intraperitoneally at day 4 to detect luciferase activity. This process was repeated for days 8 and 12, after which the mouse was sacrificed and the lung removed (right).

Figure 31:
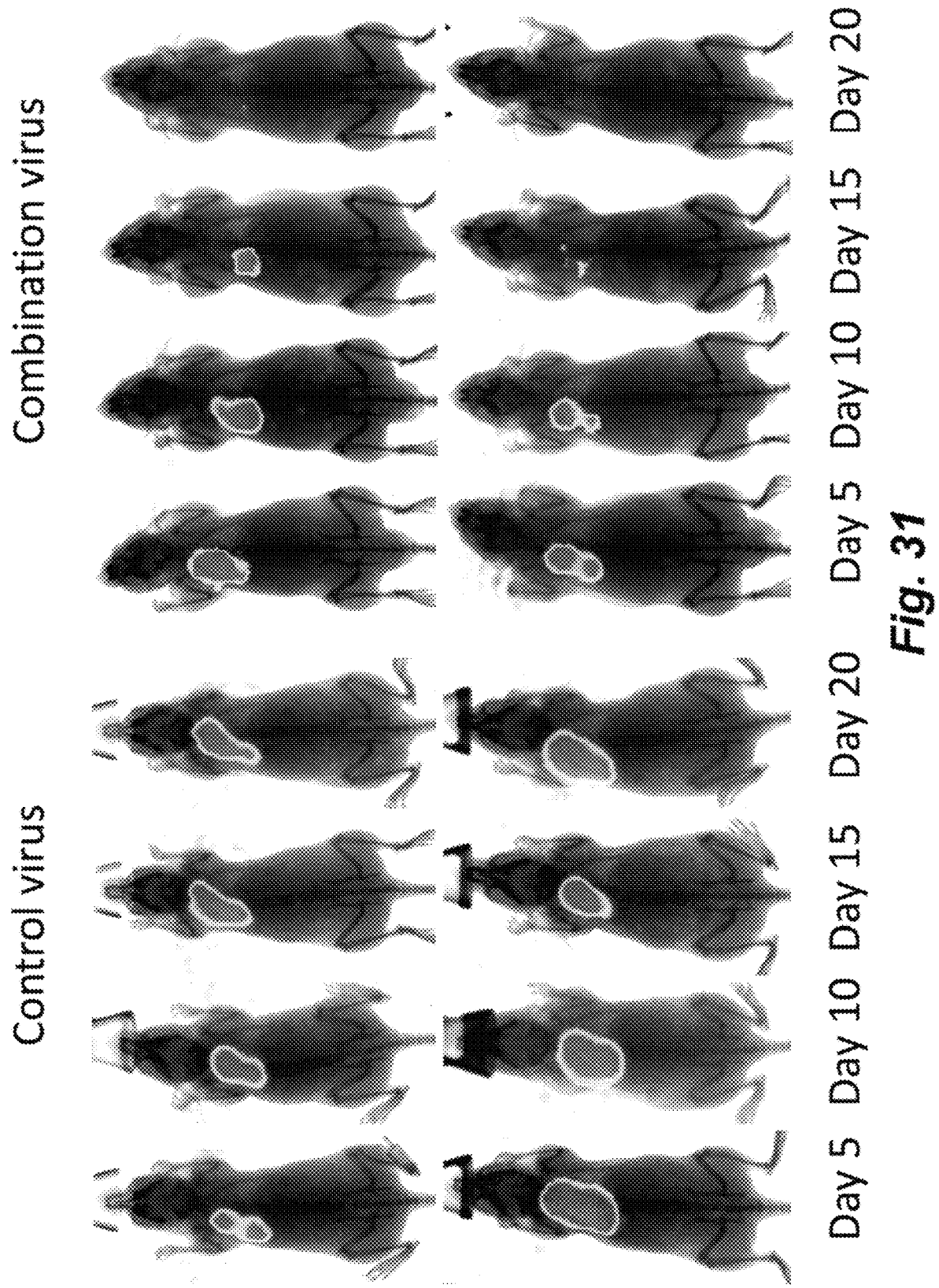

FIG. 31 are digital images illustrating treatment and monitoring of orthotopic lung tumors. UMC11 SCLC tumor cells were first infected with 10 MOI Ad-INSM1-Luc2 for 24 h. After infection, $10^9$ cells were mixed with a 1:5 concentration of matrigel and injected into the left lung of Nu/Nu mice. After 3 days, $10^9$ ifu combination virus or Ad-INSM1-Luc2 was introduced to the tumor bearing mice by nasal inhalation of 40 μL of viral solution. Luciferin substrate was IP injected every 5 days to detect luciferase activity.

FIG. 32: Nucleotide sequence of the 2×ins-INSM1p-2× NRSE-Δ24E1A-IRES-HSV-tk construct that is inserted into the adenovirus 5 (Ad5) viral vector (SEQ ID Nos: 11).

FIG. 33: Nucleotide sequence of the 2×ins-INSM1p-2× NRSE-Δ24E1A-IRES-HSV-tk construct that is inserted into the adenovirus 5 (Ad5) viral vector (SEQ ID Nos: 12).

FIG. 34: Nucleotide sequence of a 2×ins-INSM1p-2× NRSE-Δ24E1A-3'-untranslated region construct that may be inserted into an adenovirus 5 (Ad5) viral vector (SEQ ID NO: 13).

FIG. 35: Nucleotide sequence of a 2×ins-INSM1p-2× NRSE-Gaussia-3'-untranslated region construct that may be inserted into an adenovirus 5 (Ad5) viral vector (SEQ ID NO: 14).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

NE, neuroendocrine; INSM1, insulinoma-associated-1; NRSEs, neuronal restrictive silencer elements; HSV-tk, herpes simplex virus thymidine kinase; GCV, ganciclovir; DMEM, Dulbecco Modified Eagle Medium; MOI, multiplicities of infection; CAR, coxsackievirus and adenovirus receptor; Luc2, luciferase2; Gau, *Gaussia*, Met, *Metridia*; RFU, reflective fluorescence unit.

Definitions

As used in the specification and in the claims, the term "construct" or "expression construct" refers to a functional DNA nucleotide sequence that is artificially constructed to transfer or express one or more genes of interest.

The terms "neuroendocrine cancer" or "neuroendocrine tumor" as used herein refer to a cancer that arises from the neuroendocrine system, a diffuse system in which the nervous system and the hormones of the endocrine glands interact, or from non-endocrine cells by acquiring some of the properties of neuroendocrine cells through an oncogenic process such as Selective Tumour gene Expression of Peptides essential for Survival (STEPS) (see, North (2000) *Exper. Physiol.* 85S:27S-40S). Most of the well-described adult neuroendocrine tumors are distinctive and arise from a known primary site, including the carcinoid, pheochromocytoma, and Merkel's cell tumors. Carcinoid tumors can be benign or malignant. Carcinoid cancers include stomach, pancreas, colon, liver, lung, ovarian, breast, testicular, and cervical cancer. Neuroendocrine tumors of the lungs are classified as small cell carcinoma. It is characterized by its origin in large central airways and histological composition of sheets of small cells with scanty cytoplasm. Small cell carcinoma is very aggressive, metastasizing early and often. Pheochromocytoma is a cancer of the adrenal medulla. This condition often causes the adrenal glands to make too much catecholamine. Pheochromocytoma may arise as part of a condition called multiple endocrine neoplasia (MEN) syndrome, which can result in other cancers of the endocrine system and hormonal abnormalities. Merkel's cell tumors are cancers that form on or just beneath the skin, but sometimes are also thought to arise from underlying soft tissue. They are also known as neuroendocrine cancer of the skin. Merkel's cell tumors are fast-growing and often spread to other parts of the body. In particular embodiments of the present invention, a neuroendocrine cancer is a carcinoid cancer such as breast cancer or SCLC.

The term "neuronal restrictive silencer element" or "NRSE" as used herein refers to a DNA segment that is known to mediate transcriptional repression of many neuron-specific genes via the neuron-restrictive silencer factor (NRSF) or repressor element silencing transcription factor. The neuron-restrictive silencer element (NRSE) has been identified in several neuronal genes and confers neuron specificity by silencing transcription in non-neuronal cells. NRSE elements when bound by its cognate protein, the neuron restrictive silencing factor, NRSF, can strongly repress transcription in non-neuronal cells as well as allow transcription of the same gene in neuronal cells. Examples of neuronal restrictive silencer elements (NRSEs) include those derived either from the mouse nicotinic acetylcholine receptor (nAChR) or the rat superior cervical ganglion 10 (SCG10) promoters. Multiple neuronal genes have been shown to be repressed by NRSF protein via a NRSE element located in their promoter regions. Other neuronal genes repressed by NRSF in non-neuronal cells include protocadherin, tryptophan hydroxylase-2, mu opioid receptor, tyrosine hydroxylase, N-methyl-D-aspartate receptor 2B, proprotein convertase 2, glutamate receptor 2, GluR2, arginine vasopressin, brain-derived neutrophic factor, neural-specific type II sodium channel, and dopamine beta hydroxylase genes. (See also, U.S. Patent Application Publication No. 2006/0121013)

The term "insulator element" as used herein refers to a DNA segment that has the ability to protect genes from inappropriate signals originating from the surrounding environment by acting as a physical barrier or boundary. An insulator element blocks the interaction between a promoter and enhancers when it is inserted between them, or it confers expression of integrated foreign genes independent of their position in the chromatin. The 5' HS4 element, derived from the chicken .beta.-globin locus (the first insulator identified in vertebrates), has been used with success to improve heterologous construct expression in transgenic animals. The chicken β-globin HS4 insulator element has been shown to block the actions of enhancer elements in addition to functioning as a physical boundary that can prevent the spread of gene silencing (14-20). In this embodiment of the construct, the insulator element is used to prevent the adenoviral sequences from potentially interrupting the INSM1 promoter activity and to prevent the interference from the viral backbone with respect to the tissue selectivity of the promoter incorporated into the viral vectors.

The term "Internal Ribosome Entry Site (IRES)" as used herein refers to an RNA element that allows for translation initiation in an end-independent manner. In eukaryotic translation, initiation typically occurs at the 5' end of mRNA molecules, since 5' cap recognition is required for the assembly of the initiation complex. The location for IRES elements is often in the 5'UTR, but can also occur elsewhere in mRNAs and may be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

The term "ganciclovir" as used herein refers to 2-amino-9-{[(1,3-dihydroxypropan-2-yl)oxy]methyl}-6,9-dihydro-3H-purin-6-one, a nucleoside analog. The term "nucleoside analog" as used herein refers to a compound having a molecular structure similar to a nucleoside (e.g., adenosine, guanosine, thymidine and cytidine, and deoxy derivatives thereof) and/or a nucleic base (e.g., adenine, guanine, thymine and cytosine). The term "analog" indicates that the compound is capable of interacting (e.g., as a substrate and/or inhibitor) with an enzyme for which a nucleoside and/or nucleic base is a natural substrate and/or inhibitor.

In embodiments of the disclosure, the nucleoside analog can an antiviral activity which is triggered by thymidine kinase (TK) and results in a selective nucleoside analog. The nucleoside analog is converted into an active, phosphorylated form in cells having the TK (i.e., cells infected with an expression vector encoding and expressing the TK) while remaining in the original inactive, non-phosphorylated form in other cells. By remaining in an inactive form in non-infected cells, side effects caused by damage to non-infected cells are reduced considerably.

The term "reporter gene" as used herein refers to a gene, usually a foreign or modified gene, that is added to a construct and is expressed due to the promoter in the construct and the expression allows easy identification of cells or tissues that have taken up the construct. Common reporter genes include the gene that encodes jellyfish green fluorescent protein, which causes cells that express it to glow green under UV light, and the firefly luciferase gene which causes light emission when its substrate luciferin is added. Reporter genes are often placed downstream of the promoter region and in the proximity of the gene of interest to ensure that they are expressed together and not separated by cross-over events.

The term "toxin gene" s used herein refers to a gene that encodes a toxin that is capable of being readily produced either under the regulatory control of the INSM1 promoter. A "toxin" is a gene product(s) that causes or leads to the destruction or incapacitation of a cell. This definition is intended to include the induction of indigenous events leading to cell death, such as apoptosis or necrosis. A "toxin" may, for example, be a compound that induces conditional lethality, i.e., cell death requires both expression of a conditional toxin gene (for example, thymidine-kinase) and the exogenous administration of a compound (for example, ganciclovir or acyclovir) that together produce a lethal effect. Another example is the combination of the gene encoding cytosine deaminase and the pro-drug 5-fluorocytosine. For example, a suitable toxin may be one of the many toxic peptides known in the art. In addition, the toxin should be capable of killing tumor cells or, optionally, the toxin may also kill neighboring cells, a "bystander" effect, but it should not have substantial systemic effects. There are numerous toxins from plants, animals, and bacteria satisfying these criteria, including naturally occurring, modified and synthetic toxins. Examples of toxins include without limitation synthetic and natural lytic peptides, cholera toxin, diphtheria toxin, Pseudomonas toxin, ricin toxin, cecropins, defensins, sarcotoxins, melittins, and magainins. One suicide gene therapy uses the gene herpes simplex virus thymidine kinase and ganciclovir. The disadvantage to this system includes significant liver toxicity unless precaution is taken to decrease its expression in liver cells. (See also, discussion in PCT/US00/0633 published as WO005377; U.S. Pat. Nos. 5,789,542 and 6,566,334.)

The term "viral vector" as used herein refers to a virus that is competent to infect a mammalian host cell and can be used to deliver the construct to the target cells or tumor or to an animal systemically. One example of a viral vector is the first generation E1/E3 deleted non-replicating Ad5 vector, but other forms of viral delivery systems are known and could be used. One of the disadvantages of the non-replicating adenovirus is the lack of persistence in vivo and one embodiment could be the use of a conditionally replicating oncolytic adenovirus. Additional examples of viral delivery systems include viruses that would result in more permanent expression such as lentivirus or adeno-associated virus (AAV). The advantage to these two viral systems is that they can be manipulated to alter their tropism for different cell types making them a more flexible platform.

Neuroendocrine tumors that can be treated or diagnosed using the described construct include without limitation retinoblastoma, medullablastoma, neuroblastoma, small cell lung carcinoma, non-small cell carcinoma with neuroendocrine phenotype, carcinoid, insulinoma, pheochromocytoma, medullary thyroid carcinoma, pituitary tumors, prostate carcinoma, and retinoblastoma tumors.

In describing and claiming the disclosed subject matter, the following terminology will be used in accordance with the definitions set forth below.

DESCRIPTION

Insulinomas are the most common type of islet cell tumors. Characteristically, patients with insulinomas can develop complications associated with hyperinsulinemia. Modification of an INSM1 promoter region to incorporate DNA elements that have silenced expression of neuronal genes in non-neuronal cells has increased the effectiveness and safety of using the INSM1 promoter for tumor treatment. To increase the safety of the transcriptionally-regulated suicide gene therapy, various DNA elements were included in the 1.7 kilobase pair INSM1 promoter for reduction in expression in unwanted tissues. The first modification was addition of two tandem copies of neuronal restrictive silencer elements (NRSEs) derived either from the mouse nicotinic acetylcholine receptor (nAChR) or the rat superior cervical ganglion 10 (SCG10) promoters. These NRSEs were placed in the construct directly downstream of the INSM1 promoter sequence. The most effective construct was the nAChR NRSE element positioned downstream of the INSM1 promoter. This construct increased the tissue specificity of the INSM1 promoter without a significant decrease in its activity. The INSM1 promoter has been linked to a toxin for tumor therapy and placed the constructs into the adenovirus 5 viral vector. Constructs were also tested with an insulator element with the INSM1 promoter to decrease the interference of the viral genome on its expression. A construct using the chicken HS4β-globin insulator element was shown to work as expected. Linking the construct to a reporter gene allowed for the detection of the placement of the viral vector, and can be used for diagnosing neuroendocrine tumors. Further constructs that do not decrease the INSM1 promoter activity but significantly augment the tumor specificity of the promoter have also been generated and can be used for treatment and diagnosing of neuroendocrine tumors.

The present disclosure encompasses embodiments of a modified neuroendocrine tumor-specific adenovirus expression vector that expresses a mutated adenovirus E1A gene (Δ24E1A) under the regulatory control of an INSM1 (insulinoma-associated-1) promoter. In addition, an IRES element is included to allow the expression of at least one second open reading frame encoding a polypeptide. This second polypeptide can be any that is useful for the detection of a neuroendocrine tumor cell, or for the reducing the proliferation or viability of the cell. For example, but not intended to be limiting the second polypeptide can be a tumor cell-specific lethal polypeptide or a conditionally lethal polypeptide such as thymidine kinase.

The expression vectors of the disclosure, therefore, enable selective gene expression specifically in neuroendocrine tumor cells, and allow for the expression of a heterologous ORF. The heterologous gene can be either a full genomic sequence (e.g., including introns), synthetic nucleic acid or a cDNA copy of a gene of interest, which encodes a protein or a polypeptide of interest, wherein the polypeptide includes biologically active ("bioactive") protein fragments. In a preferred embodiment, cDNA sequences are used for the purposes of the present technology due to the reduction in genomic complexity provided by removal of mRNA splice sites.

The ORF sequence may be selected from the group of reporter genes, cytotoxic tumor suppressor genes, toxin genes, prodrug activating genes and proapoptotic genes. In some embodiments, the second ORF sequence can be a reporter gene. As the name implies, a reporter gene does not confer any selective advantage on the cell into which it is introduced. Rather, a reporter gene encodes a product that confers on the cell a detectable biochemical or visually observable (e.g., fluorescent) phenotype. The reporter polypeptide can also include a fused or hybrid polypeptide in which another polypeptide is fused at the N-terminus or the C-terminus of the polypeptide or fragment thereof. A fused polypeptide is produced by cloning a nucleic acid sequence (or a portion thereof) encoding one polypeptide in-frame with a nucleic acid sequence (or a portion thereof) encoding another polypeptide. Techniques for producing fusion polypeptides are known in the art, and include ligating the coding sequences encoding the polypeptides so that they are in-frame and translation of the fused polypeptide is under the control of the TR cassette.

One commonly used class of reporter genes encodes an enzyme or other biochemical marker, which, when expressed in a mammalian cell, cause a visible change in the cell or the cell environment. Such a change can be observed directly, or can involve the addition of an appropriate substrate that is converted into a detectable product or the addition and binding of a metabolic tracer. Examples of these reporter genes are the bacterial lacZ gene which encodes the b-galactosidase (b-gal) enzyme, Firefly luciferase (Coleoptera beetle), *Renilla* luciferase (sea pansy), Herpes Simplex 1 thymidine kinase (HSV1-TK) and the mutant Herpes Simplex 1 thymidine kinase (HSV1-sr39tk) genes. In the case of b-gal, incubation of expressing cells with halogen-derivatized galactose results in a colored or fluorescent product that can be detected and quantitated histochemically or fluorimetrically. Other useful reporter genes encode proteins that are naturally fluorescent, including the (green fluorescent protein (GFP), enhanced yellow fluorescent protein (EYFP), or monomeric red fluorescent protein (mRFP1).

The second ORF sequence can encode a cytotoxic tumor suppressor gene that encodes a polypeptide capable of suppressing the neoplastic phenotype and/or inducing apoptosis. Examples of tumor suppressor genes useful in the practice of the present technology include the p53, adenomatous polyposis coli (APC), Wilm's Tumor (WT-1), retinoblastoma gene (Rb), Neurofibromatosis-1 (NF-1), NF-2 and von Hippel-Lindau (VHL) genes. In a preferred embodiment, the cytotoxic tumor suppressor gene is the p53 gene.

In one embodiment, the second ORF sequence may encode a "toxin gene" that binds to cellular receptor proteins and after uptake interferes with protein synthesis by blocking ribosome assembly or function. Examples of toxin genes include proteins such as Pseudomonas exotoxin (e.g., Exotoxin A or "ETA"), ricin toxin, diphtheria toxin, and the like. In one embodiment, the toxin gene is the diphtheria toxin gene.

In other embodiments, the second ORF sequence is a prodrug activating gene (e.g., drug-susceptibility or suicide gene) that codes for a protein that converts a prodrug that lacks a therapeutic effect into a drug which renders a cell expressing said gene susceptible to death following exposure to said prodrug. Examples of pro-drug genes include the thymidine kinase of Herpes Simplex Virus (HSV-tk), cytochrome P450, human deoxycytidine kinase and the bacterial enzymes cytosine deaminase and guanine phosphoribosyl transferase (gpt) genes. Cells that express these genes are rendered sensitive to the prodrugs ganciclovir (HSV-tk), cyclophosphamide (cytochrome P450), cytosine arabinoside (deoxycytidine kinase), 5-fluorocytosine (bacterial cytosine deaminase) or thioxanthine (gpt). In a preferred embodiment, the prodrug activating gene is the HSV-tk gene which can also provide an important therapeutic advantage. During TK catalysis of the antiviral guanosine analogue ganciclovir, apoptotic molecules are released that kill surrounding cells by a process termed "bystander" killing. A limited number of target cells may initially express the HSV-tk gene, this localized cytocidal effect provides a therapeutic effect to adjacent non-expressing, undesired bystander cells.

It has been found that the expression level of the second polypeptide expressed from the IRES can be lower than expected. However, co-infection of a recipient cell with an expression vector expressing the second open-reading frame from another promoter that is not an IRES results in synergistic expression of the second open-reading frame. Accordingly, one aspect of the disclosure encompasses embodiments of a method of modulating the proliferation or viability of a neuroendocrine tumor by co-infecting the target tumor To increase the treatment options for insulinoma patients, a conditionally replicating adenovirus has been generated that can specifically replicate and express therapeutic genes in neuroendocrine (NE) tumors. The promoter-specific expression of these adenoviruses is regulated upstream by an INSM1 (insulinoma-associated-1) promoter that is silent in normal adult tissues but active in developing NE cells and NE tumors. By placing the INSM1-promoter with an insulator (HS4) and two copies of neuronal restrictive silencer elements (NRSEs) in an adenoviral vector, the construct can retain tumor specificity and drive expression of a mutated adenovirus E1A gene (Δ24E1A) and the herpes simplex virus thymidine kinase (HSV-tk) gene. Data obtained using pancreatic cell lines in vitro and a subcutaneous mouse tumor model revealed that the INSM1-promoter driven viruses were able to replicate specifically in the INSM1-positive cells. INSM1-specific HSV-tk expression in combination with ganciclovir treatment displayed dose-dependent tumor cell killing in insulinomas, leaving INSM1-negative cells unharmed. When the INSM1-promoter driven HSV-tk was combined with Δ24E1A and INSM1p-HSV-tk (K5) viruses, the co-infected insulinoma expressed higher levels of HSV-tk and more efficient tumor suppression as compared to the INSM1p-HSV-tk virus alone. Taken together, INSM1p-driven conditionally replicating adenoviruses represent a new tool for the treatment of insulinoma that provides clinician additional options to combat this disease.

Accurate detection of neuroendocrine (NE) tumors is critically important for better prognosis and treatment outcomes in patients. To demonstrate the efficacy of using an adenoviral vector for the detection of NE tumors, a pair of adenoviral vectors was constructed that in combination can conditionally replicate and release *Gaussia* luciferase into the circulation after infecting the NE tumors. The expression of these two vectors is regulated upstream by an INSM1-promoter (insulinoma-associated-1) that is specifically active in NE tumors and developing NE tissues, but silenced in normal adult tissues. To retain the tumor-specificity of the INSM1 promoter, the promoter was modified using the core insulator sequence from the chicken β-globin HS4 insulator and the neuronal restrictive silencing element (NRSE). This modified INSM1-promoter can retain NE tumor specificity in an adenoviral construct while driving a mutated adenovirus E1A gene (Δ24E1A), the *Metridia*, or *Gaussia* luciferase gene.

The in vitro cell line and mouse xenograft human tumor studies revealed the NE specificity of the INSM1-promoter in NE lung cancer, neuroblastoma, medulloblastoma, retinoblastoma, and insulinoma. When the INSM1-promoter driven *Gaussia* luciferase was combined with Δ24E1A, the co-infected NE tumor secreted higher levels of *Gaussia* luciferase as compared to the INSM1p-*Gaussia* virus alone. In a mouse subcutaneous xenograft tumor model, the combination viruses secreted detectable level of *Gaussia* luciferase after infecting an INSM1-positive NE lung tumor for at least 12 days. Therefore, the INSM1-promoter specific conditional replicating adenovirus represents a sensitive diagnostic tool to aid clinicians in the detection of NE tumors.

One aspect of the disclosure, therefore, encompasses embodiments of a neuroendocrine tumor-specific viral expression vector whose genome comprises: (a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8; (b) an insulator region upstream from said promoter, wherein said insulator region comprises an insulator element or a tandem pair of core insulator elements; (c) a pair of tandem neuronal restrictive silencer elements (NRSE) downstream from said promoter; (d) an IRES element operatively linked upstream of one or more open reading frame nucleotide sequences encoding at least one of a polypeptide toxin lethal or conditionally lethal to cells in which the toxin is expressed and a secreted bioluminescent reporter molecule; and (e) at least one nucleotide sequence encoding a 3'-untranslated region, wherein: (i) said insulator region is adapted to block the influence of viral regulatory elements on the transcription within mammalian cells of said one or more nucleotide sequences, but not to affect the influence of the INSM1 promoter or the influence of the neuronal restrictive silencer elements on the transcription of said one or more polypeptide encoding nucleotide sequences; (ii) said INSM1 promoter is adapted to cause the selective transcription of said one or more nucleotide sequences in tumor cells of neuroendocrine origin; and (iii) said pair of tandem neuronal restrictive silencer elements are operatively linked to the INSM1 promoter, and are adapted to selectively repress the transcription of said one or more nucleotide sequences in non-neuronal cells.

In some embodiments of this aspect of the disclosure, the open reading frame nucleotide sequence operably linked to the IRES element can encode the conditionally lethal toxin herpes simplex virus thymidine kinase (HSV-tk).

In some embodiments of this aspect of the disclosure, the secreted bioluminescent reporter molecule can be a luciferase 2, a *Renilla* luciferase, a *Metridia* luciferase, or a *Gaussia* luciferase.

In some embodiments of this aspect of the disclosure, the viral expression vector can be a non-replicating Ad5 adenoviral vector.

In some embodiments of this aspect of the disclosure, the human INSM1 promoter comprises a nucleotide sequence having at least 95% similarity to SEQ ID NO: 1, the insulator region is a chicken HS4 β-globin insulator element comprising a nucleotide sequence having at least 95% similarity to SEQ ID NO: 3 or a pair of tandem core chicken HS4 β-globin insulator elements, each of said core elements comprising a nucleotide sequence having at least 95% similarity to SEQ ID NO: 4, the pair of tandem neuronal restrictive silencer elements comprises a nucleotide sequence having at least 95% similarity to SEQ ID NO: 2, the nucleotide sequence operably linked to the INSM1 promoter has at least 95% similarity to SEQ ID NO: 7 and encodes the tumor-selective modified E1A polypeptide Δ24E1A, the IRES element has the nucleotide sequence having at least 95% similarity to SEQ ID NO: 6; and the 3'-untranslated region has a nucleotide sequence having at least 95% similarity to SEQ ID NO: 10.

In some embodiments of this aspect of the disclosure, the nucleotide sequence operably linked to the IRES element can have a nucleotide sequence having at least 95% similarity to SEQ ID NO: 9 and encoding the herpes simplex virus thymidine kinase (HSV-tk).

In some embodiments of this aspect of the disclosure, the viral expression genome can comprise the nucleotide sequence having at least 95% similarity to SEQ ID NO: 11.

Another aspect of the disclosure encompasses embodiments of a composition comprising a first neuroendocrine tumor-specific viral expression vector whose genome comprises: (a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8; (b) an insulator region upstream from said promoter, wherein said insulator region comprises an insulator element or a tandem pair of core insulator elements; (c) a pair of tandem neuronal restrictive silencer elements (NRSE) downstream from said promoter; (d) an IRES element operatively linked upstream of one or more open reading frame nucleotide sequences encoding at least one of a polypeptide toxin lethal or conditionally lethal to cells in which the toxin is expressed and a secreted bioluminescent reporter molecule; and (e) at least one nucleotide sequence encoding a 3'-untranslated region, wherein: (i) said insulator region is adapted to block the influence of viral regulatory elements on the transcription within mammalian cells of said one or more nucleotide sequences, but not to affect the influence of the INSM1 promoter or the influence of the neuronal restrictive silencer elements on the transcription of said one or more polypeptide encoding nucleotide sequences; (ii) said INSM1 promoter is adapted to cause the selective transcription of said one or more nucleotide sequences in tumor cells of neuroendocrine origin; and (iii) said pair of tandem neuronal restrictive silencer elements are operatively linked to the INSM1 promoter, and are adapted to selectively repress the transcription of said one or more nucleotide sequences in non-neuronal cells.

In some embodiments of this aspect of the disclosure, the nucleotide sequence operably linked to the IRES element can encode the conditionally lethal toxin herpes simplex virus thymidine kinase (HSV-tk).

In some embodiments of this aspect of the disclosure, the secreted bioluminescent reporter molecule can be a luciferase 2, a *Renilla* luciferase, a *Metridia* luciferase, or a *Gaussia* luciferase.

In some embodiments of this aspect of the disclosure, the viral expression vector can be a non-replicating Ad5 adenoviral vector.

In some embodiments of this aspect of the disclosure, the human INSM1 promoter can comprise a nucleotide sequence having at least 95% similarity to SEQ ID NO: 1, the insulator region can be a chicken HS4 β-globin insulator element comprising a nucleotide sequence having at least 95% similarity to SEQ ID NO: 3 or a pair of tandem core chicken HS4 β-globin insulator elements, each of said core elements comprising a nucleotide sequence having at least 95% similarity to SEQ ID NO: 4, the pair of tandem neuronal restrictive silencer elements can comprise a nucleotide sequence having at least 95% similarity to SEQ ID NO: 2, the nucleotide sequence operably linked to the INSM1 promoter can have at least 95% similarity to SEQ ID NO: 7 and encode the tumor-selective modified E1A polypeptide Δ24E1A, an IRES element can have the nucleotide sequence having at least 95% similarity to SEQ ID NO: 6; and the 3'-untranslated region can have a nucleotide sequence having at least 95% similarity to SEQ ID NO: 10.

In some embodiments of this aspect of the disclosure, the composition can further comprise the herpes simplex virus thymidine kinase (HSV-tk) having the nucleotide sequence having at least 95% similarity to SEQ ID NO: 9.

In some embodiments of this aspect of the disclosure, the viral expression genome can comprise the nucleotide sequence having at least 95% similarity to SEQ ID NO: 11.

In some embodiments of this aspect of the disclosure, the composition can further comprise a pharmaceutically acceptable carrier.

In some embodiments of this aspect of the disclosure, the composition can further comprise a second neuroendocrine tumor-specific viral expression vector, the genome of said second viral expression vector comprising: (a) a human Insulinoma-associated 1 promoter (INSM1p) operatively linked to a nucleotide sequence encoding a polypeptide toxin lethal or conditionally lethal to cells in which the toxin is expressed and a polypeptide reporter molecule; (b) an insulator region upstream from said promoter, wherein said insulator region comprises an insulator element or a tandem pair of core insulator elements; (c) a pair of tandem neuronal restrictive silencer elements downstream from said promoter; and (d) a nucleotide sequence encoding a 3'-untranslated region, wherein: (i) said second viral expression vector is competent to infect at least some mammalian cells; (ii) said insulator region is adapted to block the influence of viral regulatory elements on the transcription within mammalian cells of said one or more nucleotide sequences, but not to affect the influence of said promoter or the influence of said neuronal restrictive silencer elements on the transcription of said one or more nucleotide sequences; (iii) said INSM1 promoter is adapted to cause the selective transcription of said one or more nucleotide sequences in tumor cells of neuroendocrine origin; and (iv) said tandem neuronal restrictive silencer elements are operatively linked to said promoter, and are adapted to selectively repress the transcription of said one or more nucleotide sequences in non-neuronal cells; wherein the level of expression of the polypeptide toxin or the polypeptide reporter molecule from the combination of the first and second vectors in a recipient cell is synergistically greater compared to expression from the first or second vector alone.

In some embodiments of this aspect of the disclosure, the first and the second viral expression vectors can each express the conditionally lethal toxin herpes simplex virus thymidine kinase (HSV-tk).

In some embodiments of this aspect of the disclosure, the first and the second viral expression vectors can each express a reporter molecule.

In some embodiments of this aspect of the disclosure, the first and the second viral expression vectors are each genetically modified non-replicating Ad5 adenoviral vectors.

In some embodiments of this aspect of the disclosure, the composition can be formulated for directed delivery to a tumor, intravenous delivery to a tumor, or respiratory delivery to a lung tumor.

Yet another aspect of the disclosure encompasses embodiments of a method of increasing the tumor-specific expression of a polypeptide from a viral vector, said method comprising delivering to a neuroendocrine tumor cell or tumor a first neuroendocrine tumor-specific viral expression vector whose genome comprises: (a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8; (b) an insulator region upstream from said promoter, wherein said insulator region comprises an insulator element or a tandem pair of core insulator elements; (c) a pair of tandem neuronal restrictive silencer elements (NRSE) downstream from said promoter; (d) an IRES element operatively linked upstream of one or more open reading frame nucleotide sequences encoding at least one of a polypeptide toxin lethal or conditionally lethal to cells in which the toxin is expressed and a secreted bioluminescent reporter molecule; and (e) at least one nucleotide sequence encoding a 3'-untranslated region wherein: (i) said insulator region is adapted to block the influence of viral regulatory elements on the transcription within mammalian cells of said one or more nucleotide sequences, but not to affect the influence of the INSM1 promoter or the influence of the neuronal restrictive silencer elements on the transcription of said one or more polypeptide encoding nucleotide sequences; (ii) said INSM1 promoter is adapted to cause the selective transcription of said one or more nucleotide sequences in tumor cells of neuroendocrine origin; and (iii) said pair of tandem neuronal restrictive silencer elements are operatively linked to the INSM1 promoter, and are adapted to selectively repress the transcription of said one or more nucleotide sequences in non-neuronal cells.

In some embodiments of this aspect of the disclosure, the method can further comprise delivering to the neuroendocrine tumor cell or tumor a second neuroendocrine tumor-specific viral expression vector, the genome of said second viral expression vector comprising: (a) a human Insulinoma-associated 1 promoter (INSM1p) operatively linked to a nucleotide sequence encoding a polypeptide toxin lethal or conditionally lethal to cells in which the toxin is expressed and a polypeptide reporter molecule; (b) an insulator region upstream from said promoter, wherein said insulator region comprises an insulator element or a tandem pair of core insulator elements; (c) a pair of tandem neuronal restrictive silencer elements downstream from said promoter; and (d) a nucleotide sequence encoding a 3'-untranslated region, wherein: (i) said second viral expression vector is competent to infect at least some mammalian cells; (ii) said insulator region is adapted to block the influence of viral regulatory elements on the transcription within mammalian cells of said one or more nucleotide sequences, but not to affect the influence of said promoter or the influence of said neuronal restrictive silencer elements on the transcription of said one or more nucleotide sequences; (iii) said INSM1 promoter is adapted to cause the selective transcription of said one or more nucleotide sequences in tumor cells of neuroendocrine origin; and (iv) said tandem neuronal restrictive silencer elements are operatively linked to said promoter, and are adapted to selectively repress the transcription of said one or more nucleotide sequences in non-neuronal cells; wherein the level of expression of the at least one of the polypeptide toxin and the polypeptide reporter molecule from the combination of the first and second vectors in the recipient cell or tumor is synergistically greater compared to expression from the first or second vector alone.

In some embodiments of this aspect of the disclosure, the first and second viral vectors can be delivered to the recipient cell or tumor sequentially.

In some embodiments of this aspect of the disclosure, the first and second viral vectors can be co-delivered in a single pharmaceutically acceptable composition.

In some embodiments of this aspect of the disclosure, the first neuroendocrine tumor-specific viral expression vector the human INSM1 promoter can comprise a nucleotide sequence having at least 95% similarity to SEQ ID NO: 1, the insulator region can be a chicken HS4 β-globin insulator element comprising a nucleotide sequence having at least 95% similarity to SEQ ID NO: 3 or a pair of tandem core chicken HS4 β-globin insulator elements, each of said core elements comprising a nucleotide sequence having at least 95% similarity to SEQ ID NO: 4, the pair of tandem neuronal restrictive silencer elements can comprise a nucleotide sequence having at least 95% similarity to SEQ ID NO: 2, the nucleotide sequence operably linked to the INSM1 promoter can have at least 95% similarity to SEQ ID NO: 7 and encode the tumor-selective modified E1A polypeptide Δ24E1A, the IRES element can have the nucleotide sequence having at least 95% similarity to SEQ ID NO: 6; and the 3'-untranslated region can have a nucleotide sequence having at least 95% similarity to SEQ ID NO: 10.

In some embodiments of this aspect of the disclosure, the nucleotide sequence operably linked to the IRES element can have a nucleotide sequence having at least 95% similarity to SEQ ID NO: 9 and encodes the herpes simplex virus thymidine kinase (HSV-tk).

In some embodiments of this aspect of the disclosure, the first neuroendocrine tumor-specific viral expression genome can comprise a nucleotide sequence having at least 95% similarity to SEQ ID NO: 11.

In some embodiments of this aspect of the disclosure, the second neuroendocrine tumor-specific viral expression vector the human INSM1 promoter can comprise a nucleotide sequence having at least 95% similarity to SEQ ID NO: 1, the insulator region can be a chicken HS4 β-globin insulator element comprising a nucleotide sequence having at least 95% similarity to SEQ ID NO: 3 or a pair of tandem core chicken HS4 β-globin insulator elements, each core element comprising a nucleotide sequence having at least 95% similarity to SEQ ID NO: 4, the pair of tandem neuronal restrictive silencer elements can comprise a nucleotide sequence having at least 95% similarity to SEQ ID NO: 2, the nucleotide sequence operably linked to the INSM1 promoter can have a nucleotide sequence having at least 95% similarity to SEQ ID NO: 9 and encode the herpes simplex virus thymidine kinase (HSV-tk), and the 3'-untranslated region can have a nucleotide sequence having at least 95% similarity to SEQ ID NO: 10.

In some embodiments of this aspect of the disclosure, at least one of the viral expression vectors thereof can encode a reporter molecule, and the method further comprises observing subsequent expression of the encoded reporter molecule in the patient's tissues as a measure of the presence or the extent of a neuroendocrine tumor.

In some embodiments of this aspect of the disclosure, the reporter molecule can be *Gaussia* luciferase and a nucleotide sequence encoding said luciferase has at least 95% similarity to SEQ ID NO: 5.

In some embodiments of this aspect of the disclosure, the first and second neuroendocrine tumor-specific viral expression vectors can each comprise a nucleotide sequence encoding a polypeptide toxin and wherein, if said polypeptide toxin is only conditionally lethal, then said method additionally can comprise the step of providing conditions that produce the lethal phenotype; whereby cells of the neuroendocrine tumor are selectively killed.

In some embodiments of this aspect of the disclosure, the method can further comprise contacting the neuroendocrine cell with ganciclovir thereby selectively killing cells of the neuroendocrine tumor.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Tumor-specific promoter driven therapy for neuroendocrine tumors: Insulinomas are a rare type of neuroendocrine (NE) tumor, but they are the most common type of tumors arising from pancreatic islet cells. The majority of beta cell tumors are benign, but malignant insulinomas can occur and are highly aggressive tumors that have a 63% 5-year recurrence rate and an average survival of less than 4 years (Proye Calif. (1998) *Aust. N. Z. J. Surg.* 68: 90-100). Moreover, the uncontrolled insulin secretion from these tumors often leads to complications arising from hyperinsulinemia and hypoglycemia. Effective treatment of aggressive and recurring insulinomas is imperative for better clinical outcomes in these patients.

A tumor-specific promoter (insulinoma-associated-1, INSM1) has been identified that drives a NE-specific tumor marker that was discovered using a human insulinoma subtractive library (Goto et al., (1992) *J. Biol. Chem.* 267: 15252-15257). The INSM1-promoter regulates expression of a zinc-finger transcription factor that is highly specific to NE tumors (Lan & Breslin (2009) *FASEB J.* 23: 2024-2033). Insm1 knockout models have shown that Insm1 expression is important for the formation of endocrine pancreas and sympatho-adrenal lineage cells during early embryonic development (Gierl et al., (2006) *Genes Dev.* 20: 2465-2478; Wildner et al., (2008) Development 135:473-481). When the animal reached adulthood, Insm1 expression could no longer be detected in all normal adult tissues. However, the INSM1 gene was re-activated in most human NE tumors including neuroblastomas, pheochromacytoma, retinoblastomas, medulloblastomas, pituitary carcinomas, small cell lung carcinomas, carcinoid tumors, and insulinomas (Wang et al., (2009) *Human Gene Ther.* 20: 1308-1318).

The original INSM1-promoter loses tumor specificity when used in an adenoviral vector delivery system. Through a series of modifications using the HS4 chicken β-globin insulator and neuron-restrictive silencer elements (NRSEs) to insulate the promoter against viral enhancers, the modified INSM1 promoter was able to retain specificity to drive adenoviral expression specifically in NE tumors (Akerstrom et al., (2012) *Cancer Gene Ther.* 19: 828-838).

To take advantage of the NE tumor specificity of the INSM1 promoter, an oncolytic adenoviral vector has been constructed that can express both herpes simplex virus thymidine kinase (HSV-tk) and the Δ24E1A gene with an internal ribosomal entry site (IRES) to act as a therapeutic vector in combination with ganciclovir (GCV) treatment (Moolten et al., (1990) *Human Gene Ther* 1:125-134).

The Δ24E1A mutant is a mutated form of the adenovirus E1A gene essential for viral replication. Due to a 24-base pair deletion, the E1A protein loses its ability to bind retinoblastoma (Rb) protein, resulting in a virus that relies on Δ24E1A for replication solely in Rb negative cancer cells (Whyte et al., (1988) *Nature* 334:124-129). The specificity of the Δ24E1A mutant along with the specificity of the INSM1 promoter creates a dual layer of safety for the adenoviral vector. The Ad-INSM1p-HSV-tk (K5), Ad-INSM1p-Δ24E1A-IRES-HSV-tk, constructs and the combination of these two vectors were tested to treat insulin secreting tumors using both in vitro cell culture and in vivo xenograft mouse models.

Figure 1:
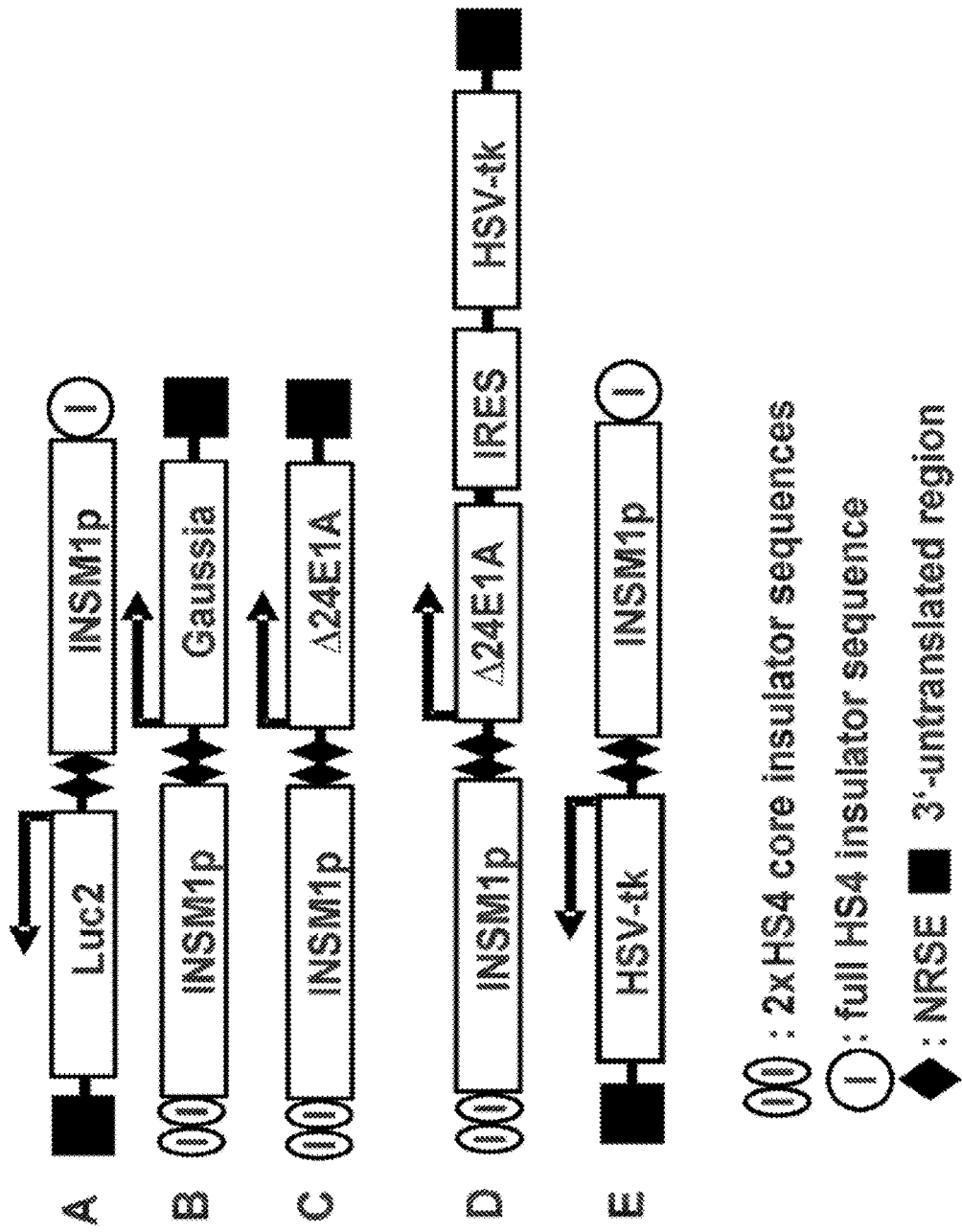
FIG. 1 schematically illustrates the oncolytic and non-oncolytic adenoviral vectors of the disclosure, and their constituent regions.

Cloning the INSM1-promoter driven adenoviral constructs. The Ad-INSM1p-HSV-tk construct (K5) contained a modified INSM1 promoter with a full HS4 chicken β-globin insulator sequence (1.2 kb) upstream and two tandem NRSE sequences downstream (FIG. 1E) (Akerstrom et al., (2012) *Cancer Gene Ther* 19:828-838). To generate a new bicistronic oncolytic adenoviral vector, extra space was required for the addition of the IRES element and the Δ24E1A gene. The full HS4 chicken β-globin insulator was replaced with 2 copies of the core insulator sequence (250 bp) (SEQ ID NO: 2) to shorten the modified INSM1 promoter by approximately 700 base pairs (FIG. 1D). This new second generation modified INSM1 promoter was able to retain the same tumor specificity as the first generation modified INSM1 promoter.

Figure 12C:
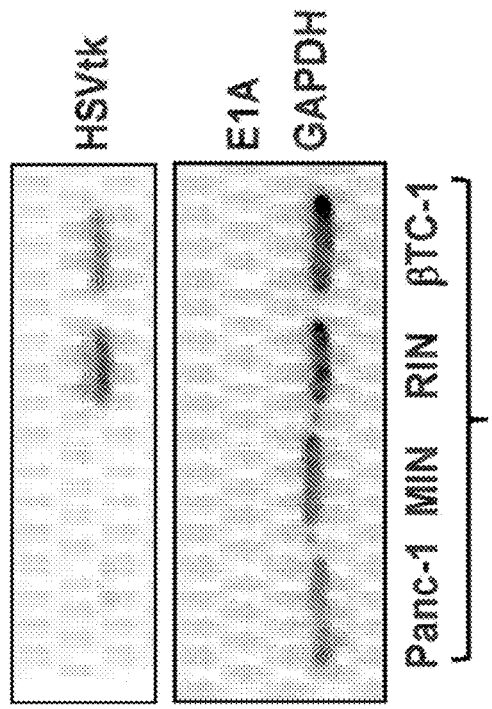
Figure 12B:
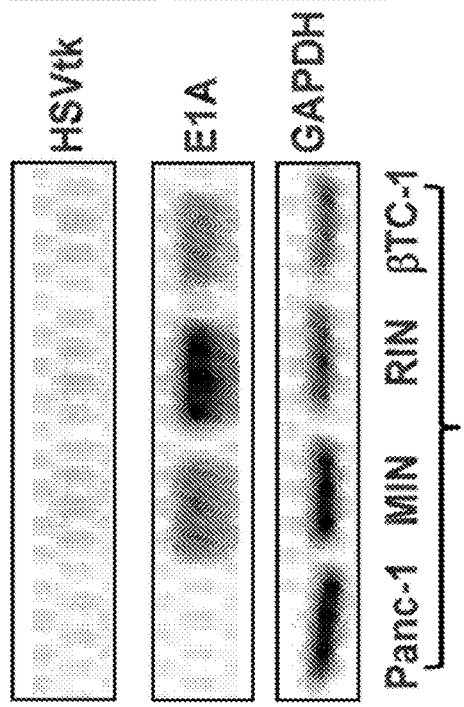

The conditionally replicating Ad-INSM1p-ΔE1A-IRES-HSV-tk vector can replicate in an INSM1-positive cell after infection. To test the ability of the conditionally replicating virus to replicate inside an INSM1-positive cell, a viral titer assay was performed by infecting RIN cells with Ad-INSM1p-ΔE1A-IRES-HSV-tk, the non-replicating Ad-INSM1p-HSV-tk (K5), or a combination of the two viruses (FIG. 12A). As negative control, virus was added to a blank well without cells. After 3 days, the viral titer for the conditionally replicating virus or the viral combination increased by approximately 3-4-fold as compared to the negative or K5 control. The non-replicating virus displayed no significant change in viral titer in a cell-free medium. The comparison of HSV-tk expression in non-oncolytic versus oncolytic adenoviral vectors. To determine the viral protein expression levels of the replicating Ad-INSM1p-ΔE1A-IRES-HSV-tk virus and the non-replicating Ad-INSM1p-HSV-tk virus (K5), Western blot analysis was conducted to detect expression of HSV-tk and Δ24E1A after infection in RIN, MIN, βTC-1 (INSM1-positive cells), and Panc-1 cells (INSM1-negative cells). Results showed that Ad-INSM1p-ΔE1A-IRES-HSV-tk expressed lower levels of HSV-tk than the non-replicating Ad-INSM1-HSV-tk virus (FIG. 12B, 12C). As expected HSV-tk and Δ24E1A protein expression are not detected in Panc-1 cells.

The difference in HSV-tk expression between the two viruses was hypothesized to be due to the location of the HSV-tk gene downstream of the IRES element sequence in the replicating virus. Therefore, to improve the HSV-tk expression levels while retaining replication competency, the non-replicating Ad-INSM1p-HSV-tk virus and the conditionally replicating Ad-INSM1p-ΔE1A-IRES-HSV-tk virus were mixed at a ratio of 1:1.

Figure 12E:
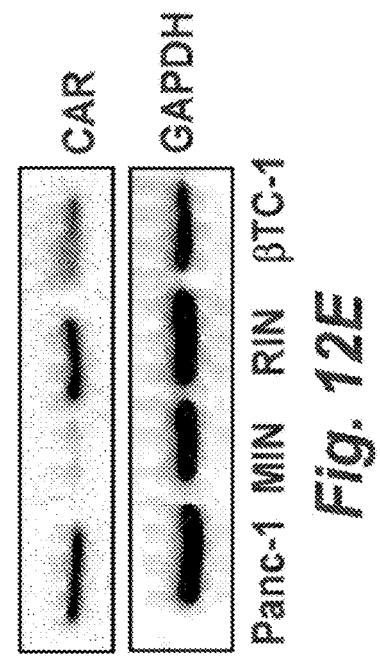
Figure 12D:
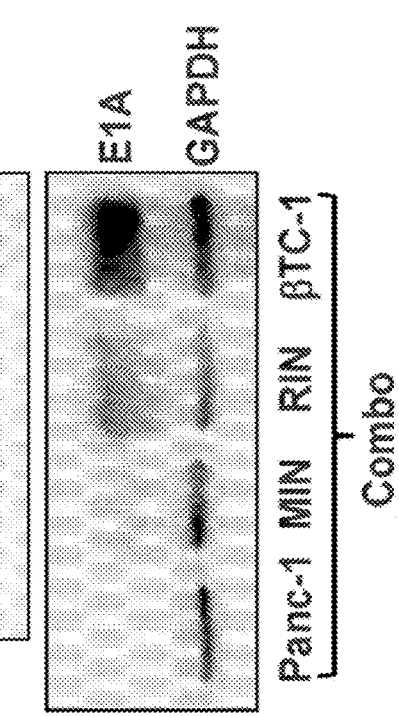

Western blots showed that HSV-tk expression was higher in the group treated with the virus combination than the Ad-INSM1p-HSV-tk virus alone (FIG. 12B, 12D), even though the total number of infectious particles remained constant at the start of the infection in both groups. Comparison of Δ24E1A expression in the combination virus versus the Ad-INSM1p-ΔE1A-IRES-HSV-tk virus alone revealed that expression of Δ24E1A was reversed in intensity between RIN and βTC-1 cells (FIG. 12B, 12D). Since adenovirus type 5 infection depends primarily upon expression of the coxsackievirus and adenovirus receptor (CAR) on the cell surface, the low thymidine kinase expression in MIN cells may be due to the low expression of CAR, limiting viral entry into the cells (FIG. 12E).

Oncolytic virus in combination with Ad-INSM1p-HSV-tk increased efficacy of insulinoma killing. Since it was established that a combination of the Ad-INSM1p-HSV-tk and Ad-INSM1p-ΔE1A-IRES-HSV-tk viruses can increase suicide gene expression and viral titer, the efficacy of this combination viral therapy in endocrine and non-endocrine pancreatic cells was examined. A cell survival assay was performed using two different treatment plans to separate the viral oncolytic effect and the HSV-tk/GCV killing.

In the first treatment plan, virus titer was increased (MOI: 0-100) while the GCV concentration was kept constant (100 μM). As viral concentration increased, a dose-dependent increase in cell killing was observed in INSM1-positive insulinoma cells infected with Ad-INSM1p-HSV-tk, Ad-INSM1p-ΔE1A-IRES-HSV-tk, and the virus combination (FIGS. 13C, 13B, 13D). The original Ad-INSM1p-HSV-tk virus (K5) alone reached maximum killing at 100 MOI, Ad-INSM1p-ΔE1A-IRES-HSV-tk virus alone reached maximum killing at 50 MOI, whereas combination virus reached maximum killing at 10 MOI.

When a non-therapeutic non-oncolytic virus such as Ad-INSM1p-Luc2 was used, no significant changes in cell survival were observed (FIG. 13A). In all cases, the INSM-promoter driven virus displayed specificity to INSM1-positive cells, sparing the INSM1-negative Panc-1 cells.

The potency of tumor cell killing across each viral treatment was compared and it was found that the combination of viral therapy reached maximum killing effect at a lower concentration (M01:10) than the other two viruses alone (FIG. 13D). The virus combination was able to reach the same level of tumor cell killing with an MOI that was 5-10-fold lower than the conditionally replicating Ad-INSM1p-ΔE1A-IRES-HSV-tk or K5 virus alone. This result is consistent with FIG. 12C that the HSV-tk and E1A expression levels were greatly increased in the combination virus group to enhance the killing effects.

Figure 14A:
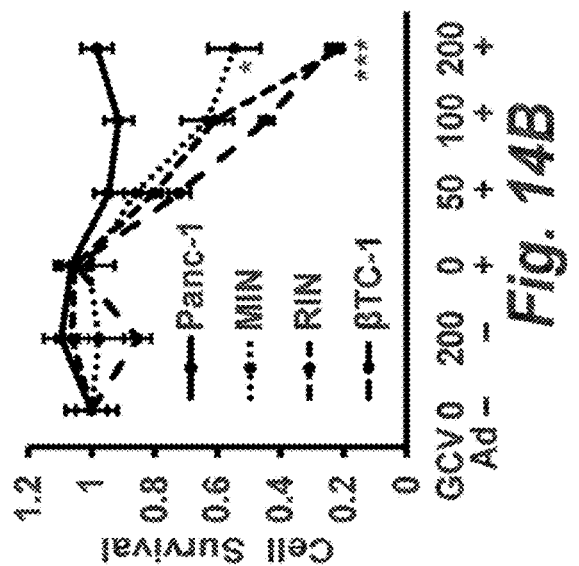
FIGS. 14A-14D illustrate that the Ad-INSM1p-HSV-tk virus in combination with the oncolytic virus kills tumor cells in a GCV dose-dependent manner. An MTS assay was conducted with three insulinoma cell lines: RIN, MIN, β-TC1 (all INSM1$^+$ insulinoma), and Panc-1 (INSM1$^-$ pancreatic epithelioid carcinoma).

To further examine the effects of the therapeutic benefits of the viral vectors of the present disclosure, a second treatment plan was devised to explore the effects of GCV drug action with its activating enzyme HSV-tk. The GCV effect (200 μM) was tested without virus or increasing the GCV concentration (0-200 μM) at a constant viral MOI of 50. Under this regimen, a significant increase of killing in all virus groups was detected except with the Ad-INSM1p-Luc2 control (FIG. 14A). Viral specificity was preserved by the INSM1 promoter, killing only INSM1-positive cells and leaving INSM1-negative Panc-1 cells unaffected.

Figure 14B:
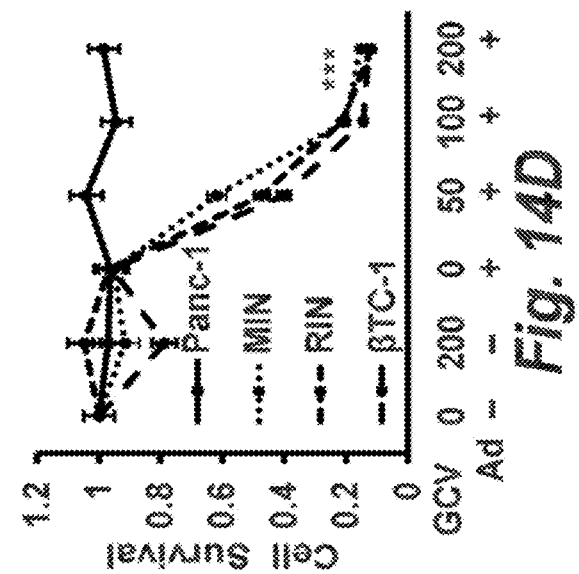
Figure 14C:
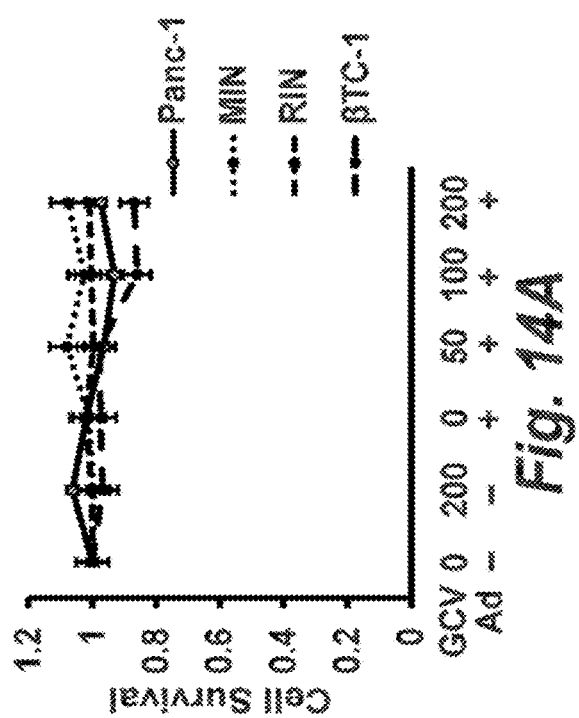
Figure 14D:
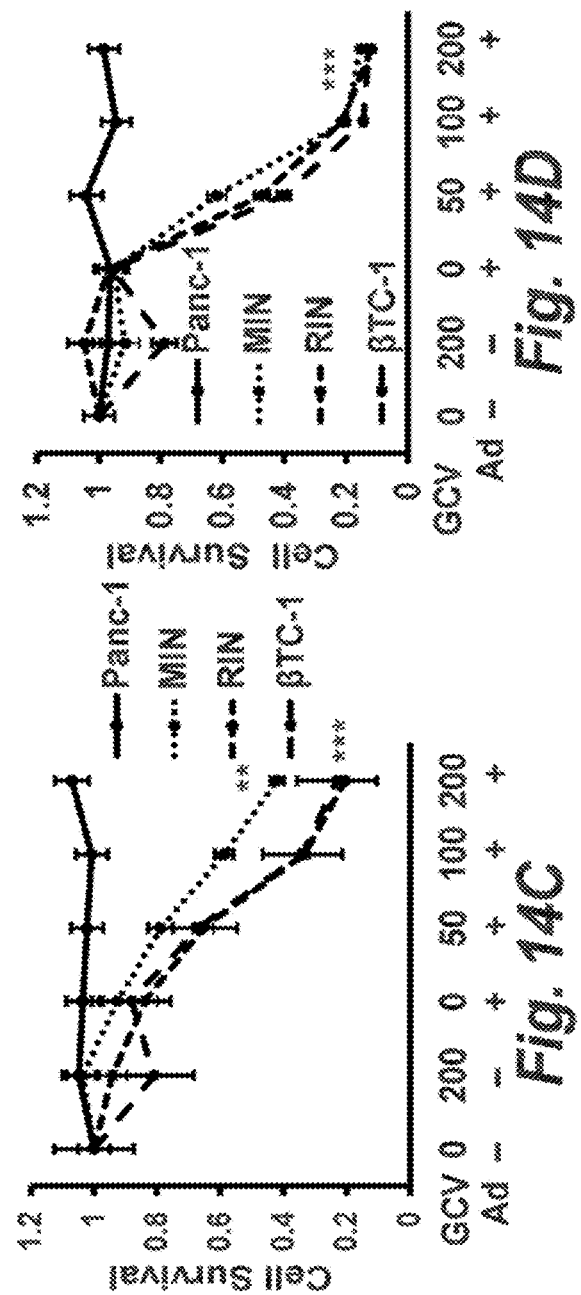

When tumor killing from either virus alone or the combination of viruses was compared it was observed that the non-replicating Ad-INSM1p-HSV-tk virus showed similar efficacy to the conditionally replicating Ad-INSM1p-ΔE1A-IRES-HSV-tk virus (FIGS. 14C and 14B). When the two viruses were combined, efficacy increased by approximately 2-fold (FIG. 14D). Interestingly, GCV by itself in the inactive form can also be toxic to cells, demonstrated in particular by the decrease in survival of RTC-1 cells when treated with 200 μM GCV in the absence of adenovirus.

The Ad-INSM1p-HSV-tk and Ad-INSM1p-ΔE1A-IRES-HSV-tk virus combination delayed hyperinsulinemia in vivo. The efficacy of the virus combination in vitro was tested for its function in an in vivo xenograft tumor model. RIN cells were infected with 10 MOI Ad-INSM1p-Luc2 for 24 hours in vitro to label the cells for subsequent visualization. RIN tumor cells were injected into 6-8 week old Nu/Nu mice and allowed to establish for a period of 48 hours. After this period, Ad-INSM1p-Luc2 ($1\times10^9$ ifu) or a combination of Ad-INSM1p-ΔE1A-HSV-tk and Ad-INSM1p-HSV-tk ($5\times10^8$ ifu each) were introduced by direct injection into the same location as injected tumor cells (previously marked with Luc2). Daily GCV treatment was started 3 days after the introduction of the virus.

In the mice treated with the non-therapeutic Ad-INSM1p-Luc2 virus, blood glucose levels dropped sharply as early as 4 days and continued to drop below 20 mg/dL without recovery (FIG. 15A). Survival of these mice did not last for longer than two weeks, and the luciferase imaging showed the presence of the infected tumor cells for the duration of the experiment (FIG. 15B). In the mice treated with the combination virus, hypoglycemia was delayed in some cases and improved survival to up to 16 days (FIG. 15A). In one case, hypoglycemia was prevented for the duration of the experiment. Using luciferase activity, it was observed that tumor size decreased in mice treated with the combination virus, leading to the prevention or delay of hypoglycemia (FIG. 15C).

Figure 16:
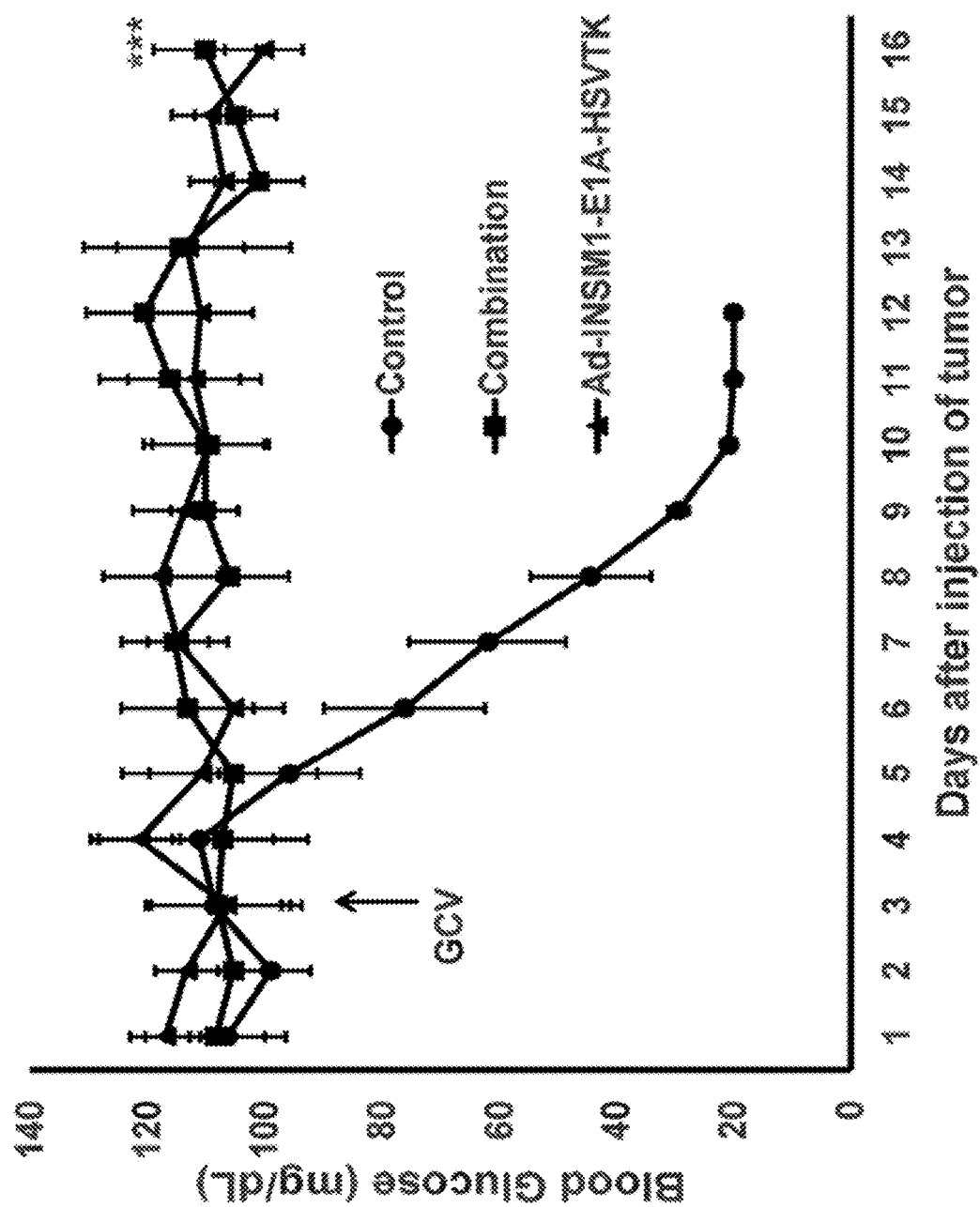
FIG. 16 is a graph illustrating pre-infection with the combination virus in an in vivo subcutaneous mouse xenograft tumor model. RIN cells were pre-treated with 10 MOI of Ad-INSM1p-Luc2 or combination of Ad-INSM1p-HSV-tk and Ad-INSM1p-E1A-HSV-tk viruses (5 MOI each). After 24 hours of incubation, $10^9$ cells were injected subcutaneously into the right flank of 4 week old Nu/Nu mice. GCV treatment was started 3 days after injection (arrow) to allow for viral replication to occur inside the tumor cells. Blood glucose was measured daily via tail vein. (n=5).

Pre-infection with Ad-INSM1p-HSV-tk and Ad-INSM1p-ΔE1A-IRES-HSV-tk virus combination displayed cancer specific killing in vivo. To test the viral vector with an alternative delivery method, RIN cells were pre-infected with 10 MOI of the therapeutic combination viruses of the disclosure before injecting them subcutaneously into Nu/Nu mice (FIG. 16). In the control group treated with the non-therapeutic Ad-INSM1p-Luc2 virus, blood glucose levels began to decrease by day 4 post-injection and continued to decline rapidly without recovery. In contrast, mice in the group treated with either the Ad-INSM1p-ΔE1A-IRES-HSV-tk virus alone or the combination virus and GCV (from day 3) did not experience significant changes in blood glucose for the duration of the experiment, suggesting that HSV-tk/GCV suppresses insulinoma tumor growth and prevents hypoglycemia.

Discussion

Originally, the study focused primarily on the efficacy of the newly constructed conditionally replicating Ad-INSM1p-ΔE1A-IRES-HSV-tk virus in comparison with the previously tested non-replicating Ad-INSM1p-HSV-tk vector. However, Western blot analysis revealed that while the Ad-INSM1p-ΔE1A-IRES-HSV-tk construct expressed high amounts of Δ24E1A protein, it expressed significantly less HSV-tk protein than the Ad-INSM 1p-HSV-tk construct (K5).

While not wishing to be bound by anyone theory, this decrease in HSV-tk expression can be due to its dependency on the IRES element sequence. Other studies have shown that an IRES-dependent second open reading frame can have significantly lower expression than that of the first gene in a bi-cistronic expression cassette (Mizuguchi et al., (2000) Mol. Ther. 1: 376-382). To circumvent this inefficiency, a combination of both the Ad-INSM1p-HSV-tk and Ad-INSM1p-ΔE1A-IRES-HSV-tk vectors was used. The co-infection of both viruses into the same cells would not only enhance the non-replicating Ad-INSM1p-HSV-tk expression, but also retain the replicating capacity due to the presence of Δ24E1A. Using cell survival assays, it was demonstrated that the combination virus displayed a higher efficacy in tumor cell killing as compared to either viral vector alone.

Both viral vector-infected cell lysis and GCV treatment decreased cancer cell survival in a dose-dependent manner. Under conditions of constant viral concentration, the HSV-tk expressing viruses showed higher tumor cell killing at higher GCV concentrations, while non-therapeutic luciferase2 virus without HSV-tk showed no effects on cell survival. Conversely, under conditions where GCV concentration is constant and viral concentration is increased, replicating viruses displayed more efficient killing than non-replicating virus as virus MOI increased. When combined, the two groups of viruses, there was a synergistic effect that could result from the increase of viral titers and the HSV-tk suicide gene expression.

In the subcutaneous xenograft tumor model, a direct intra-tumoral injection delivery method it was determined whether the therapeutic virus combination would have any effect on tumor growth. When the tumor-bearing mice were followed, it was found that the resulting hyperinsulinemia from the engrafted tumors had a profound effect on the physiology of tumor bearing animals. As early as 7 days post-tumor cell injection, blood glucose levels dropped below 20 mg/dL and mice treated with non-therapeutic virus (control) did not survive longer than 2 weeks. In the mice treated with the combination virus, hyperinsulinemia was prevented in one subject and was delayed in two subjects by up to 16 days.

The sharp and drastic hyperinsulinemia effect caused difficulties in the timing of the treatment. The tumors did not grow large enough to be visible for injection even as blood glucose dropped significantly during the first few days after the tumor cell injection. Therefore, it was necessary to inject the viruses early at the same location that the tumor cells had been injected. Most likely, the therapeutic effect was hindered by a less effective delivery of viruses to the tumor cells.

To overcome the abrupt decrease in blood glucose and to treat the tumors in sufficient time, pre-infection of the tumor cells prior to injection was used. This method of treatment provides evidence that the INSM1 promoter is an excellent candidate for driving gene expression to treat insulinomas.

Accordingly, INSM1 promoter-driven adenoviral vectors like the Ad-INSM1p-HSV-tk and Ad-INSM1p-ΔE1A-IRES-HSV-tk viral combination can be advantageous reducing the proliferation or effects of insulinomas. In cases where patients have recurring insulinoma after surgical resection, an alternative method of treatment is required.

Materials and Methods

Cell lines and reagents. The insulinoma cell line RTC-1 was cultured in a Dulbecco Modified Eagle Medium (DMEM, low glucose) supplemented with 10% fetal bovine serum, 50 µg/mL penicillin, and 0.25 µg/mL streptomycin at 37° C. under 5% carbon dioxide. MIN, RIN, and Panc-1 cells were obtained from American type culture collection and cultured in the same medium except that the Panc-1 cells were cultured in high glucose DMEM.

Generation of oncolytic viruses. The pGL3-INSM1p plasmid contains the modified INSM1 promoter and was digested and ligated with the Δ24E1A and HSV-tk genes linked by an internal ribosomal entry site (IRES). To clone the Δ24E1A gene, site directed mutagenesis was performed on an existing E1A gene in the pJet plasmid to delete 24 base pairs from the original sequence. The HSV-tk gene was obtained from the pWS plasmid while the IRES element sequence was subcloned from the pIRES element vector (Clontech, cat. no. 631605). After ligation, the INSM1p-Δ24E1A-IRES-HSV-tk fragment was cut and placed into the pShuttle plasmid, linearized, and electroporated into BJ5183-AD-1 cells for recombination. The recombinant adenoviral DNA was transfected into AD293 cells to produce adenoviral vector and subjected to further amplification. The final viral stock was titered using the AdenoXTiter Assay (Clontech, cat. no. 632250) and purified using CsCl density gradient centrifugation.

Western blots analysis. Cells were infected at 10 MOI for 48 h with either Ad-INSM1p-ΔE1A-HSV-tk, Ad-INSM1p-HSV-tk, or a combination of the two viruses at 5 MOI each. Western blot analysis was performed using a rabbit α-HSV-tk antibody (FL-234, Santa Cruz Biotech., cat. no. sc-134475) at a concentration of 1:1000 with a secondary HRP-conjugated goat anti-rabbit antibody at a concentration of 1:10,000. Blots were then imaged with ECL substrate at an exposure time of 1 minute. After stripping of the membrane, mouse α-E1A antibody (BD Pharmingen, cat. no. 554155) was used at a concentration of 1:1000 with a secondary HRP-conjugated goat anti-mouse antibody at 1:10,000. The membrane was then imaged with ECL substrate at an exposure time less than 30 seconds.

Viral titer assay. RIN cells were seeded on a 6-well plate at a density of $2 \times 10^6$ cells/well and infected with Ad-INSM1p-ΔE1A-HSV-tk, Ad-INSM1p-HSV-tk, or a combination of the two viruses each at a half concentration ($1 \times 10^6$). Viral concentrations of either 10 MOI or 200 MOI were used for each virus group. After incubation for 3 days, cells and media were collected and viral particles were released into the media by 4 cycles of freeze-thaw lysis in a methanol dry ice bath. The viruses infected into AD293 cells were titered by immunostaining using anti-hexon antibody (Abcam, cat. no. Ab8251). The viral titer was determined using the total number of virus particles based on the volume of media that was collected.

Cell survival assay. Cell survival assays using MTS colorimetric dye were conducted using cell lines that were either INSM1-positive or -negative: RIN (INSM1$^+$ rat insulinoma), MIN, β-TC1 (both INSM1$^+$ mouse insulinoma), and Panc-1 (INSM1$^-$ pancreatic epithelioid carcinoma). These cells were plated onto a 96-well plate at a density of $10^5$ cells per well. To assess the efficacy of the combination virus versus either the non-replicating virus or the replicating virus alone, a cell survival assay was conducted using the following virus treatment groups: Ad-INSM1p-Luc2, Ad-INSM1p-HSV-tk, Ad-INSM1p-ΔE1A-IRES-HSV-tk and a combination of Ad-INSM1p-HSV-tk and AddNSM1p-ΔE1A-IRES-HSV-tk. These viruses infected cancer cells at a range of 0-200 MOI. After an incubation of 3 days, GCV was added to the cells at a constant 100 µM concentration across all viral groups and MOI ranges for five additional days. Afterwards, cell survival was assessed using CELLTITER 96® AQueous One Solution Cell Proliferation Assay (Promega, cat. no. G3582) and read at 490 nm on a Bio-Tek Synergy-HT Microplate Reader. Results were plotted as relative absorbance (relative to control sample with no virus) against increasing viral MOI. Samples were conducted in six wells each and statistical significance was determined using the students T-test with a threshold of $p<0.05$.

For a second experiment, the same viral constructs were used to infect cancer cells at a constant 50 MOI. After incubation with the virus for 3 days, GCV was added to the cells at concentrations ranging from 0-200 µM. The combination of virus and GCV prodrug was then incubated for five additional days. As control, samples with no virus and either no GCV or 200 µM GCV were used to assess the effects of GCV toxicity on cell survival. After the treatment period, cell survival was assessed using CELLTITER 96® AQueous One Solution Cell Proliferation Assay (Promega, cat. no. G3582) and read at 490 nm on a Bio-Tek Synergy-HT Microplate Reader. Results were plotted as relative absorbance (relative to the control sample with no virus and no GCV) against increasing GCV concentration. Samples were conducted in six wells each and statistical significance was determined using the students T-test with a threshold of $p<0.05$.

Mouse xenograft tumors. RIN cells were infected with 10 MOI Ad-INSM1p-Luc2 for 24 hours in vitro. After infection, a total of $5 \times 10^7$ cells in a 1:5 dilution of Matrigel (Corning, cat. no. 354248) in PBS were injected subcutaneously into the right flank of 8 to 10 week old Nu/Nu mice. After a period of 48 hours, Ad-INSM1p-Luc2 ($1 \times 10^9$ ifu) or a combination of Ad-INSM1p-ΔE1A-HSV-tk and Ad-INSM1p-HSV-tk ($5 \times 10^8$ ifu each) were introduced in the same location as tumor cells where were injected. After 3 days post-injection, daily ganciclovir treatment was administered via intraperitoneal injection. Blood glucose was monitored daily.

To perform the imaging analysis for luciferase activity, D-luciferin substrate (Biosynth, cat. no. L-8220) was prepared at a concentration of 15 mg/ml and injected intraperitoneally into mice at a dose of 150 mg/kg. Once injection was completed, the mice were anesthetized in an isofluorane chamber (2-4% by inhalation) before being transferred to a Kodak In-Vivo Multispectral FX imager (Carestream Health, Rochester, N.Y.). Using the imager's software, luminescence was acquired with a 10 minute exposure with the mice in a supine position and an X-ray image of the mice in the same position was acquired with a 30 second exposure. Imaging was performed every 3 days. To generate the complete image, the luminescence acquisition was converted into a rainbow intensity scale and superimposed onto the X-ray acquisition using ImageJ software (National Institutes of Health).

In a second experiment, RIN cells were first infected with Ad-INSM1p-Luc2, Ad-INSM1p-ΔE1A-HSV-tk, or a combination of Ad-INSM1p-ΔE1A-HSV-tk and Ad-INSM1p-HSV-tk at 10 MOI for 24 hours. After infection, $10^8$ of the pre-infected cells were suspended in a 1:5 dilution of Matrigel (Corning) in PBS and injected subcutaneously into the right flank of 8 to 10 week old Nu/Nu mice and monitored for blood glucose levels in a similar fashion. After 3 days post-injection, daily ganciclovir treatment was administered via intraperitoneal injection and blood glucose levels were monitored daily.

Statistical Analysis. Values were corrected and expressed relative to a control group. All experiments were repeated three times. Results are presented as mean±SEM. Statistical analysis was performed using wither the Student's t-test when only two groups were in the experiment or by an one-way ANOVA comparison of multiple groups using the Tukey-Kramer test with differences at p value of less than 0.05 being considered significant.

Example 2

Detection of neuroendocrine tumors using promoter-specific secreted *Gaussia* luciferase: Neuroendocrine (NE) carcinomas are rare neoplasms that can develop into highly malignant and life-threatening tumors (Rindi & Wiedenmann (2012) *Nat. Rev. Endocrinol.* 8: 54-64; Jann et al., (2011) *Cancer* 117: 3332-3341). While they share a number of genetic and phenotypic traits, NE carcinomas comprise a very heterogeneous population of tumor types that can arise in various organs throughout the body. The most common of these cancers include neuroblastomas, retinoblastomas, medulloblastomas, pituitary carcinomas, small cell lung carcinomas, and carcinoid tumors, encompassing a broad spectrum of tumors that have so far required multiple detection and treatment methods (Brodeur et al., (1993) *J. Clin. Oncol.* 11: 1466-1477; Hayes et al., (1983) *J. Pediatr.* 102: 59-62; Oyharcabal-Bourden et al., (2005) *J. Clin. Oncol.* 23: 4726-4734; Packer et al., (1999) *J. Clin. Oncol.* 17: 2127-2136; Richardson et al., (1993) *Semin. Oncol.* 20: 105-127). Despite their differences, many of these tumors express common tumor-specific markers that can identify them as NE cancers (Mountain, C. F. (1978) *Semin. Oncol.* 5: 272-279; Argiris & Murren, (2001) *Cancer J.* 7: 437-447). Consequently, early detection of these tumor markers can lead to better treatment response and outcomes.

The INSM1 gene encodes a NE tumor-specific marker that was discovered using an insulinoma subtractive hybridization screen (Goto et al., (1992) *J. Biol. Chem.* 267: 15252-15257; Lan et al., (1993) *Cancer Res.* 53: 4169-4171). The INSM1-promoter regulates the expression of INSM1, a transcription factor with a zinc-finger DNA binding domain that is highly specific for NE tumors (Breslin et al., (2002) *Nucleic Acids Res.* 30: 1038-1045). Through an Insm1 knockout mouse model, Insm1 transcription factor was found to be important in the formation of endocrine pancreas and sympatho-adrenal lineage during development (Gierl et al., (2006) *Genes Dev.* 20: 2465-2478; Wildner et al., (2008) *Development* 135: 473-481). Most interestingly, INSM1 expression was discovered to be restricted to the embryonic peripheral and central nervous system, specifically in the cells of neuroendocrine origin (Farkas et al., (2008) *Neuron* 60: 40-55). The expression pattern was detected in the embryonic tissues of pituitary, pancreas, stomach, duodenum, thymus, adrenal glands, brain, and spinal cord, which were all found to be Insm1-positive at E15.5 in mice (Xie et al., (2002) *Genomics* 80: 54-61; Mellitzer et al., (2006) EMBO J. 25: 1344-1352). However, INSM1 is silenced in normal adult tissues, but reactivated in most of the human NE tumors, including neuroblastoma, medulloblastoma, pheochromocytoma, small cell lung carcinoma, insulinomas, pituitary tumors, carcinoid tumors, medullary thyroid carcinoma, and retinoblastoma (Lan & Breslin (2009) *FASEB J.* 23: 2024-2033). Therefore, INSM1 is a NE-specific tumor marker.

To assist with the detection of NE tumors despite their heterogeneous population, the INSM1-promoter's specificity in NE tumors was used to drive the expression of a downstream *Gaussia* luciferase gene. Secreted luciferases like *Metridia* or *Gaussia* luciferase have been shown to be highly luminescent, exhibiting 2-4-fold higher signal than *Renilla* or firefly luciferases (El-Amouri et al., (2013) *Mol. Biotechnol.* 53: 63-73; Koutsoudakis et al., (2012) *PLoS One* 7: e53254). INSM1p-Met and INSM1p-Gau reporter vectors to measure the INSM1 promoter activity in NE tumors were constructed. In vitro cell lines and xenograft human tumor cultured cells revealed positive luciferase secreted from NE tumors. In addition, combining the INSM1p-Δ24E1A and INSM1p-Gau luciferase vectors increased the sensitivity of secreted *Gaussia* in vivo. The Δ24E1A gene, a mutant form of the adenovirus E1A gene with a 24 base pair deletion, is inactive in retinoblastoma (Rb) protein expressing cells and active in Rb negative cancer cells (Whyte et al., (1988) *Nature* 334: 124-129). The cancer specificity from the modified INSM1 promoter and the Δ24E1A gene create a dual layer of safety against non-specific expression.

Materials and Methods

Construction of adenoviral vectors. The Ad-INSM1p-Met construct was cloned using an original pGL3-INSM1p vector that contained the modified INSM1-promoter with HS4 insulator upstream and 2×NRSE downstream (Akerstrom et al., (2012) *Cancer Gene Ther.* 19: 828-838). The *Metridia* luciferase gene was excised from the pMet-Reporter vector (Clontech, Mountain View Calif.) and ligated downstream of the modified INSM1-promoter in pGL3. The pGL3 vector was cut to release the INSM1p-Met fragment, which was then ligated into the pShuttle plasmid (Agilent Technologies, Santa Clara Calif.) for adenoviral vector.

The Ad-INSM1p-Gau and Ad-INSM1p-Δ24E1A constructs were cloned using the modified INSM1-promoter on the pGL3-INSM1p vector, created by shortening the full insulator sequence into two copies of the core HS4 insulator. The *Gaussia* luciferase gene was obtained from the pMCS-*Gaussia*-Dura Luc vector (ThermoFisher Scientific, Waltham Mass.) and ligated downstream of the INSM1-promoter to create pGL3-INSM1p-Gau. To clone the Δ24E1A gene, site directed mutagenesis was performed on an existing E1A gene in the pJet plasmid (ThermoFisher Scientific, Waltham Mass.) to delete 24 base pairs from the original sequence. This Δ24E1A gene was then cloned into the pGL3 vector to form pGL3-INSM1p-Δ24E1A. Both the INSM1p-Gau and the INSM1p-Δ24E1A fragments were excised from their vectors and placed into the pShuttle plasmid. The Ad-SV40-Luc2 construct was generated by excising the SV40 promoter from the pSEAP2-Control vector (Clontech) and ligated upstream of the Luc2 reporter gene in the pGL4.10 vector (Promega, Madison Wis.). The SV40-Luc2 fragment was cloned into the pShuttle vector. The pShuttle plasmid was linearized and electroporated into BJ5183-AD-1 cells (Agilent Technologies, Santa Clara Calif.) to undergo recombination. After selection for the recombinants, linear adenoviral DNA was transfected into AD293 cells (Agilent Technologies, Santa Clara Calif.) using FuGENE 6 reagent (Promega, Madison Wis.). The virus was amplified onto forty 150 mm tissue culture dishes and purified by CsCl gradient. This purified virus was then titered using the Adeno-X-Rapid Titer Kit (Clontech, Mountain View) and stored at −80° C. All sequences in the cloning process were verified through DNA sequencing.

In vivo luciferase imaging. Nu/Nu mice aged 8-10 weeks old received intravenous tail vein injection of either the modified first generation Ad-INSM1p-Luc2, the second generation Ad-INSM1p-Luc2, or unmodified Ad-INSM1p-Luc2. The viruses were prepared in phosphate-buffered saline at a concentration of $10^{10}$ ifu per ml and 100 µl of the viral solution was delivered slowly into the tail vein via a 27 gauge needle. To perform the imaging analysis for luciferase activity, D-luciferin substrate (Biosynth, Itasca Ill.) was prepared at a concentration of 15 mg/ml and injected intraperitoneally into mice at a dose of 150 mg/kg. Once injection was completed, the mice were anesthetized in an isofluorane chamber (2-4% by inhalation) before being transferred to a Kodak In-Vivo Multispectral FX imager (Carestream Health, Rochester N.Y.). Using the imager's software, luminescence was acquired with a 10 minute exposure and an X-ray image of the mice in the same position was acquired with a 2 minute exposure. Imaging was performed 48 hours after virus injection and periodically up to 28 days. To generate the complete image, the luminescence acquisition was converted into a rainbow intensity scale and superimposed onto the X-ray acquisition using ImageJ software (National Institutes of Health, Bethesda Md.). For the NE tumor imaging, H1155 NE lung tumor cells ($1\times10^7$) were pre-infected with the second generation modified Ad-INSM1p-Luc2 virus (50 MOI) for 24 hours and injected subcutaneously into the right hind flank of nude mice (n=3). After one week, the tumor growth was evidenced and imaged to show the modified INSM1 promoter specificity.

In vitro Metridia and Gaussia luciferase secretion assay. Cells were seeded in a 96-well plate at a density of 10,000 cells per well. After incubation at 37° C. and 5% $CO_2$ for 1 h, cells were infected with either no virus (negative control), Ad-INSM1p-Met (0 to 50 MOI), Ad-INSM1p-Gau (0 to 50 MOI), or Ad-SV40-Luc2 (5 MOI). Infected cells were then incubated at 37° C., 5% $CO_2$ for 24 h. After incubation, each well was washed gently with 1×PBS and replaced with fresh media for another 24 hours. Fifty microliters of media per well were transferred to a 96-well white microplate. Luminescence was detected using the Pierce Gaussia Luciferase Glow Assay kit (ThermoFisher Scientific, Waltham Mass.), and read on a TopCount NXT Microplate Scintillation and Luminescence Counter. The adenoviral infection efficiency was determined by normalization (ratio) with intracellular luciferase (Ad-SV40-Luc2) using the Dual-Glo Luciferase Assay System (Promega, Madison Wis.) and read on a TopCount NXT Microplate Scintillation and Luminescence Counter. To test the effects of Ad-INSM1p-Gau in combination with the Ad-INSM1p-Δ24E1A conditionally replicating adenovirus, cells were infected with a combination of 10 MOI Ad-INSM1p-Gau and Ad-INSM1p-Δ24E1A for a total of 20 MOI ($2\times10^5$ ifu). Media was collected 2, 4, and 6 days (20 µl each day) after infection to determine secreted luciferase activity. Luminescence was detected using the Pierce Gaussia Luciferase Glow Assay kit (ThermoFisher Scientific, Waltham Mass.), then read on a TopCount NXT Microplate Scintillation and Luminescence Counter. The Student's T-test with a threshold of p<0.05 was used to determine statistical significance. This process was repeated with the Ad-INSM1p-Gau infected cells to determine the Ad-INSM1p-Gau/Ad-SV40-Luc2 ratio.

Xenograft human tumor culture assay. Xenograft tumors were prepared by injecting human tumor cells ($1\times10^7$), such as HeLa, U87, D283, UMC-11, SK-NBe(2), H1155, and H69 subcutaneously into the right hind flank of nude mice. Tumor tissues were harvested and frozen (−80° C.) in RPMI 1640 culture medium with 10% DMSO. The cultured tumor cells were prepared by rapidly thawing in a 37° C. water bath and subsequent mincing into small sections approximately 1 $mm^3$ in size. The minced tissues were then centrifuged at 250×g for 1 minute and incubated in 2.5% trypsin for a total of 30 minutes at 37° C. and 2 ml growth media was added to neutralize the trypsin. The trypsinized tissues were then filtered through a 70 µm sieve and centrifuged again at 250×g for 5 minutes. The 96-well clear-bottom plates were coated with 75 µl per well of a 1:6 dilution of Matrigel in RPMI growth media and then incubated for 30 minutes at 37° C. The tumor cells (10,000 cells) were re-suspended in RPMI media and added to each Matrigel coated well. Cells from each tumor were infected with Metridia-luciferase and Ad-SV40-Luc2 at 37° C. for 24 hours. The ratio of Metridia/Luc2 luciferase was calculated and averaged using RFU from 50 µl media per well. Detection of serum Gaussia luciferase in vivo. Eight week old Nu/Nu mice (National Cancer Institute, Bethesda Md.) were injected with H1155 NE lung tumor cells ($1\times10^7$) subcutaneously into the right hind flank. Tumors were allowed to establish until tumor size grew to at least 0.1 $cm^3$ in volume. The mice were injected intra-tumorally with $1\times10^9$ ifu of Ad-INSM1p-Luc2 virus, or a combination of $5\times10^8$ ifu of Ad-INSM1p-Gau and Ad-INSM1p-Δ24E1A (for a total of $1\times10^9$ ifu). To detect the Gaussia expression in the bloodstream, 100 µl of blood was drawn at 3, 6, 9, and 12 days after virus injection. All animal experiments were performed in accordance with the approved protocol from the Institutional Animal Care and Use Committee, Louisiana State University Health Sciences Center New Orleans. The collected blood was allowed to clot for 30 minutes at room temperature and centrifuged at 2,000 g for 10 minutes. Serum was collected from the supernatant and diluted with PBS at a 1:10 ratio. To detect Gaussia luciferase in the serum, 50 µl of the diluted serum from each sample was added to a flat bottom 96 well plate for the Gaussia luciferase assay.

Statistical Analysis. Values were corrected and expressed relative to a control group. All experiments were repeated three times. Results are presented as mean±SEM. Statistical analysis was performed using wither the Student's t-test when only two groups were in the experiment or by an one-way ANOVA comparison of multiple groups using the Tukey-Kramer test with differences at p value of less than 0.05 being considered significant.

Cloning the INSM1-promoter driven adenoviral constructs. To generate an adenoviral vector that is useful for the diagnosis of INSM1-positive NE tumors, the first generation modified INSM1-promoter was constructed by inserting a full HS4 insulator sequence upstream of the INSM1-promoter (approximately 1.7 kb) along with two NRSE enhancer sequences in tandem repeats downstream and Luc2 gene (FIG. 12A) (Akerstrom et al., (2012) Cancer Gene Ther. 19: 828-838). The modified INSM1-promoter drives a downstream Metridia luciferase gene, resulting in the construct Ad-HS4ins-INSM1p-2×NRSE-*Metridia* (Ad-INSM1p-Met) (FIG. 12B). A second generation of the modified INSM1-promoter was constructed to drive the expression of *Gaussia* luciferase and Δ24E1A. This promoter was created using two copies of the HS4 core insulator in place of the full insulator sequence. The final constructs Ad-2×HS4Core-INSM1p-2×NRSE-*Gaussia* (Ad-INSM1p-Gau) and Ad-2×HS4Core-INSM1p-2×NRSE-Δ24E/A (Ad-INSM1p-Δ24E/A), have a modified INSM1-promoter that is ~700 bp shorter than that of the promoter in Ad-INSM1p-Met (FIG. 12C, 12D). Ad-SV40-Luc2 vector was constructed as a control vector (FIG. 12E).

Figure 17:
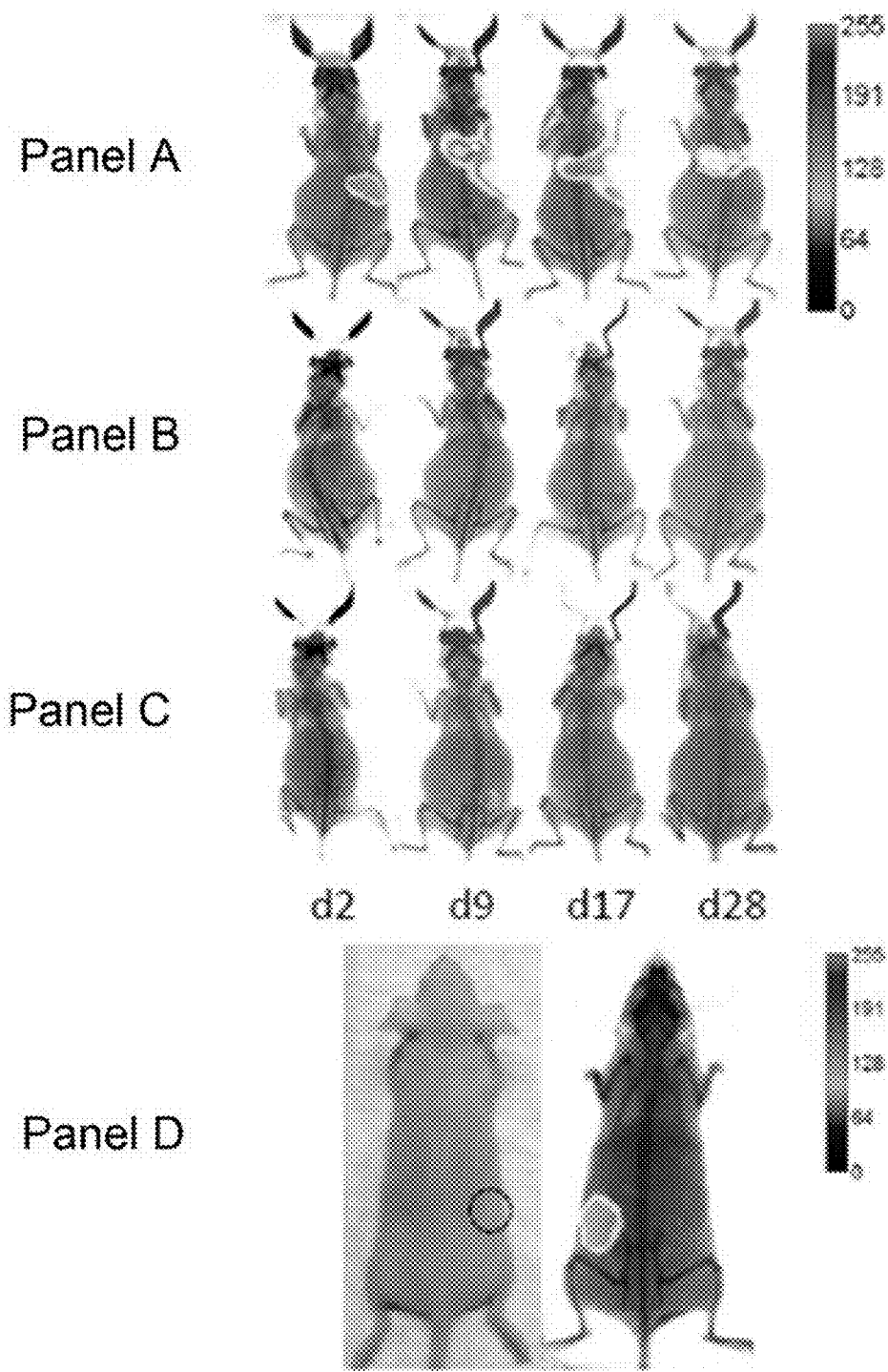
FIG. 17 is a series of digital images illustrating the specificity, un-modified INSM1-promoter driven Ad-INSM1p-Luc2 ($1 \times 10^9$) was injected intravenously into non-tumor bearing Nu/Nu mice and the luciferase signal was measured from days 2 to 28 post injection: Panel A: The first generation; Panel B: second generation modified INSM1- promoter driven Ad-INSM1p-Luc2 (1×10⁹) do not show luciferase activity as INSM1 promoter retains its specificity; Panel C: For the NE tumor imaging, the modified Ad-INSM1p-Luc2 virus was pre-infected with H1155 NE lung tumor cells (50 MOI) and injected subcutaneously into the right hind flank of nude mice (n=3). After one week, the tumor growth was evidenced and imaged to show the modified INSM1 promoter specificity. Mouse tumor was faced down for luciferase imaging.

It was examined whether an adenoviral vector driven by the modified INSM1-promoter would result in non-specific expression in vivo. Tail vein injection was performed using three viral vectors, the un-modified Ad-INSM1p-Luc2 (FIG. 17A), the first generation of the modified Ad-INSM1p-Luc2 (FIG. 17B), and the second generation modified Ad-INSMp-Luc2 (FIG. 17C) injected into non-tumor bearing Nu/Nu mice separately. Therefore, the INSM1 promoter specificity with or without HS4 insulator and NRSE enhancer sequence was examined. After a period of 2-28 days, luciferase activity was determined via in vivo imaging system after intraperitoneal (i.p.) injection of luciferin substrate using a Kodak In-Vivo Multispectral FX imager. The intravenous injected adenovirus usually harbored in the liver (>90%). In the non-tumor bearing mice that were injected with the original un-modified Ad-INSM1p-Luc2, it was observed that non-specific luciferase expression occurred and was focused primarily in the liver area. In contrast, both the first and second generation modified Ad-INSM1p-Luc2 did not exhibit non-specific luciferase expression after luciferin administration. To further demonstrate that the modified Ad-INSM1p-Luc2 virus maintains NE tumor specificity, an Ad-INSM1p-Luc2 pre-infected H1155 NE tumor was established in nude mice and showed tumor imaging by luciferase readily (FIG. 17D). These results determined that the modified INSM1-promoter (both first and second generation) is essential in blocking the effects of adenoviral regulatory elements to retain tumor specificity in vivo. Ad-INSM1p-Met displays INSM1 specificity in vitro. An adenoviral vector to express secreted *Metridia* luciferase specifically driven by the modified INSM1-promoter for the detection of NE tumors was constructed. Secreted *Metridia* was measured in vitro by co-infecting tumor cells with Ad-INSM1p-Met vector (Ad-HS4ins-INSM1p-2×NRSE-*Metridia*) and Ad-SV40-Luc2. The addition of Ad-SV40-Luc2 virus was used to normalize the infection efficiency using the ratio between extracellular and intracellular luciferase activity.

Both INSM1-negative and INSM1-positive tumor cell lines including lung carcinoma, neuroblastoma, medulloblastoma, pheochromocytoma, and insulinoma were infected with Ad-INSM1p-Met/Ad-SV40-Luc2 for 48 hours (FIGS. 18A-18C). The secreted luciferase activity in the media was readily detected in all of the INSM1-positive cell lines (solid lines). In particular, the INSM1-positive cell lines H82, βTC-1, and WERI-Rb-1 exhibited the highest Ad-INSM1-Met/Ad-SV40-Luc2 luminescence ratios. At the highest MOI (50:1), secreted luciferase activity reached higher than two-fold that of the intracellular luciferase activity (FIGS. 18A-18C). In contrast, the INSM1-negative tumor cell lines (dot lines) showed no secreted *Metridia* luciferase relative to intracellular luciferase.

To assess the efficacy of INSM1-promoter driven *Metridia* luciferase adenoviral vector in xenograft human tumors, human tumor cultured cells derived from previously established xenograft tumor were collected and grown in culture. These ex vivo tumor cells were co-infected with Ad-INSM1p-Met and Ad-SV40-Luc2 to determine the ratio between extracellular and intracellular luciferase activity. After incubation for 3 days, it was determined that INSM1-positive cells (UMC-11, SK-N-Be(2), H1155, H69, except D283) infected by Ad-INSM1p-Met expressed extracellular *Metridia* luciferase that produced signals as high as 1.6 times the intracellular firefly luciferase (FIG. 19). In contrast, INSM1-negative cells (HeLa and U87) produced low levels of extracellular *Metridia* luciferase that did not exceed 0.11 times the activity of intracellular firefly luciferase.

INSM1 promoter-driven *Gaussia* luciferase retains specificity: In preparation for further in vivo assays, a *Gaussia* luciferase expression vector was preferred due to the increased stability of *Gaussia* luciferase in vivo. As recent studies have shown, *Gaussia* luciferase signals were detectable after tail-vein injection in mice, due to its increased temperature stability compared to *Metridia* luciferase. To determine the specificity of the newly constructed *Gaussia* luciferase construct Ad-INSM1p-Gau, an in vitro luciferase assay was conducted to evaluate whether the Ad-INSM1p-Gau vector (Ad-2×HS4Core-INSM1p-2×NRSE-*Gaussia*) could specifically express *Gaussia* luciferase in INSM1-positive cell lines in a similar fashion as did the Ad-INSMp-Met vector. After co-infection with Ad-INSM1p-Gau/Ad-SV40-Luc2, it was possible to see significant secreted luminescent activity in the media of all INSM1-positive cell lines (solid lines) as compared to INSM1-negative control cell lines (dot lines) (FIGS. 20A-20C). In particular, the INSM1-positive cell lines βTC-1, RIN, H82, and H1155 exhibited the highest Ad-INSM1-Gau/Ad-SV40-Luc2 ratios. Secreted *Gaussia* luciferase was not detected in any INSM1-negative cell lines, indicating INSM1 promoter retains specificity in vitro.

Conditional replicating vector (Ad-INSM1p-Δ24E1A) enhances *Gaussia* luciferase secretion and sensitivity over time in an in vivo mouse xenograft tumor model. After establishing the specificity of the Ad-INSM1p-Gau vector, it was determined whether infecting cells with Ad-INSMp-Δ24E/A in combination with Ad-INSM1p-Gau could increase the secreted luciferase signal. Accordingly, if an INSM1-positive cell is infected concurrently with both viruses, Δ24E1A expression from Ad-INSM1p-Δ24E1A can be utilized by both viruses to facilitate replication. The replication of Ad-INSM1p-Gau would lead to viral amplification and increased *Gaussia* luciferase secretion over time.

Therefore, H1155 NE lung carcinoma cells or SK-N-Be (2) neuroblastoma cells were co-infected with Ad-INSM1p-Gau alone (20 MOI) or in combination with Ad-INSM1p-Δ24E1A at a concentration of 10 MOI each (FIG. 21). Six days after infection, the combination viruses displayed a 2-fold increase in secreted luminescent activity as compared to infection with Ad-INSM1p-Gau alone. This result suggested that the combination viruses could indeed amplify inside an INSM-positive cell in vitro.

It was analyzed whether the combination of Ad-INSM1p-Gau and Ad-INSM1p-Δ24E1A viruses could secrete detectable amount of *Gaussia* luciferase into the circulation from a tumor bearing animal for an extended period of time. In this experiment, subcutaneous H1155 tumors (approximately 0.1 cm$^3$) were first established on the right flank of Nu/Nu mice. These tumor-bearing mice (n=3) were then injected intra-tumorally with either Ad-INSM1p-Luc2 or the Ad-INSM1p-Gau and Ad-INSM1p-Δ24E1A virus combination at a total concentration of 1×10$^9$ ifu (FIG. 22). After infection with the virus combination for 6 days, detectable luciferase signal was observed in the serum ($p<0.01$). The signal increased in intensity by day 9 and lasted up to 12 days, the humane endpoint for the tumor bearing animals. The Ad-INSM1p-Luc2 infected tumor released no *Gaussia* luciferase into the circulation and was used as the control.

Although the original INSM1-promoter possesses NE-tumor specificity, it was found that the promoter loses its specificity when used in an adenoviral setting. It has been demonstrated that an INSM1-promoter driven adenoviral reporter construct displayed non-specific expression after tail vein injection in an in vivo mouse model (Akerstrom et al., (2012) *Cancer Gene Ther.* 19: 828-838). It was hypothesized that this loss of specificity was due to the presence of overpowering viral enhancers that were otherwise not present in normal cells. To override these adenoviral regulatory elements, an insulator sequence derived from the HS4 chicken β-globin insulator was placed upstream of the INSM1-promoter to block effects from any viral enhancers. In addition, two copies of the neuron-restrictive silencer element (NRSE), a regulatory element with dual functions to silence the INSM1 promoter in non-neuronal cells while enhancing it in neuronal cells, were placed downstream of the promoter. Once these elements were added, the modified INSM1-promoter was able to retain its high specificity in an adenoviral vector (Akerstrom et al., (2012) *Cancer Gene Ther.* 19: 828-838).

To further improve upon this original design, the 1.2 kb full insulator sequence has been replaced with two copies of the HS4 core insulator (250 bp×2) to create the second generation modified INSM1 promoter. Although the 1.2 kb full insulator sequence has been well characterized functionally, the 250 bp core insulator was observed to exhibit the same protective activity as the full sequence (Aker et al., (2007) *Hum. Gene Ther.* 18: 333-343). An advantage of switching from a full insulator sequence to the core sequence is that utilization of two copies of the 250 bp core would free approximately 700 bp of space for the assembly of larger transgenic sequences in the viral vector. Essentially, this more compact form of the modified INSM1-promoter displays the same NE tumor specificity with the additional advantage of allowing more flexible cloning strategies.

Retaining the specificity of the INSM1-promoter in an adenoviral vector has allowed the construction of a *Gaussia* luciferase reporter vector that can detect the presence of NE tumor in vivo. When paired with a conditionally replicating oncolytic virus, the virus combination allowed for continuous expression of *Gaussia* luciferase for the duration of the tumor's progression. These results can have a significant impact on monitoring tumor progression during the treatment of patients. Given that the viruses can selectively replicate in NE tumor cells, *Gaussia* luciferase expression will persist and intensify as the tumor increases in size. Conversely, if treatment of the tumor is successful, luciferase expression in the patient's blood will decrease as tumor size is reduced. Provided is evidence that the *Gaussia* vector can be used in combination with a treatment protocol to monitor a patient's treatment outcome. An alternative use for this virus during the treatment of a NE tumor would be to discern whether a tumor is removed completely after surgical resection. By injecting the virus combination into the resection site during the surgical procedure, clinicians would be able to monitor the presence of INSM1-positive NE tumor cells based on a *Gaussia* luciferase readings from the patient's blood. Continuous monitoring of expression levels will allow for a better prognosis in these patients post-procedure by alerting clinicians to an incomplete resection.

Using the Ad-INSM1p-Gau vector in combination with the Ad-INSM1p-Δ24E1A was discovered to be more advantageous as compared to using Ad-INSM1p-Gau alone. In NE tumor cells infected by the virus combination, *Gaussia* luciferase expression was significantly higher than that of the Ad-INSM1p-Gau virus (20 MOI) alone after 6 days post infection, even though the number of infectious units of Ad-INSM1p-Gau (10 MOI) was lower at the start for the combination. This indicates that the addition of Δ24E1A expression in cells infected by the *Gaussia* virus allowed for conditional replication of the reporter vector. This replication has the potential to significantly increase the copy number of the virus over several days, leading to an increase in sensitivity of *Gaussia* luciferase detection. Therefore, the most efficient method of increasing the sensitivity of infection seems to involve utilization of conditionally replicating viruses, as opposed to simply increasing the infectious units during administration of the virus.

Taken together, the Ad-INSM1p-Gau virus has the potential to be an easy-to-use and highly sensitive tool for the detection of NE tumors in the clinical setting. While a viral construct cannot currently be used as a diagnostic tool for the general population, it can be an alternative approach to track the tumor progression in patients with existing NE cancers. Additionally, it could also be used diagnostically in populations where a NE tumor is suspected. In these cases, the virus combination could act as both a diagnostic tool and as a way to monitor tumor progression.

Example 3

Small cell lung carcinomas are a group of highly malignant neuroendocrine (NE) cancers that have poor prognosis due to high rates of growth and metastasis. Characteristically a diffuse, non-solid tumor, patients with SCLC most often rely on radiation and chemotherapy for treatment. In the case of unresponsive or relapsing tumors, treatment options become limited and median survival is low. To increase treatment options for SCLC patients, it has been possible to generate a conditionally replicating adenovirus that can specifically replicate and express therapeutic genes in NE tumor cells. The expression of these adenoviruses is regulated upstream by an insulinoma-associated-1 (INSM1) promoter, which is silent in normal adult tissues but active in NE tumors and developing NE tissues. By placing the INSM1-promoter in an adenoviral construct, the construct can retain tumor specificity and drive expression of a mutated adenovirus E1A gene (Δ24E1A) or the herpes simplex virus thymidine kinase (HSV-TK) gene.

In vitro cell line and subcutaneous mouse tumor models revealed that the INSM1-promoter driven constructs were able to replicate specifically in INSM1-positive cells. INSM1 specific HSV-TK expression in combination with ganciclovir treatment displayed dose-dependent tumor cell death in NE tumor cells, leaving INSM1-negative cells unharmed. When combined, the INSM1-promoter driven HSV-TK with Δ24E1A, directed co-infected NE tumors to express higher levels of HSV-TK and more efficient tumor suppression compared to the INSM1p-HSV-TK virus alone.

In an orthotopic mouse lung model, SCLC tumors established in the lungs were treated with INSM1 driven adenoviruses by delivery through the nasal passage to realistically simulate lung cancer progression and treatment. Monitoring of the orthotopic lung tumors by luciferase signal revealed decreased tumor size after infection for up to 20 days. Taken together, INSM1-driven conditionally replicating adenoviruses represent a new tool for the treatment of SCLCs, giving clinicians additional options to combat this deadly disease.

Generation and use of oncolytic viruses (as shown in FIGS. 23-31): The pGL3 INSM1p plasmid contains the INSM1 promoter and was digested and ligated with the Δ24E1A and HSV-TK genes linked by an internal ribosomal entry site (IRES). To clone the Δ24E1A gene, site directed mutagenesis was performed on an existing E1A gene in the pJet plasmid to delete 24 base pairs from the original sequence. The HSV-TK gene was cut from the pWS plasmid while IRES element was subcloned from the pIRES element vector (Clonetech). After ligation, the pGL3 vector was cut and the INSM1p-Δ24E1A-IRESHSV-TK fragment was placed into the pShuttle plasmid, then linearized and electroporated into BJ5183-AD-1 cells for recombination. After recombination, adenoviral DNA was transfected into AD293 cells to be grown and amplified. The final virus will be titered using the AdenoXTiter Assay (Clonetech) and purified using CsCl density gradient centrifugation.

Western blot: After viral infection for 48 hours, total protein extracts were isolated from each infected cell line and anti-E1A and anti-HSVTK antibodies were used to detect protein expression. Anti-GAPDH and anti-CAR antibodies were used as control.

Cell survival assays: Cell lines were infected by viruses at increasing multiplicities of infection (MOI), starting at 0 and increasing in orders of magnitude to 0.1, 1, and 10 MOI. All cells will be incubated for 5 days, after which cell survival was measured by MTS Assay (Promega). Absorbance at 490 nm was measured and plotted against MOI. Crystal violet staining was performed at 0.1, 1, and 10 MOI after infection for 5 days.

Viral titer assay: H1155 cells were plated on 6-well plates at a density of $2 \times 10^6$ cells/well and infected with a viral concentration of 5 MOI. After incubation for approximately 3 days, cells were collected and viral particles released by freeze thaw lysis. The isolated virus were then titered by immunostaining.

Mouse xenograft tumors: A total of $10^9$ cells were injected either subcutaneously into the right flank or orthotopically into the left lung of 4 week old Nu/Nu mice. After establishment of tumor, viruses were introduced by direct injection in a subcutaneous tumor or through nasal inhalation for a lung tumor.

Through western blot, viral constructs where shown to express ΔE1A and HSVTK. Additionally, the combination virus expressed higher levels of ΔE1A and HSVTK than either virus alone.

INSM1 promoter driven virus limited its expression specifically to INSM1 positive cell lines in vitro, leaving INSM1 negative cells unaffected.

Cell survival assays revealed the combination of ΔE1A and HSVTK was more effective at killing than ΔE1A alone. The combination virus was shown to amplify after infecting an INSM1 positive cell.

The combination viruses displayed effective suppression of subcutaneous tumors. Depending on the aggressiveness of the specific tumor cell, suppression of tumors lasted up to 28 days.

The combination viruses were effective at suppressing orthotopically established lung tumors after administration through the nasal passage. This suppression was observed for up to 20 days using luciferase imaging.

Example 4

TABLE 1

| | Sequences used to generate the constructs of the disclosure: | |
|---|---|---|
| FIG. 2 | INSM1 promoter (−1661-+bp) | SEQ ID NO: 1 |
| FIG. 3 | tandem N-Acetylcholine Receptor (nAchR) neuronal restrictive silencer elements (NRSEs) having a 5' terminal BgIII restriction site and a 3' HindIII restriction site | SEQ ID NO: 2 |
| FIG. 4 | HS4 insulator sequence (approximately 1.2 kb) | SEQ ID NO: 3 |
| FIG. 5 | HS4 core sequence (approximately 250 bp) | SEQ ID NO: 4 |
| FIG. 6 | Gaussia bioluminescent reporter having a 5' terminal HindIII restriction site and a 3' NotI restriction site | SEQ ID NO: 5 |
| FIG. 7 | IRES element | SEQ ID NO: 6 |
| FIG. 8 | Δ24E1A polypeptide having the nucleotide sequence | SEQ ID NO: 7 |
| FIG. 9 | amino acid sequence of human E1A polypeptide. | SEQ ID NO: 8 |
| FIG. 10 | nucleotide sequence encoding a thymidine kinase (TK) | SEQ ID NO: 9 |
| FIG. 11 | nucleotide sequence of an 3'-untranslated region | SEQ ID NO: 10 |
| FIG. 32 | Nucleotide sequence of 2Xins-INSM1p--2XNRSE-Δ24E1A-IRES-HSV-tk construct that may be inserted into adenovirus 5 viral vector | SEQ ID Nos: 11 |
| FIG. 33 | Nucleotide sequence of 2Xins-INSM1p--2XNRSE-Δ24E1A-IRES-HSV-tk construct that may be inserted into adenovirus 5 viral vector | SEQ ID Nos: 12 |
| FIG. 34 | Nucleotide sequence of 2Xins-INSM1p-2XNRSE-Δ24E1A-3'-untranslated region construct that may be inserted into adenovirus 5 viral vector | SEQ ID NO: 13 |
| FIG. 35 | Nucleotide sequence of a 2Xins-INSM1p-2XNRSE-Gaussia-3'-untranslated region construct that may be inserted into and adenovirus 5 (Ad5) viral vector | SEQ ID NO: 14 |

We claim:

1. A composition comprising a first neuroendocrine tumor-specific viral expression vector and a second neuroendocrine tumor-specific viral expression vector, wherein the genome of the first neuroendocrine tumor-specific viral expression vector comprises:

(a) a human Insulinoma-associated 1 promoter (INSM1p) operatively linked to a nucleotide sequence encoding a tumor-selective modified human E1A polypeptide lacking the amino acid residues 121-128 of the amino acid sequence SEQ ID NO: 8;

(b) an insulator region upstream from said promoter, wherein said insulator region comprises an insulator element or a tandem pair of core insulator elements;

(c) a pair of tandem neuronal restrictive silencer elements (NRSE) downstream from said promoter; and (d) at least one nucleotide sequence encoding a 3'-untranslated region wherein:

(i) said insulator region is adapted to block the influence of viral regulatory elements on the transcription within mammalian cells of said nucleotide sequence of (a), but not to affect the influence of the INSM1 promoter or the influence of the neuronal restrictive silencer elements on the transcription of said nucleotide sequence of (a);

(ii) said INSM1 promoter is adapted to cause the selective transcription of said nucleotide sequence of (a) in tumor cells of neuroendocrine origin; and (iii) said pair of tandem neuronal restrictive silencer elements are operatively linked to the INSM1 promoter, and are adapted to selectively repress the transcription of said nucleotide sequence of (a) in non-neuronal cells; and wherein the genome of the second neuroendocrine tumor-specific viral expression vector comprises:

(a') a human Insulinoma-associated 1 promoter (INSM1p) operatively linked to a nucleotide sequence encoding a polypeptide toxin lethal or conditionally lethal to cells in which the toxin is expressed or a polypeptide reporter molecule;

(b') an insulator region upstream from said promoter, wherein said insulator region comprises an insulator element or a tandem pair of core insulator elements;

(c') a pair of tandem neuronal restrictive silencer elements downstream from said promoter; and (d') a nucleotide sequence encoding a 3'-untranslated region, wherein:

(i) said insulator region is adapted to block the influence of viral regulatory elements on the transcription within mammalian cells of said nucleotide sequence of (a'), but not to affect the influence of said promoter or the influence of said neuronal restrictive silencer elements on the transcription of said nucleotide sequences of (a');

(ii) said INSM1 promoter is adapted to cause the selective transcription of said nucleotide sequence of (a') in tumor cells of neuroendocrine origin; and (iv) said tandem neuronal restrictive silencer elements are operatively linked to said promoter, and are adapted to selectively repress the transcription of said nucleotide sequence of (a') in non-neuronal cells.

2. The composition of claim 1, wherein the polypeptide toxin is herpes simplex virus thymidine kinase (HSV-tk).

3. The composition of claim 1, wherein the polypeptide reporter molecule is a luciferase 2, a *Renilla* luciferase, a *Metridia* luciferase, or a *Gaussia* luciferase.

4. The composition of claim 1, wherein the first neuroendocrine tumor-specific viral expression vector is a nonreplicating Ad5 adenoviral vector.

5. The composition of claim 1, wherein
the human INSM1 promoter comprises a nucleotide sequence having at least 95% similarity to SEQ ID NO: 1, the insulator region is a chicken HS4 β-globin insulator element comprising a nucleotide sequence having at least 95% similarity to SEQ ID NO: 3 or a pair of tandem core chicken HS4 β-globin insulator elements, each of said core elements comprises a nucleotide sequence having at least 95% similarity to SEQ ID NO: 4, the pair of tandem neuronal restrictive silencer elements comprises a nucleotide sequence having at least 95% similarity to SEQ ID NO: 2, the nucleotide sequence operably linked to the INSM1 promoter has at least 95% similarity to SEQ ID NO: 7 and encodes the tumor-selective modified E1A polypeptide β24E1A, and the 3'-untranslated region has a nucleotide sequence having at least 95% similarity to SEQ ID NO: 10.

6. The composition of claim 2, wherein the herpes simplex virus thymidine kinase (HSV-tk) is encoded by a nucleotide sequence having at least 95% similarity to SEQ ID NO: 9.

7. The composition of claim 1, wherein said composition further comprises a pharmaceutically acceptable carrier.

8. The composition of claim 1, wherein the composition is formulated for directed delivery to a tumor, intravenous delivery to a tumor, or respiratory delivery to a lung tumor.

9. The composition of claim 1, wherein the first neuroendocrine tumor-specific viral expression vector comprises a bicistronic vector whose genome comprises (e) an IRES element operatively linked upstream of one or more open reading frame nucleotide sequences encoding at least one of a polypeptide toxin lethal or conditionally lethal to cells in which the toxin is expressed and a secreted bioluminescent reporter molecule.

10. The composition of claim 9, wherein the nucleotide sequence operably linked to the IRES element encodes the conditionally lethal toxin herpes simplex virus thymidine kinase (HSV-tk).

11. The composition of claim 9, wherein the secreted bioluminescent reporter molecule is a luciferase 2, a *Renilla* luciferase, a *Metridia* luciferase, or a *Gaussia* luciferase.

12. The composition of claim 9, wherein the IRES element has a nucleotide sequence having at least 95% similarity to SEQ ID NO: 6.

13. The composition of claim 10, further comprising the herpes simplex virus thymidine kinase (HSV-tk) having a nucleotide sequence having at least 95% similarity to SEQ ID NO: 9.

* * * * *